(12) United States Patent
Milne-Edwards et al.

(10) Patent No.: US 6,787,647 B1
(45) Date of Patent: Sep. 7, 2004

(54) CARNITINE CARRIER RELATED PROTEIN-1

(75) Inventors: Jean-Baptiste Dumas Milne-Edwards, Paris (FR); Aymeric Duclert, Saint-Maur (FR); Lydie Bougueleret, Petit Lancy (CH); Catherine Clusel, Montreuil-sous-Bois (FR)

(73) Assignee: Genset S.A. (FR)

( * ) Notice: Subject to any disclaimer, the term of this patent is extended or adjusted under 35 U.S.C. 154(b) by 193 days.

(21) Appl. No.: 09/599,361

(22) Filed: Jun. 21, 2000

Related U.S. Application Data

(63) Continuation-in-part of application No. 09/469,099, filed on Dec. 21, 1999, now abandoned.
(60) Provisional application No. 60/113,686, filed on Dec. 22, 1998, and provisional application No. 60/141,032, filed on Jun. 25, 1999.

(51) Int. Cl.$^7$ .................. C07H 21/04; C07H 21/02; C12Q 1/68; C12N 1/20; C12N 15/00; C12N 5/02; A01N 43/04; A61K 38/00
(52) U.S. Cl. ............... 536/23.5; 435/6; 435/252.3; 435/320.1; 435/325.1; 514/44; 530/300; 536/23.1
(58) Field of Search .............. 435/6, 252.3, 320.1, 435/325.1; 536/23.1, 23.5; 530/300; 514/44

(56) References Cited

FOREIGN PATENT DOCUMENTS

WO        WO 00 37491 A      6/2000

OTHER PUBLICATIONS

Bonnet et al., "Arrhythmias and Conduction Defects as Presenting Symptoms of Fatty Acid Oxidation Disorders in Children," Circulation, Nov., 1999, vol. 100, No. 22, pp. 2249–2253.*

Accession No. AA677293 on GenBank, Hillier et al., Dec. 19, 1997.*
Indiveri, et al.; "The mitochondrial carnitine carrier protein: cDNA cloning, primary structure and comparison with other mitochondrial transport proteins"; Biochemical Journal; vol. 321, No. 3, 1997, pp. 713–719; ISSN: 0264–6021.
Gustafson, et al.; "Regulation of carnitine binding to plasma mebranes by an ATP–Dependent Mechanism"; Biochemical and Biophysical Research Communications, U.S., Academic Press Inc., Orlando, FL; vol. 231, No. 2, 1997, pp. 249–253; ISSN: 0006–291X.
Palmieri, F., "Mitochondrial carrier proteins," *FEBS Lett.* 346:48–54 (1994).
Indiveri, C., et al., "The mitochondrial carnitine carrier protein: cDNA cloning, primary structure and comparison with other mitochondrial transport proteins," *Biochem. J.*, 321:713–719, (1997).
Iacobazzi, V., et al., "The Structure and Organization of the Human Carnitine/Acylcarnitine Translocase (CACT[1]) Gene[2]," *Biochem. Biophysic. Res. Commun.* 252:770–774 (1998).
Ježek, P., "Mammalian mitochondrial uncoupling proteins,", *Int. J. Biochem. Cell Biol.*, 30:1163–1168 (1998).

* cited by examiner

*Primary Examiner*—Kenneth R. Horlick
*Assistant Examiner*—Young Kim
(74) *Attorney, Agent, or Firm*—Saliwanchik, Lloyd & Saliwanchik

(57) ABSTRACT

The invention concerns CCRP-1 polynucleotides and polypeptides. The invention further relates to methods of directing polynucleotides, polypetides, and small molecules to mitochondria. The invention further relates to methods of reducing blood levels of fatty acids in an individual. The invention also concerns methods of identifying individuals who are at increased risk or who have a predisposition for developing, or present state of having, a diseases or disorder, such as obesity or heart disease, by determining the level of a CCRP-1 gene product in an individual.

14 Claims, 3 Drawing Sheets

Differential Expression of CCRP

Differential Expression of CCRP

Differential Expression of CCRP

| Lanes:<br>Rows | C57 N<br>(amount) | OB/OB<br>(amount) | DB/DB<br>(amount) | Caf fed<br>(amount) | NZO<br>(amount) |
|---|---|---|---|---|---|
| r1 | 100 | 100 | 100 | 100 | 100 |
| r2 | 329 | 768 | 841 | 662 | 375 |
| Sum | 429 | 868 | 941 | 762 | 375 |
| In Lane | 862 | 1370 | 1460 | 1360 | 1150 |

Fig. 1C

SEQUENCE LISTING

```
<160> NUMBER OF SEQ ID NOS:  2

<210> SEQ ID NO 1
<211> LENGTH: 1744
<212> TYPE: DNA
<213> ORGANISM: Homo Sapiens
<220> FEATURE:
<221> NAME/KEY: CDS
<222> LOCATION: 76..999
<221> NAME/KEY: sig_peptide
<222> LOCATION: 76..279
<223> OTHER INFORMATION: Von Heijne matrix
      score 5.10
      seq LSLPVCTVSLVSS/VS
<221> NAME/KEY: polyA_signal
<222> LOCATION: 1711..1716
<221> NAME/KEY: polyA_site
<222> LOCATION: 1729..1744
<221> NAME/KEY: misc_feature
<222> LOCATION: 336
<223> OTHER INFORMATION: n=a, g, c or t

<400> SEQUENCE: 1
aagttgaggc caccctggtg gcaccaaagc cctctcaggc aggcagaccc agggcctccc     60
cgccacacct tgttc atg gat ttt gtc gct gga gcc atc gga ggc gtc tgc    111
                Met Asp Phe Val Ala Gly Ala Ile Gly Gly Val Cys
                    -65                 -60 ggt gtt gct gtg ggc tac ccc ctg gac acg gtg aag gtc agg atc cag    159
Gly Val Ala Val Gly Tyr Pro Leu Asp Thr Val Lys Val Arg Ile Gln
    -55                 -50                 -45 acg gag cca aag tac aca ggc atc tgg cac tgc gtc cgg gat acg tat    207
Thr Glu Pro Lys Tyr Thr Gly Ile Trp His Cys Val Arg Asp Thr Tyr
-40                 -35                 -30                 -25 cac cga gag cgc gtg tgg ggc ttc tac cgg ggc ctc tcg ctg ccc gtg    255
His Arg Glu Arg Val Trp Gly Phe Tyr Arg Gly Leu Ser Leu Pro Val
                -20                 -15                 -10 tgc acg gtg tcc ctg gta tct tcc gtg tct ttt ggc acc tac cgc cac    303
Cys Thr Val Ser Leu Val Ser Ser Val Ser Phe Gly Thr Tyr Arg His
            -5                  1                   5 tgc ctg gcg cac atc tgc cgg ctc cgg tac ggn aac cct gac gcc aag    351
```

```
              Cys Leu Ala His Ile Cys Arg Leu Arg Tyr Gly Asn Pro Asp Ala Lys
                   10              15                  20 ccc acc aag gcc gac atc acg ctc tcg gga tgc gcc tcc ggc ctc gtc            399
Pro Thr Lys Ala Asp Ile Thr Leu Ser Gly Cys Ala Ser Gly Leu Val
 25              30                  35                  40 cgc gtg ttc ctg acg tcg ccc act gag gtg gcc aaa gtc cgc ttg cag            447
Arg Val Phe Leu Thr Ser Pro Thr Glu Val Ala Lys Val Arg Leu Gln
                 45                  50                  55 acg cag aca cag gcg cag aag cag cag cgg ctg ctt tcg gcc tcg ggg            495
Thr Gln Thr Gln Ala Gln Lys Gln Gln Arg Leu Leu Ser Ala Ser Gly
             60                  65                  70 ccg ttg gct gtg ccc ccc atg tgt cct gtg ccc cca gcc tgc cca gag            543
Pro Leu Ala Val Pro Pro Met Cys Pro Val Pro Pro Ala Cys Pro Glu
         75                  80                  85 ccc aag tac cgc ggg cca ctg cac tgc ctg gcc acg gta gcc cgt gag            591
Pro Lys Tyr Arg Gly Pro Leu His Cys Leu Ala Thr Val Ala Arg Glu
     90                  95                 100 gag ggg ctg tgc ggc ctc tac aag ggc agc tcg gcc ctg gtc tta cgg            639
Glu Gly Leu Cys Gly Leu Tyr Lys Gly Ser Ser Ala Leu Val Leu Arg
105                 110                 115                 120 gac ggc cac tcc ttt gcc acc tac ttc ctt tcc tac gcg gtc ctc tgc            687
Asp Gly His Ser Phe Ala Thr Tyr Phe Leu Ser Tyr Ala Val Leu Cys
                125                 130                 135 gag tgg ctc agc ccc gct ggc cac agc cgg cca gat gtc ccg ggc gtg            735
Glu Trp Leu Ser Pro Ala Gly His Ser Arg Pro Asp Val Pro Gly Val
            140                 145                 150 ctg gtg gcc ggg ggc tgt gca gga gtc ctg gcc tgg gct gtg gcc acc            783
Leu Val Ala Gly Gly Cys Ala Gly Val Leu Ala Trp Ala Val Ala Thr
        155                 160                 165 ccc atg gac gtg atc aag tcg aga ctg cag gca gac ggg cag ggc cag            831
Pro Met Asp Val Ile Lys Ser Arg Leu Gln Ala Asp Gly Gln Gly Gln
    170                 175                 180 agg cgc tac cgg ggt ctc ctg cac tgt atg gtg acc agc gtt cga gag            879
Arg Arg Tyr Arg Gly Leu Leu His Cys Met Val Thr Ser Val Arg Glu
185                 190                 195                 200 gag gga ccc cgg gtc ctt ttc aag ggg ctg gta ctc aat tgc tgc cgc            927
Glu Gly Pro Arg Val Leu Phe Lys Gly Leu Val Leu Asn Cys Cys Arg
                205                 210                 215 gcc ttc cct gtc aac atg gtg gtc ttc gtc gcc tat gag gca gtg ctg            975
Ala Phe Pro Val Asn Met Val Val Phe Val Ala Tyr Glu Ala Val Leu
                220                 225                 230 agg ctc gcc cgg ggt ctg ctc aca tagccggtcc ccacgcccag cggcccaccc          1029
Arg Leu Ala Arg Gly Leu Leu Thr
            235                 240 accagcagct gctggaggtc gtagtggctg gaggaggcaa ggggtagtgt ggctgggttc          1089
gggaccccac agggccattg cccaggagaa tgaggagcct ccctgcagtg ttgtcggccg          1149
aggcctaagc tcgccctgcc cagctactga cctcaggtcg aggggcccgc cagccatcag          1209
ccagggttgg cctagggtgg caggagccag ggaggagtgg gcctctttga tgagagcgtt          1269
gagttgcatg gagtcggttg ttcatcccag cctccccatg gccctcgcct ccatgtctt           1329 tgaagcaccc ctccagggag tcaggtgtgt gctcagccac cctctgcccc attcctagac          1389
cctcaccccc accactgttc ctgtgtcttc atgagctgtc ccttacaggc agggggcttcc         1449 cacaggctgg gggcctcggg gcggggagca tgagctgggc tggcaccacg actgagggct         1509
cccggcccgg cttcttcccc acagcaggct gctcagaggg ggtgctgccg ggactgccat         1569
gcccacctga gaggggcctg gggtggccgt cctcggccgg ttagggaatt tggggtgagg         1629
```

-continued

```
ttcctcagga gccctcactc tgcctgtgga cgctgcacct gccacttaaa gaccccaaag    1689
actctgttgg gaactgttgt caataaaatg tttctgagga aaaaaaaaaa aaaaa         1744
```

<210> SEQ ID NO 2
<211> LENGTH: 308
<212> TYPE: PRT
<213> ORGANISM: Homo Sapiens
<220> FEATURE:
<221> NAME/KEY: SIGNAL
<222> LOCATION: -68..-1

<400> SEQUENCE: 2

```
Met Asp Phe Val Ala Gly Ala Ile Gly Gly Val Cys Gly Val Ala Val
            -65                 -60                 -55

Gly Tyr Pro Leu Asp Thr Val Lys Val Arg Ile Gln Thr Glu Pro Lys
        -50                 -45                 -40

Tyr Thr Gly Ile Trp His Cys Val Arg Asp Thr Tyr His Arg Glu Arg
    -35                 -30                 -25

Val Trp Gly Phe Tyr Arg Gly Leu Ser Leu Pro Val Cys Thr Val Ser
-20             -15                 -10                  -5

Leu Val Ser Ser Val Ser Phe Gly Thr Tyr Arg His Cys Leu Ala His
                  1                   5                  10

Ile Cys Arg Leu Arg Tyr Gly Asn Pro Asp Ala Lys Pro Thr Lys Ala
         15                  20                  25

Asp Ile Thr Leu Ser Gly Cys Ala Ser Gly Leu Val Arg Val Phe Leu
 30                  35                  40

Thr Ser Pro Thr Glu Val Ala Lys Val Arg Leu Gln Thr Gln Thr Gln
45                  50                  55                  60

Ala Gln Lys Gln Gln Arg Leu Leu Ser Ala Ser Gly Pro Leu Ala Val
                 65                  70                  75

Pro Pro Met Cys Pro Val Pro Pro Ala Cys Pro Glu Pro Lys Tyr Arg
             80                  85                  90

Gly Pro Leu His Cys Leu Ala Thr Val Ala Arg Glu Glu Gly Leu Cys
         95                 100                 105

Gly Leu Tyr Lys Gly Ser Ser Ala Leu Val Leu Arg Asp Gly His Ser
    110                 115                 120

Phe Ala Thr Tyr Phe Leu Ser Tyr Ala Val Leu Cys Glu Trp Leu Ser
125                 130                 135                 140

Pro Ala Gly His Ser Arg Pro Asp Val Pro Gly Val Leu Val Ala Gly
                145                 150                 155

Gly Cys Ala Gly Val Leu Ala Trp Ala Val Ala Thr Pro Met Asp Val
            160                 165                 170

Ile Lys Ser Arg Leu Gln Ala Asp Gly Gln Gly Gln Arg Arg Tyr Arg
        175                 180                 185

Gly Leu Leu His Cys Met Val Thr Ser Val Arg Glu Glu Gly Pro Arg
    190                 195                 200

Val Leu Phe Lys Gly Leu Val Leu Asn Cys Cys Arg Ala Phe Pro Val
205                 210                 215                 220

Asn Met Val Val Phe Val Ala Tyr Glu Ala Val Leu Arg Leu Ala Arg
                225                 230                 235

Gly Leu Leu Thr
            240
```

CARNITINE CARRIER RELATED PROTEIN-1

RELATED APPLICATIONS

The present application is a continuation-in-part of U.S. application Ser. No. 09/469,099 filed Dec. 21, 1999 now abandoned, and claims priority from U.S. Provisional Patent Application Serial No. 60/113,686, filed Dec. 22, 1998, and U.S. Provisional Patent Application Serial No. 60/141,032, filed Jun. 25, 1999, the disclosures of which are incorporated herein by reference in their entireties.

FIELD OF THE INVENTION

The present invention is directed to polynucleotides encoding the Carnitine Carrier Related Protein-1 (CCRP-1) protein, fragments thereof, and the regulatory regions located at the 5'- and 3'-end of the CCRP-1 gene. The invention also concerns polypeptides encoded by the CCRP-1 gene and fragments thereof. The invention is further directed to methods of making said polynucleotides and polypeptides as well as methods of using the same. The invention also relates to antibodies directed specifically against the above polypeptides and to methods of using said antibodies to purify and detect the above polypeptides and to detect mitochondrion organelles.

BACKGROUND OF THE INVENTION

The majority of mitochondrial proteins are encoded by nuclear genes, are synthesized on cytosolic ribosomes, and are imported into the mitochondria. Nuclear-encoded proteins which are destined for the mitochondrial matrix typically contain positively-charged amino terminal signal sequences. Import of these preproteins from the cytoplasm requires a multisubunit protein complex in the outer membrane known as the translocase of outer mitochondrial membrane (TOM; previously designated MOM; Pfanner, N. et al., 1996) and at least three inner membrane proteins which comprise the translocase of inner mitochondrial membrane (TIM; previously designated MIM; Pfanner et al, supra). An inside-negative membrane potential across the inner mitochondrial membrane is also required for preprotein import. Preproteins are recognized by surface receptor components of the TOM complex and are translocated through a proteinaceous pore formed by other TOM components. Proteins targeted to the matrix are then recognized by the import machinery of the TIM complex. The import systems of the outer and inner membranes can function independently (Segui-Real, B. et al., 1993). Three TIM proteins have been identified in the yeast Saccharomyces cerevisiae. TIM44 is a hydrophilic protein which is peripherally associated with the inner face of the inner mitochondrial membrane. TIM23 and TIM17 are integral membrane proteins which are thought to comprise the core subunits of the inner membrane translocation channel. (Bomer, U. et al., 1996). Depletion of TIM17 (also known as MIM17, Mpi2, and Sms1; Pfanner et al., supra) causes defects in the import of several mitochondrial proteins (Ryan, K. R. et al., 1994). Furthermore, TIM44, TIM23, and TIM17 proteins are among the few known proteins essential for yeast viability (Maarse, A. C. et al. 1994; Ryan et al., supra).

Fatty acids are activated on the outer mitochondria membrane, whereas they are oxidized in the mitochondria matrix. Long chain acyl CoA molecules do not readily traverse the inner mitochondrial membrane, and so a special transport mechanism is needed. Activated long-chain fatty acids are carried across the inner mitochondrial membrane by carnitine zwitterionic compound formed from lysine. The acyl group is transferred from the sulfur atom of CoA to the hydroxyl group of carnitine to form acyl carnitine. This reaction is catalyzed by carnitine acyltransferase I, which is located on the cytosolic face of the inner mitochondrial membrane. Acyl carnitine is then shuttled across the inner mitochondrial membrane by a translocase. The acyl group is transferred back to CoA on the matrix side of the membrane. This reaction, which is catalyzed by carnitine acyltransferase II, is thermodynamically feasible because the O-acyl link in carnitine has a high group-transfer potential. Finally, carnitine is returned to the cytosolic side by the translocase, in exchange for an incoming acylcarnitine. A defect in the transferase or translocase, or a deficiency of carnitine, might be expected to impair the oxidation of long-chain fatty acids.

Uncoupling proteins, such as UCP-1 (thermogenin), are transmembrane proton-translocating proteins present in the mitochondria of brown adipose tissue, a specialized tissue which functions in heat generation and energy balance (Nicolls, D. G., and Locke, R. M., 1984; Rothwell, N. J. and Stock, M. J. 1979). Mitochondrial oxidation of substrates is accompanied by proton transport out of the mitochondrial matrix, creating a transmembrane proton gradient. Re-entry of protons into the matrix via ATP synthase is coupled to ATP synthesis. However, UCP-1 functions as a transmembrane proton transporter, permitting re-entry of protons into the mitochondrial matrix unaccompanied by ATP synthesis. Environmental exposure to cold evokes neural and hormonal stimulation of brown adipose tissue, which increases UCP mediated proton transport, brown fat metabolic activity, and heat production.

Recent studies with transgenic models indicate that brown fat and UCP-1 have an important role in energy expenditure in rodents. Transgenic mice in which brown adipocyte tissue was ablated by a toxin coupled to the UCP-promoter developed obesity and diabetes (Lowell, B. B., et al., 1993). Obesity in these transgenic animals developed in the absence of hyperphagia, suggesting that the uncoupled mitochondrial respiration of brown fat is an important component of energy expenditure. In a separate transgenic mouse model, ectopic expression of UCP-1 in white adipose tissue of genetically-obese mice led to a significant reduction in body weight and fat stores (Kopecky J., et al. 1995). These studies indicate that activity of UCP-1 is accompanied by energy expenditure and weight loss in rodents. Two other UCP proteins have recently been cloned. The first uncoupling protein-like protein (UCPL) or UCP-2, is expressed in multiple tissues, and is enriched in tissues of the lymphoid lineage (Fleury, C., et al., 1997). The second, UCP-3, is predominantly localized to skeletal muscle (Boss, O., et al., 1997). UCP-3 has been found to be regulated by cold and thyroid hormone (Larkin, S., et al., 1997).

Thermogenic protein activity, such as that found with UCP-1, may be useful in reducing, or preventing the development of excess adipose tissue, such as that found in obesity. Obesity is becoming increasingly prevalent in developed societies. Attempts to reduce food intake, or to decrease hypernutrition, are usually fruitless in the medium term because the weight loss induced by dieting results in both increased appetite and decreased energy expenditure (Leibel et al. 1995). The intensity of physical exercise required to expend enough energy to materially lose adipose mass is too great for many obese people to undertake on a sufficiently frequent basis. Thus, obesity is currently a poorly treatable, chronic, essentially intractable metabolic disorder. In addition obesity carries a serious risk of co-morbidities including, Type 2 diabetes, increased cardiac risk, hypertension, atherosclerosis, degenerative arthritis, and increased incidence of complications of surgery involving general anesthesia.

SUMMARY OF THE INVENTION

The present invention provides isolated CCRP-1 polynucleotides and polypeptides. One aspect of the invention provides isolated nucleic acid molecules comprising or alternatively consisting of polynucleotides having a nucleotide sequence selected from the group consisting of: (a) a polynucleotide comprising the nucleotide sequence of SEQ ID NO:1; (b) a polynucleotide comprising the nucleotide sequence of the human cDNA contained in the deposited clone; (c) a polynucleotide comprising a portion of the nucleotide sequence of SEQ ID NO:1 coding for a mature CCRP-1 polypeptide; (d) a polynucleotide comprising a nucleotide sequence of the portion of the human cDNA contained in the deposited clone coding for a mature CCRP-1 polypeptide; (e) a polynucleotide comprising a nucleotide sequence coding for the amino acid sequence of the full length polypeptide of SEQ ID NO:2; (f) a polynucleotide comprising a nucleotide sequence coding for an amino acid sequence of a mature polypeptide of SEQ IDNO:2; (g) a polynucleotide comprising a nucleotide sequence coding for an amino acid sequence of a full length CCRP-1 polypeptide encoded by the human cDNA contained in the deposited clone; (h) a polynucleotide comprising a nucleotide sequence coding for an amino acid sequence of a mature CCRP-1 polypeptide encoded by the human cDNA contained in the deposited clone; (i) a polynucleotide comprising a genomic sequence coding for a CCRP-1 polypeptide; (j) a polynucleotide comprising the 5' transcriptional regulatory region of the CCRP-1 gene; (k) a polynucleotide comprising the 3' transcriptional regulatory region of the CCRP-1 gene; (l) a polynucleotide comprising the nucleotide sequence of any combination of (i)–(k); (m) a polynucleotide comprising a nucleotide sequence of (a)–(l), wherein the polynucleotide is single stranded, double stranded, or a portion is single stranded and a portion is double stranded; (n) a polyncleotide comprising a nucleotide sequence complementary to any of the single stranded polynucleotides of (m). The invention further provides for fragments of the nucleic acid molecules of (a)–(n) above.

Further embodiments of the invention include isolated nucleic acid molecules that comprise, or alternatively consist of, a polynucleotide having a nucleotide sequence at least 90% identical, and more preferably at least 95%, 96%, 97%, 98% or 99% identical, to any of the nucleotide sequences in (a)–(n) above, or a polynucleotide which hybridizes under stringent hybridization conditions to a polynucleotide in (a)–(n) above. Additional nucleic acid embodiments of the invention relate to isolated polynucleotides comprising a nucleotide sequence coding for an amino acid sequence of an epitope-bearing portion of a CCRP-1 polypeptide.

The present invention also relates to recombinant vectors, which include the isolated polynucleotides of the present invention, and to host cells recombinant for the polynucleotides of the present invention, as well as to methods of making such vectors and host cells. The present invention further relates to the use of these recombinant vectors and recombinant host cells in the production of CCRP-1 polypeptides.

The invention further provides for isolated CCRP-1 polypeptides comprising an amino acid sequence selected from the group consisting of: (a) the full length amino acid sequence of SEQ ID NO:2; (b) the amino acid sequence of a full length CCRP-1 polypeptide encoded by the human cDNA contained in the deposited clone; (c) an amino acid sequence of the portion of SEQ ID NO:2 representing a mature CCRP-1 polypeptide; (d) an amino acid sequence of a mature CCRP-1 polypeptide encoded by the human cDNA contained in the deposited clone; (e) an amino acid sequence of a signal peptide of SEQ ID NO:2; (f) an amino acid sequence of a signal peptide portion of a CCRP-1 polypeptide encoded by the human cDNA contained in the deposited clone; (g) an amino acid sequence of an epitope-bearing portion of SEQ ID NO:2; (h) an amino acid sequence of an epitope-bearing portion of a CCRP-1 polypeptide encoded by the human cDNA clone contained in the deposited clone. The invention further provides for fragments of the polypeptides of (a)–(h) above, such as those having biological activity or comprising biologically functional domain(s).

The polypeptides of the present invention also include polypeptides having an amino acid sequence with at least 70% similarity, and more preferably at least 75%, 80%, 85%, 90%, 95%, 96%, 97%, 98%, or 99% similarity to those polypeptides described in (a)–(h) above, as well as polypeptides having an amino acid sequence at least 70% identical, more preferably at least75% identical, and still more preferably 80%, 85%, 90%, 95%, 96%, 97%, 98%, or 99% identical to those polypeptides in (a)–(h) above. The invention further relates to methods of making the polypeptides of the present invention.

The invention further relates to antibodies that specifically bind the CCRP-1 polypeptides of the present invention and to methods for producing such antibodies and fragments thereof.

The invention also provides for methods of detecting the presence of the polynucleotides and polypeptides of present invention in a biological sample. One such method involves assaying for the expression of a CCRP-1 polynucleotide in a sample from an animal. An example of such a method involves the use of the polymerase chain reaction (PCR) to amplify and detect CCRP-1 polynucleotides or Southern and Northern blot hybridization to detect CCRP-1 genomic DNA, cDNA or mRNA. Another example of such a method of detecting one or more CCRP-1 polynucleotides in a biological sample comprises the steps of: (a) contacting the biological sample with one or more polynucleotides of the present invention (which may be individually specified), under conditions such that hybridization occurs, and (b) detecting hybridization of said polynucleotides with one or more CCRP-1 polynucleotides present in the biological sample.

The invention also concerns to biallelic markers of the CCRP-1 gene and the use thereof. The invention is further directed to methods for the screening of substances or molecules that inhibit the expression of CCRP-1, as well as with methods for the screening of substances or molecules that interact with a CCRP-1 polypeptide or that modulate the activity of a CCRP-1 polypeptide (either increase or decrease activity).

The present invention further relates to methods of detecting mitochondria by using antibodies which specifically bind the polypeptides of the present invention or by fusing a polypeptide of the present invention, comprising the CCRP-1 mitochondrial signal peptide sequence, or position thereof to either a heterologous polypeptide that can be used as a label directly (e.g., green fluorescent protein) or to a heterologous polypeptide specifically recognized by an antibody that can be used in an immunodetection assay.

The present invention further relates to methods of delivering heterologous polynucleotides to mitochondria by fusing or linking (covalently or non-covalently) the heterologous polynucleotide of interest to a composition comprising a CCRP-1 mitochondrial signal peptide sequence (−68 to −1 of SEQ ID NO:2 or the signal peptide sequence of a polypeptide encoded by human cDNA of the deposited clone) or portions thereof.

The present invention further relates to methods of delivering small molecules, such as bioactive or mitotoxic compounds (e.g., DNP, lipophillic cations), to mitochondria by linking the small molecule to a composition comprising a CCRP-1 mitochondrial signal peptide sequence (−68 to −1 of SEQ ID NO:2 or the signal peptide sequence of a polypeptide encoded by human cDNA of the deposited clone) or portions thereof.

The present invention further relates to methods of delivering heterologous polypeptides to mitochondria by fusing the heterologous polypeptide of interest to polypeptides of the present invention comprising the CCRP-1 mitochondrial signal peptide sequence (−68 to −1 of SEQ ID NO:2 the signal peptide sequence of a polypeptide encoded by human cDNA of the deposited clone or portions of either).

The present invention further relates to methods of increasing the permeability of mitochondria, thereby causing the nonspecific inhibition of mitochondrial enzymes leading to a decrease in ATP production, and alternatively cell death, comprising administering to in vitro cell cultures or an animal a composition comprising a polypeptide of the present invention, wherein the polypeptide comprises a CCRP-1 mitochondrial signal peptide sequence or portion thereof.

The present invention further relates to insect, bird, plant and mammalian cells with an enhanced ability to metabolize fatty acids, wherein the cells are transiently or stably transfected or transduced with a polynucleotide that expresses a polypeptide of the present invention.

The present invention further relates to a transgenic plant or animal, preferably mammals, fish, and birds, more preferably, a mouse, rat, horse, cow, pig, sheep, chicken, dog, cat, wherein the animal is transgenic for a polynucleotide of the present invention and expresses a polypeptide of the present invention.

The present invention further relates to a method for enhancing a cells ability to metabolize,grow or be maintained under conditions where the fatty acids are present, preferably at levels higher than normal.

The present invention further relates to a device, physiological acceptable composition and method for metabolizing fatty acids in an animal or individual (host) thereby reducing an individual's blood levels of fatty acids and alternatively, in addition, reducing the level of, or reducing the increase in, white adipose tissue. More particularly, the inventive device is an extracorporeal device for metabolizing fatty acids comprising a semipermeable membrane having a first and a second side and having a molecular weight cutoff of at least 10,000 daltons, an oxidizing component located adjacent to the first side of the semipermeable membrane comprising an enzyme system with necessary cofactors, brown fat mitochondria or whole cell cultures of brown adipose cells of any species or cells transfected with a construct comprising a CCRP-1 polynucleotide sequence alone or combined with a heterologous uncoupling protein (UCP) polynucleotide sequence, referred to hereafter as CCRP-1/UCP, each regulated by an appropriate promoter sequence (e.g., MMTV, SV40, CMV intermediate early, etc.), either combined on a single vector or on separate vectors, wherein the oxidizing component is capable of oxidizing fatty acids, and a means for circulating blood from the host to the second side of the semipermeable membrane for triglyceride hydrolysis and diffusion of free fatty acids to the first side of the semipermeable membrane for oxidation of fatty acids and returning treated blood to the host. Preferably, the oxidizing component comprises a culture of brown fat cells or other eukaryotic cells transfected with a gene encoding a CCRP-1 polypeptide or CCRP-1/UCP polypeptide(s) in an expression vector. Preferably the semipermeable membrane has a lipoprotein lipase embedded therein.

The present invention further provides a physiologically acceptable composition for metabolizing fatty acids comprising a culture of brown fat cells or CCRP-1 or CCRP-1/UCP transfected cells encapsulated in a porous growth matrix and having a semipermeable membrane encapsulating the porous growth matrix. The semipermeable membrane has a molecular weight cutoff of at least 10,000 daltons and, preferably, a lipoprotein lipase embedded therein. Preferably, the semipermeable membrane comprises a tubular membrane having two ends, filled with brown fat cells in the porous growth matrix and sealed at both ends prior to subcutaneous, intramuscularor, or intraperitoneal implantation. Preferably the porous growth matrix comprises alginate beads or another complex polysaccharide porous matrix suitable for cellular growth and metabolism.

The present invention further provides a physiologically acceptable composition for metabolizing fatty acids comprising a mammalian cell stably transfected with a DNA sequence(s) coding for a CCRP-1 or CCRP-1/UCP polypeptides, wherein the transfected mammalian cell transcribes and translates the CCRP-1 or CCRP-1/UCP polypeptides. Preferably, the transfected mammalian cell further comprises a cDNA sequence that confers antibiotic sensitivity to the mammalian cell as a "suicide gene" mechanism to remove the transformed mammalian cell from an individual if treated with said composition. Most preferably, the antibiotic is gancyclovir.

The present invention further provides a physiologically acceptable composition for metabolizing fatty acids comprising a cDNA sequence encoding a CCRP-1 or CCRP-1/UCP polypeptide(s) in combination with appropriate regulatory and promoter sequences, wherein said cDNA sequence(s) is taken up into hosts cells, in vivo or in vitro, and is translated into CCRP-1 or CCRP-1/UCP polypeptide (s).

The present invention further provides a physiologically acceptable composition for metabolizing fatty acids comprising a culture of allogeneic brown fat cells transfectd or transduced to express a CCRP-1 or CCRP-1/UCP polypeptide(s), wherein the brown fat cells are maintained or proliferated ex vivo.

Further still, the present invention provides a method for maintaining a lower percentage of white adipose tissue than normal or effecting weight loss in a host, wherein the lean state or weight loss is due to prevention of accumulation, or loss, of white adipose tissue, with minimal loss of muscle mass, wherein the method for maintaining a lean state or effecting weight loss comprises administration of an effective amount of a physiologically acceptable composition described herein in sufficient amounts to metabolize at least 25, preferably at least 55 calories or 25 g per day, preferably at least 65 g per day of fatty acids and in some embodiments more than 65 g per day.

The invention further relates to methods of screening and identifying individuals at increased risk for developing certain diseases/disorders, including hyperinsulinemia, glucose intolerance, type II diabetes, obesity, syndrome X, immunological dysfunction and body temperature dysfunction, and heart disease.

The present invention also relates to methods of identifying individuals having elevated or reduced levels of CCRP-1, which individuals are likely to benefit from therapies to suppress or enhance CCRP-1 expression, respectively.

The present invention also relates to methods of screening compounds for their ability to modulate (e.g. increase or inhibit) the activity or expression of CCRP-1. More specifically, the present invention relates to methods of testing compounds for ability either to increase or to decrease expression or activity of CCRP-1.

The present invention also relates to pharmaceutical or physiologically acceptable compositions comprising, an active agent, the polypeptides, polynucleotide or antibodies of the present invention.

The present invention further relates to methods of reducing fatty acid blood levels and treating diseases/disorders such as hyperinsulinemia, glucose intolerance, diabetes, obesity, syndrome X, heart disease, cancer and hypothermia by increasing CCRP-1 activity and/or expression.

The present invention further relates to methods of reducing fatty acid blood levels and treating diseases/disorders such as hyperinsulinemia, glucose intolerance, diabetes, obesity, syndrome X, heart disease, cancer and hypothermia by increasing CCRP-1 activity and/or expression.

BRIEF DESCRIPTION OF THE SEQUENCE LISTING

Figure 1A:
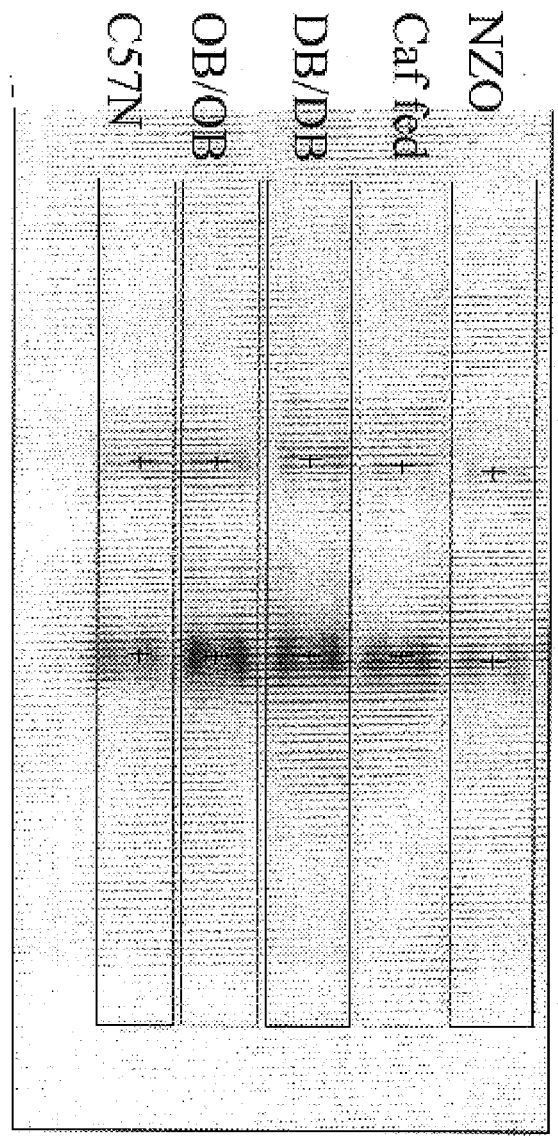
FIG. 1. Differential expression of CCRP in obese mouse models. Blots were prepared containing 1 µg of polyA+-enriched RNA from livers of normal lean C57N mice (lane 1), and the following obese mice : ob/ob (lane 2), db/db (lane 3), C57N mice on a high-fat cafeteria fed diet (lane 4), and New Zealand Obese (lane 5) mice. The Northern blot was probed with an antisense RNA probe to the CCRP according to the Novagen protocol (catalog No. 69256-3). The blot was then washed under high stringency conditions, and exposed on a Phosphorimager screen (Molecular Dynamics). The screen was scanned on a Phosphorimager, and the image is shown in FIG. 1A.
FIGS. 1B and 1C show the relative levels of expression in graphic (FIG. 1B) and tabular (FIG. 1C) form.

SEQ ID NO:1 represents the cDNA sequence of CCRP-1.

SEQ ID NO:2 represents the amino acid sequence encoded by the cDNA of SEQ ID No:1.

DETAILED DESCRIPTION

The present invention pertains to the Carintine Carrier Related Protein-1 (CCRP-1). CCRP-1 is protein expressed by a nuclear gene but believed transported to mitochondria as a mitochondrial membrane bound protein. CCRP-1 is further believed to act functionally as either a carnitine/acylcarnitine translocase or as an uncoupling protein. In either case, CCRP-1 is involved in the metabolism of fatty acids.

The present invention concerns polynucleotides and polypeptides related to the CCRP-1 gene. Oligonucleotide probes and primers hybridizing specifically with a genomic or a cDNA sequence of CCRP-1 are also part of the invention. A further object of the invention consists of recombinant vectors comprising any of the nucleic acid sequences described in the present invention, and in particular recombinant vectors comprising a regulatory region of CCRP-1 or a sequence encoding the CCRP-1 protein, as well as cell hosts recombinant for said nucleic acid sequences or recombinant vectors. The invention also encompasses methods of screening of molecules which inhibit the expression of the CCRP-1 gene or which modulate the activity of the CCRP-1 protein. The invention also deals with antibodies directed specifically against such polypeptides that are useful as agonists, antagonists or as diagnostic detection reagents. Definitions:

Before describing the invention in greater detail, the following definitions are set forth to illustrate and define the meaning and scope of the terms used to describe the invention herein.

The terms "CCRP-1 gene", when used herein, encompasses genomic, mRNA and cDNA sequences encoding the CCRP-1 protein, including the untranslated regulatory regions of the genomic DNA, although each may be specified.

The term "heterologous", when used herein, is intended to designate any polypeptide or polynucleotide other than a CCRP-1 polypeptide or polynucleotide of the present invention.

The term "isolated" requires that the material be removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. Specifically excluded from the definition of "isolated" are: naturally occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies, and/or further wherein the polynucleotide of the present invention makes up less than 5% (or alternatively 1%, 2%, 3%, 4%, 10%, 25%, 50%, 75%, or 90%, 95, or 99%) of the number of nucleic acid inserts in the vector molecules. Further specifically excluded are whole cell genomic DNA or whole cell RNA preparations (including said whole cell preparations which are mechanically sheared or enzymaticly digested). Further specifically excluded are the above whole cell preparations as either an in vitro preparation or as a heterogeneous mixture separated by electrophoresis (including blot transfers of the same) wherein the polynucleotide of the invention have not been further separated from the heterologous polynucleotides in the electrophoresis medium (e.g., further separating by excising a single band from a heterogeneous band population in an agarose gel or nylon blot).

As used herein, the term "purified" does not require absolute purity; rather, it is intended as a relative definition. Purification of starting material or natural material is at least one order of magnitude, preferably two or three orders, and more preferably four or five orders of magnitude is expressly contemplated. As an example, purification from 0.1% concentration to 10% concentration is two orders of magnitude.

To illustrate, individual cDNA clones isolated from a cDNA library have been conventionally purified to electrophoretic homogeneity. The sequences obtained from these clones could not be obtained directly either from the library or from total human DNA. The cDNA clones are not naturally occurring as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^4$–$10^6$ fold purification of the native message.

The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or hetero-dimers, trimers, etc. The term "purfied" may also be used to specify the separation of covalently closed polynucleotides from linear polynucleotides. A polynucleotide is substantially pure when at least about 50%, preferably 60 to 75% of a sample exhibits a single polynucleotide sequence and conformation (linear versus covalently close). A substantially pure polypeptide or polynucleotide typically comprises about 50%, preferably 60 to 90% weight/weight of a polypeptide or polynucleotide sample, respectively, more usually about 95%, and preferably is over about 99% pure. Polypeptide and polynucleotide purity, or homogeneity, is indicated by a number of means well known in the art, such as agarose or polyacrylamide gel electrophoresis of a sample, followed by visualizing a single band upon staining the gel. For certain purposes higher resolution can be provided by using HPLC or other means well known in the art. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

As used herein, the term "recombinant polynucleotide" means that the cDNA is adjacent to "backbone" nucleic acid to which it is not adjacent in its natural environment. Additionally, to be "enriched" the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousanth position, e.g., thousanth) # of the number of nucleic acid inserts in the population of recombinant backbone molecules. Unless otherwise specified, nucleotides and amino acids of polynucleotide and polypeptide fragments (respectively) of the present invention are contiguous and not interrupted by heterologous sequences.

The term "polypeptide" refers to a polymer of amino acids without regard to the length of the polymer; thus, "peptides," "oligopeptides", and "proteins" are included within the definition of polypeptide and used interchangeably herein. This term also does not specify or exclude chemical or post-expression modifications of the polypeptides of the invention, although chemical or post-expression modifications of these polypeptides may be included excluded as specific embodiments. Therefore, for example, modifications to polypeptides that include the covalent attachment of glycosyl groups, acetyl groups, phosphate groups, lipid groups and the like are expressly encompassed by the term polypeptide. Further, polyeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxlation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS-STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12, 1983; Seifter et al., Meth Enzymol 182:626–646, 1990; Rattan et al., Ann NY Acad Sci 663:48–62, 1992, the disclosures of which are incorporated herein by reference in their entireties). Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring. The term "polypeptide" may also beused interchangeably with the term "protein".

As used herein, the term "non-human animal" refers to any non-human animal, including insects, birds, rodents and more usually mammals. Preferred non-human animals include: primates; farm animals such as swine, goats, sheep, donkeys, cattle, horses, chickens, rabbits; and rodents, preferably rats or mice. As used herein, the term "animal" is used to refer to any species in the animal kingdom, preferably vertebrates, including birds and fish, and more preferable a mammal. Both the terms "animal" and "mammal" expressly embrace human subjects unless preceded with the term "non-human".

As used interchangeably herein, the terms "nucleic acid molecule", "oligonucleotides", and "polynucleotides" include RNA or, DNA (either single or double stranded, coding, complementary or antisense), or RNA/DNA hybrid sequences of more than one nucleotide in either single chain or duplex form (although each of the above species may be particularly specified). The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylamino-methyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine. Methylenemethylimino linked oligonucleosides, as well as mixed backbone compounds, may be prepared as described in U.S. Pat. Nos. 5,378,825; 5,386,023; 5,489,677; 5,602,240; and 5,610,289 ,the disclosures of which are incorporated herein by reference in their entireties. Formacetal and thioformacetal linked oligonucleosides may be prepared as described in U.S. Pat. Nos. 5,264,562 and 5,264,564, the disclosures of which are incorporated herein by reference in their entireties. Ethylene oxide linked oligonucleosides may be prepared as described in U.S. Pat. No. 5,223,618, the disclosure of which is incorporated herein by reference in its entirety. Phosphinate oligonucleotides may be prepared as described in U.S. Pat. No. 5,508,270, the disclosure of which is incorporated herein by reference in its entirety. Alkyl phosphonate oligonucleotides may be prepared as described in U.S. Pat. No. 4,469,863, the disclosure of which is incorporated herein by reference in its entirety. 3'-Deoxy-3'-methylene phosphonate oligonucleotides may be prepared as described in U.S. Pat. No. 5,610,289 or U.S. Pat. No. 5,625,050, the disclosures of which are incorporated herein by reference in their entireties. Phosphoramidite oligonucleotides may be prepared as described in U.S. Pat. No. 5,256,775 or U.S. Pat. No. 5,366,878, the disclosures of which are incorporated herein by reference in their entireties. Alkylphosphonothioate oligonucleotides may be prepared as described in published PCT applications WO 94/17093 and WO 94/02499, the disclosures of which are incorporated herein by reference in their entireties. 3'-Deoxy-3'-amino phosphoramidate oligonucleotides may be prepared as described in U.S. Pat. No. 5,476,925, the disclosure of which is incorporated herein by reference in its entirety. Phosphotriester oligonucleotides may be prepared as described in U.S. Pat. No. 5,023,243, the disclosure of which is incorporated herein by reference in its entirety. Borano phosphate oligonucleotides may be prepared as described in U.S. Pat. Nos. 5,130,302 and 5,177,198, the disclosures of which are incorporated herein by reference in their entireties.

The terms "comprising", "consisting of" and "consisting essentially of" may be interchanged for one another throughout the instant application". The term "having" has the same meaning as "comprising" and may be replaced with either the term "consisting of" or "consisting essentially of".

"Stringent", "moderate," and "low" hybridization conditions are as defined below.

The term "capable of hybridizing to the polyA tail of said mRNA" refers to and embraces all primers containing stretches of thymidine residues, so-called oligo(dT) primers, that hybridize to the 3' end of eukaryotic poly(A)+ mRNAs to prime the synthesis of a first cDNA strand. Techniques for generating said oligo (dT) primers and hybridizing them to mRNA to subsequently prime the reverse transcription of said hybridized mRNA to generate a first cDNA strand are well known to those skilled in the art and are described by (John Wiley and Sons, Inc., 1997, and Sambrook et al. 1989, the entire disclosures of which are incorporated herein by reference). Preferably, said oligo (dT) primers are present in a large excess in order to allow the hybridization of all mRNA 3' ends to at least one oligo(dT) molecule. The priming and reverse transcription steps are preferably performed between 37° C. and 55° C. depending on the type of reverse transcriptase used.

A sequence which is "operably linked" to a regulatory sequence such as a promoter means that said regulatory element is in the correct location and orientation in relation to the nucleic acid to control RNA polymerase initiation and expression of the nucleic acid of interest.

As used herein, the term "operably linked" refers to a linkage of polynucleotide elements in a functional relationship. For instance, a promoter or enhancer is operably linked to a coding sequence if it affects the transcription of the coding sequence.

The terms "trait" and "phenotype" are used interchangeably herein and refer to any visible, detectable or otherwise measurable property of an organism such as symptoms of, or susceptibility to a disease for example. Typically the terms "trait" or "phenotype" are used herein to refer to symptoms of, or susceptibility to a disease, a beneficial response to or side effects related to a treatment. Preferably, said trait can be, without to be limited to, cancers, developmental diseases, and neurological diseases.

The term "allele" is used herein to refer to variants of a nucleotide sequence. A biallelic polymorphism has two forms. Diploid organisms may be homozygous or heterozygous for an allelic form. Unless otherwise specified, the polynucleotides of the present invention encompass allelic variants of the CCRP-1 gene.

The term "upstream" is used herein to refer to a location that is toward the 5' end of the polynucleotide from a specific reference point.

The terms "base paired" and "Watson & Crick base paired" are used interchangeably herein to refer to nucleotides which can be hydrogen bonded to one another by virtue of their sequence identities in a manner like that found in double-helical DNA with thymine or uracil residues linked to adenine residues by two hydrogen bonds and cytosine and guanine residues linked by three hydrogen bonds (See e.g., Stryer, L. 1995).

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind.

The term "deposited clone" is used herein to refer to Genset internal designation 117-005-4-0-E5-FLC.

The term "clone 117-005-4-0-E5-FLC" is used herein to refer to the nucleic acid of SEQ ID NO:1.

Polynucleotides

The present invention concerns the genomic and cDNA sequence of CCRP-1. The present invention encompasses the CCRP-1 gene, or polynucleotides comprising the CCRP-1 genomic or cDNA sequence, as well as fragments and variants thereof. These polynucleotides may be purified, isolated, and/or recombinant. The expression of the CCRP-1 gene has been shown to lead to the production of at least one mRNA species, the nucleic acid sequence of which is set forth in SEQ ID NO:1 Another object of the invention, therefore, is a purified, isolated, or recombinant polynucleotide comprising the nucleotide sequence of SEQ ID NO:1 complementary sequences thereto, as well as fragments thereof. Moreover, preferred polynucleotides of the invention include purified, isolated, or recombinant CCRP-1 cDNAs consisting of, consisting essentially of, or comprising the sequence of SEQ ID NO:1. Also provided in the present invention are allelic variants, orthologs, splice variants, and/or species homologs of the CCRP-1 gene. Procedures known in the art can be used to obtain full-length genes and cDNAs, allelic variants, splice variants, full-length coding portions, orthologs, and/or species homologs of genes and cDNAs corresponding to SEQ ID NO:1 or the deposited clone, clone ID 117-005-4-0-E5-FLC using information from the sequences disclosed herein or the clone deposited with the ATCC. For example, allelic variants and/or species homologs may be isolated and identified by making suitable probes or primers from the sequences provided herein and screening a suitable nucleic acid source for allelic variants and/or the desired homologue. In specific embodiments, the polynucleotides of the invention are at least 15, at least 30, at least 50, at least 100, at least 125, at least 500, at least 1000, at least 1200, at least 1500, at least 1600, at least 1700 or at least 1725 continuous nucleotides but are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 naturally occurring genomic flanking gene(s).

Mitochondrial Signal Sequences and Mature Sequences

The present invention also encompasses polynucleotides encoding mature forms of the CCRP-1 polypeptide having the polypeptide sequence from +1 to 240 of SEQ ID NO:2 and/or a mature polypeptide sequence encoded by the cDNA in clone 117-005-4-0-E5-FLC. Polynucleotides encoding the mature forms (such as, the polynucleotide sequence in SEQ ID NO:1 and/or the polynucleotide sequence contained in the cDNA of clone 117-005-4-0-E5-FLC) are also encompassed by the invention.

The predicted mitochondrial signal peptide of the CCRP-1 is from amino acid residues −68 to −1 of SEQ ID NO:2. As one of ordinary skill would appreciate, however, cleavage sites sometimes vary from organism to organism and cannot be predicted with absolute certainty. Accordingly, the present invention provides for polynucleotides encoding mitochondrail directed polypeptides having a sequence shown in SEQ ID NO:2 which have an N-terminus beginning within 5 residues (i.e., + or −5 residues) of the predicted cleavage point. Similarly, it is also recognized that in some cases, cleavage of the signal sequence from a secreted protein is not entirely uniform, resulting in more than one secreted species either in the same or different cell types. These polypeptides, and the polynucleotides encoding such polypeptides, are contemplated by the present invention. Moreover, the mitochondrial signal sequence identified by the above analysis may not necessarily predict the naturally occurring signal sequence. For example, the naturally occurring signal sequence may be further upstream or downstream from the predicted signal sequence. However, it is believed that the predicted signal sequence will be capable of directing the CCRP-1 protein to the mitochondria. Nonetheless, the present invention provides for polynucleotides encoding the mature protein produced by expression of the polynucleotide sequence of SEQ ID NO:1 and/or the polynucleotide sequence contained in the human cDNA of clone 117-005-4-0-E5-FLC, in a mammalian cell. These polypeptides and the polynucleotides encoding such polypeptides are contemplated by the present invention.

Polynucleotide Variants and Fragments

The invention also relates to variants and fragments of the polynucleotides described herein. Variants of polynucleotides, as the term is used herein, are polynucleotides that differ from a reference polynucleotide. A variant of a polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms. Generally, differences are limited so that the nucleotide sequences of the reference and the variant are closely similar overall and, in many regions, identical. In addition to the isolated nucleic acid molecule of SEQ ID NO:1 and fragments thereof, the invention further includes polynucleotides which comprise a sequence substantially different from those described above but which, due to the degeneracy of the genetic code, still encode CCRP-1 polypeptides of the present invention. That is, all possible polynucleotide sequences that encode the CCRP-1 polypeptides of the present invention are completed. This includes the genetic code and species-specific codon preferences known in the art. Thus, it would be routine for one skilled in the art to generate the degenerate variants described above, for instance, to optimize codon expression for a particular host (e.g., change codons in the human mRNA to those preferred by other mammalian or bacterial host cells). The invention further provides isolated nucleic acid molecules having the nucleotide sequence complementary to SEQ ID NO:1 or a fragment thereof. Such isolated molecules, particularly DNA molecules, are useful as probes for gene mapping and for identifying CCRP-1 mRNA in a biological sample, for instance, by PCR or Northern blot analysis.

The present invention is further directed to polynucleotides encoding portions or fragments of the polypeptides described herein. Uses for the polynucleotide fragments of the present invention include probes, primers, molecular weight markers and for expressing the polypeptide fragments of the present invention. Fragments include portions of polynucleotides of SEQ ID NO:1, of the genomic CCRP-1 gene sequence, of polynucleotides encoding the polypeptide of SEQ ID NO:2, of the human cDNA in clone 117-005-4-0-E5-FLC, and of polynucleotides encoding the CCRP-1 polypeptides encoded by the human cDNA of clone 117-005-4-0-E5-FLC. Particularly included in the present invention is a purified or isolated polynucleotide comprising at least 8 consecutive bases of a polynucleotide of the present invention. In one aspect of this embodiment, the polynucleotide comprises at least 10, 12, 15, 18, 20, 25, 28, 30, 35, 40, 50, 75, 100, 150, 200, 300, 400, 500, 600, 700, 800, 900, 1000, 1100, 1200, 1300, 1400, or 1500 consecutive nucleotides of a polynucleotide of the present invention.

In addition to the above preferred nucleic acid sizes, further preferred sub-genuses of nucleic acids comprise at least 8 nucleotides, wherein "at least 8" is defined as any integer between 8 and the integer representing the 3' most nucleotide position as set forth in the sequence listing or elsewhere herein. Further included as preferred polynucleotides of the present invention are nucleic acid fragments at least 8 nucleotides in length, as described above, that are further specified in terms of their 5' and 3' position. The 5' and 3' positions are represented by the position numbers set forth in the sequence listing below. For allelic and degenerate and other variants, position 1 is defined as the 5' most nucleotide of the ORF, i.e., the nucleotide "A" of the start codon (ATG) with the remaining nucleotides numbered consecutively. Therefore, every combination of a 5' and 3' nucleotide position that a polynucleotide fragment invention, at least 8 contiguous nucleotides in length, could occupy on a CCRP-1 polynucleotide of the present invention is included in the invention as an individual species. The polynucleotide fragments specified by 5' and 3' positions can be immediately envisaged and are therefore not individually listed solely for the purpose of not unnecessarily lengthening the specifications. It is noted that the above species of polynucleotide fragments of the present invention may alternatively be described by the formula "x to y"; where "x" equals the 5" most nucleotide position and "y" equals the 3" most nucleotide position of the polynucleotide; and further where "x" equals an integer between 1 and the number of nucleotides of the polynucleotide sequence of the present invention minus 8, and where "y" equals an integer between 9 and the number of nucleotides of the polynucleotide sequence of the present invention; and where "x" is an integer smaller then "y" by at least 8. The present invention also provides for the exclusion of any species of polynucleotide fragments of the present invention specified by 5' and 3' positions or sub-genuses of polynucleotides specified by size in nucleotides as described above. Any number of fragments specified by 5' and 3' positions or by size in nucleotides, as described above, may be excluded.

In another aspect, the invention provides an isolated nucleic acid molecule comprising a polynucleotide which hybridizes under stringent hybridization conditions to a polynucleotide of the present invention. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 ~mg/ml denatured, sheared salmon sperm DNA, followed by washing the filters in 0.1×SSC at about 65 degree C. Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH,P04; 0.02M EDTA, pH 7.4), 0.5% SDS, 30% formamide, 100 µg/ml salmon sperm blocking DNA; followed by washes at 50 degree C. with 1×SSPE,0.1% SDS. In addition, to achieve even lower stringency, washes performed following stringent hybridization can be done at higher salt concentrations (e.g. 5×25SSC). Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility. Of course, a polynucleotide which hybridizes only to polyA+ sequences (such as any 3' terminal polyA+ tract of a cDNA shown in the sequence listing), or to a 5 complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using digo dT as a primer).

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including for example, but not limited to non-coding 5' and 3' sequences, vector sequence, sequences used for purification, probing, or priming. For example, heterologous sequences include transcribed, nontranslated sequences that may play a role in transcription, and mRNA processing, for example, ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification of the fused polypeptide. In certain preferred embodiments of this aspect of the invention, the tag amino acid sequence is a hexa-histidine peptide, such as the tag provided in a pQE vector (QIAGEN, Inc., 9259 Eton Avenue, Chatsworth, Calif., 91311), among others, many of which are commercially available. For instance, hexa-histidine provides for convenient purification of the fusion protein (See Gentz et al., 1989). The "HA" tag is another peptide useful for purification which corresponds to an epitope derived from the influenza hemagglutinin protein (See Wilson et al., 1984). As discussed below other such fusion proteins include the CCRP-1 protein fused to Fc at the N- or C-terminus. As stated above, variants polynucleotides may occur naturally, such as a natural allelic variant, or by recombinant methods. By an "allelic variant" is intended one of several alternate forms of a gene occupying a given locus on a chromosome of an organism (See, e.g., B. Lewin, 1990). Non-naturally occurring variants may be produced using art-known mutagenesis techniques. Such nucleic acid variants include those produced by nucleotide substitutions, deletions, or additions. The substitutions, deletions, or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of a CCRP-1 protein of the present invention or portions thereof. Also preferred in this regard are conservative substitutions.

Such polypeptide variants include those produced by amino acid substitutions, deletions or additions. The substitutions, deletions, or additions may involve one or more residues. Alterations may produce conservative or non-conservative amino acid substitutions, deletions, or additions. Especially preferred among these are silent substitutions, additions and deletions, which do not alter the properties and activities of a CCRP-1 protein of the present invention or portions thereof. Also especially preferred in this regard are conservative substitutions.

The present invention also relates to recombinant vectors, which include the isolated polynucleotides of the present invention, and to host cells recombinant for a polynucleotide of the invention, such as the above vectors, as well as to methods of making such vectors and host cells and for using them for production of CCRP-1 polypeptides by recombinant techniques. The present application is further directed to polynucleotides at least 90%, 95%, 96%, 97%, 98% or 99% identical to the polynucleotide of SEQ ID NO:1 or the human CCRP-1 cDNA of clone 117-005-4-0-E5-FLC. The above polynucleotides are included regardless of whether they encode a polypeptide having fatty acid metabolizing, carnitine/acylcarnitine translocase, uncoupling, or mitochondrial signal peptide activity. This is because even where a particular nucleic acid molecule does not encode a polypeptide having activity, one of skill in the art would still know how to use the nucleic acid molecule, for instance, as a hybridization probe or primer. Uses of the nucleic acid molecules of the present invention that do not encode a polypeptide having CCRP-1 activity include, inter alia, isolating an CCRP-1 gene or allelic variants thereof from a DNA library, and detecting CCRP-1 mRNA expression in biological samples, suspected of containing CCRP-1 mRNA or DNA by Northern Blot or PCR analysis.

The present invention is further directed to nucleic acid molecules having sequences at least 50%, 60%, 70%, 80%, 90%, 95%, 96%, 97%, 98% or 99% identical to the polynucleotide of SEQ ID NO:1 and of clone 117-005-4-0-E5-FLC, which do, in fact, encode a polypeptide having CCRP-1 polypeptide activity. By "a polypeptide having CCRP-1 activity" is intended polypeptides exhibiting fatty acid metabolizing carnitine acylcamitine translocase, uncoupling, other mitochondrial carrier protein activity, or mitochondrial signal peptide activity similar, but not necessarily identical, to an activity of the mature CCRP-1 protein of the invention, as measured in a particular biological assay suitable for measuring activity of the specified protein. Of course, due to the degeneracy of the genetic code, one of ordinary skill in the art will immediately recognize that a large number of the nucleic acid molecules at least 50%, 60%, 70%, 80%, 90%, 95%, 96%, 97%, 98%, or 99% identical to nucleic acid sequences shown in SEQ ID NO:1 will encode a polypeptide having biological activity. In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having biological activity. This is because the skilled artisan is fully aware of amino acid substitutions that are either less likely or not likely to significantly effect protein function (e.g., replacing one aliphatic amino acid with a second aliphatic amino acid), as further described below. By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the CCRP-1 polypeptide. In other words, to obtain a polynucleotide having a nucleotide sequence at least 95% identical to a reference nucleotide sequence, up to 5% of the nucleotides in the reference sequence may be deleted, inserted, or substituted with another nucleotide. The query sequence may be an entire sequence shown in SEQ ID NO:1, the ORF (open reading frame), or any fragment specified as described herein.

The methods of determining and defining whether any particular nucleic acid molecule or polypeptide is at least 50%, 60%, 70%, 80%, 90%, 95%, 96%, 97%, 98% or 99% identical to a nucleotide sequence of the present invention can be done by using known computer programs. A preferred method for determining the best overall match between a query sequence (a sequence of the present invention) and a subject sequence, also referred to as a global sequence alignment, can be determined using the FASTDB computer program based on the algorithm of Brutlag et al., (See, e.g., Brutlag et al., 1990). In a sequence alignment the query and subject sequences are both DNA sequences. An RNA sequence can be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is 35 shorter. If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only nucleotides outside the 5' and 3' nucleotides of the subject sequence, as displayed by the FASTDB alignment, which are not matched/aligned with the query sequence, are calculated for the purposes of manually adjusting the percent identity score. For example, a 90-nucleotide subject sequence is aligned to a 100-nucleotide query sequence to determine percent identity. The deletions occur at the 5' end of the subject sequence and therefore, the FASTDB alignment does not show a matched/alignment of the first 10 nucleotides at 5' end. The 10 unpaired nucleotides represent 10% of the sequence (number of nucleotides at the 5' and 3' ends not matched/total number of nucleotides in the query sequence) so 10% is subtracted from the percent identity score calculated by the FASTDB program. If the remaining 90 nucleotides were perfectly matched the final percent identity would be 90%. In another example, a 90 nucleotide subject sequence is compared with a 100 nucleotide query sequence. This time the deletions are internal deletions so that there are no nucleotides on the 5' or 3' of the subject sequence which are not matched/aligned with the query. In this case the percent identity calculated by FASTDB is not manually corrected. Once again, only nucleotides 5' and 3' of the subject sequence which are not matched/aligned with the query sequence are manually corrected for. No other manual corrections are made for the purposes of the present invention.

Regulatory Sequences of CCRP-1

As mentioned, the genomic sequence of the CCRP-1 gene contains regulatory sequences both in the non-coding 5'-flanking region and possibly in the non-coding 3'-flanking region that border the CCRP-1 coding region containing the exons of this gene.

Polynucleotides derived from the 5' and 3' regulatory regions are useful in order to detect the presence of at least a copy of a genomic nucleotide sequence of the CCRP-1 gene or a fragment thereof in a test sample.

The promoter activity of the 5' regulatory regions contained in CCRP-1 can be assessed as described below. In order to identify the relevant biologically active polynucleotide fragments or variants of the promoter region, one of skill in the art will use recombinant vectors comprising a reporter gene. The expression of the reporter gene will be detected when placed under the control of biologically active polynucleotide fragments or variants of the CCRP-1 promoter region located upstream of the first exon of the CCRP-1 gene suitable promoter reporter vectors, into which the CCRP-1 promoter sequences may be cloned include, pSEAP-Basic, pSEAP-Enhancer, pβgal-Basic, pβgal-Enhancer, or pEGFP-1 Promoter Reporter vectors available from Clontech, or pGL2-basic or pGL3-basic promoterless luciferase reporter gene vector from Promega. Briefly, each of these promoter reporter vectors include multiple cloning sites positioned upstream of a reporter gene encoding a readily assayable protein such as secreted alkaline phosphatase, luciferase, β-galactosidase, or green fluorescent protein. The sequences upstream the CCIP-1 coding region are inserted into the cloning sites upstream of the reporter gene in both orientations and introduced into an appropriate host cell. The level of reporter protein is assayed and compared to the level obtained from a vector which lacks an insert in the cloning site. The presence of an elevated expression level in the vector containing the insert with respect to the control vector indicates the presence of a promoter in the insert. If necessary, the upstream sequences can be cloned into vectors which contain an enhancer for increasing transcription levels from weak promoter sequences. A significant level of expression above that observed with the vector lacking an insert indicates that a promoter sequence is present in the inserted upstream sequence.

Promoter sequence within the upstream genomic DNA may be further defined by constructing nested 5' and/or 3' deletions in the upstream DNA using conventional techniques such as Exonuclease III or appropriate restriction endonuclease digestion. The resulting deletion fragments can be inserted into the promoter reporter vector to determine whether the deletion has increased, reduced or illuminated promoter activity, such as described, for example, by Coles et al. (1998), the disclosure of which is incorporated herein by reference in its entirety. In this way, the boundaries of the promoters may be defined. If desired, potential individual regulatory sites within the promoter may be identified using site directed mutagenesis or linker scanning to obliterate potential transcription factor binding sites within the promoter individually or in combination. The effects of these mutations on transcription levels may be determined by inserting the mutations into cloning sites in promoter reporter vectors. This type of assay is well known to those skilled in the art and is described in WO 97/17359, U.S. Pat. No. 5,374,544; EP 582 796; U.S. Pat. Nos. 5,698,389; 5,643,746; 5,502,176; and 5,266,488; the disclosures of which are incorporated by reference herein in their entirety.

The strength and the specificity of the promoter of the CCRP-1 gene can be assessed through the expression levels of a detectable polynucleotide operably linked to the CCRP-1 promoter in different types of cells and tissues. The detectable polynucleotide may be either a polynucleotide that specifically hybridizes with a predefined oligonucleotide probe, or a polynucleotide encoding a detectable protein, including a CCRP-1 polypeptide or a fragment or a variant thereof. This type of assay is well known to those skilled in the art and is described in U.S. Pat. Nos. 5,502,176; and 5,266,488; the disclosures of which are incorporated by reference herein in their entirety. Some of the methods are discussed in more detail below.

Polynucleotides carrying the regulatory elements located at the 5' end and at the 3' end of the CCRP-1 coding region may be advantageously used to control the transcriptional and translational activity of a heterologous polynucleotide of interest.

Thus, the present invention also concerns a purified or isolated nucleic acid comprising a polynucleotide which is selected from the group consisting of the 5' and 3' regulatory regions, or a sequence complementary thereto or a biologically active fragment or variant thereof. The invention also pertains to a purified or isolated nucleic acid comprising a polynucleotide having at least 95% nucleotide identity with a polynucleotide selected from the group consisting of the 5' and 3' regulatory regions, advantageously 99% nucleotide identity, preferably 99.5% nucleotide identity and most preferably 99.8% nucleotide identity with a polynucleotide selected from the group consisting of the 5' and 3' regulatory regions, or a sequence complementary thereto or a variant thereof or a biologically active fragment thereof.

Another object of the invention consists of purified, isolated or recombinant nucleic acids comprising a polynucleotide that hybridizes, under the stringent hybridization conditions defined herein, with a polynucleotide selected from the group consisting of the nucleotide sequences of the 5'- and 3' regulatory regions, or a sequence complementary thereto or a variant thereof or a biologically active fragment thereof.

Preferred fragments of the 5' regulatory region have a length of about 1500 or 1000 nucleotides, preferably of about 500 nucleotides, more preferably about 400 nucleotides, even more preferably 300 nucleotides and most preferably about 200 nucleotides. Preferred fragments of the 3' regulatory region are at least 50, 100, 150, 200, 300 or 400 bases in length. "Biologically active" polynucleotide derivatives of the 5' regulatory region are polynucleotides comprising or alternatively consisting of a fragment of said polynucleotide which is functional as a regulatory region for expressing a recombinant polypeptide or a recombinant polynucleotide in a recombinant cell host. It could act either as an enhancer or as a repressor. For the purpose of the invention, a nucleic acid or polynucleotide is "functional" as a regulatory region for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The regulatory polynucleotides of the invention may be prepared from the nucleotide sequence of CCRP-1 genomic sequence, for example, by cleavage using suitable restriction enzymes, or by PCR. The regulatory polynucleotides may also be prepared by digestion of a CCRP-1 gene containing genomic clone by an exonuclease enzyme, such as Bal31 (Wabiko et al., 1986). These regulatory polynucleotides can also be prepared by nucleic acid chemical synthesis, as described elsewhere in the specification.

The regulatory polynucleotides according to the invention may be part of a recombinant expression vector that may be used to express a coding sequence in a desired host cell or host organism. The recombinant expression vectors according to the invention are described elsewhere in the specification.

A preferred 5'-regulatory polynucleotide of the invention includes the 5'-untranslated region (5'-UTR) of the CCRP-1 cDNA, or a biologically active fragment or variant thereof.

A preferred 3'-regulatory polynucleotide of the invention includes the 3'-untranslated region (3'-UTR) of the CCRP-1 cDNA, or a biologically active fragment or variant thereof.

A further object of the invention consists of a purified or isolated nucleic acid comprising:
  a) a polynucleotide acid comprising a regulatory nucleotide sequence selected from the group consisting of:
    (i) a nucleotide sequence comprising a polynucleotide of the 5' regulatory region or a complementary sequence thereto;
    (ii) a nucleotide sequence comprising a polynucleotide having at least 95% of nucleotide identity with the nucleotide sequence of the 5' regulatory region or a complementary sequence thereto;
    (iii) a nucleotide sequence comprising a polynucleotide that hybridizes under stringent hybridization conditions with the nucleotide sequence of the 5' regulatory region or a complementary sequence thereto; and
    (iv) a biologically active fragment or variant of the polynucleotides in (i), (ii) and (iii);
  b) a polynucleotide encoding a desired polypeptide or a nucleic acid molecule of interest, operably linked to the polynucleotide defined in (a) above;
  c) optionally, a nucleic acid comprising a 3'- regulatory polynucleotide, preferably a 3'-regulatory polynucleotide of the CCRP-1 gene.

In a specific embodiment the nucleic acid molecules defined above, includes the 5'-untranslated region (5'-UTR) of the CCRP-1 cDNA, or a biologically active fragment or variant thereof.

In a second specific embodiment the nucleic acid molecules defined above, includes the 3'-untranslated region (3'-UTR) of the CCRP-1 cDNA, or a biologically active fragment or variant thereof.

The regulatory polynucleotide of the 5' regulatory region, or its biologically active fragments or variants, is operably linked at the 5'-end of the polynucleotide encoding the desired polypeptide or polynucleotide.

The regulatory polynucleotide of the 3' regulatory region, or its biologically active fragments or variants, is advantageously operably linked at the 3'-end of the polynucleotide encoding the desired polypeptide or polynucleotide.

The desired polypeptide encoded by the above-described nucleic acid may be of various nature or origin, encompassing proteins of prokaryotic viral or eukaryotic origin. Among the polypeptides expressed under the control of a CCRP-1 regulatory region include bacterial, fungal or viral antigens. Also encompassed are eukaryotic proteins such as intracellular proteins, such as "house keeping" proteins, membrane-bound proteins, such as mitochondrial membrane-bound proteins and cell surface receptors, and secreted proteins such as endogenous mediators such as cytokines. The desired polypeptide may be the CCRP-1 protein, especially the protein of the amino acid sequence of SEQ ID NO:2, or a fragment or a variant thereof.

The desired nucleic acids encoded by the above-described polynucleotide, usually an RNA molecule, may be complementary to a desired coding polynucleotide, for example to the CCRP-1 coding sequence, and thus useful as an antisense polynucleotide. Such a polynucleotide may be included in a recombinant expression vector in order to express the desired polypeptide or the desired nucleic acid in host cell or in a host organism. Suitable recombinant vectors that contain a polynucleotide such as described herein are disclosed elsewhere in the specification.

Recombinant Vectors

The term "vector" is used herein to designate either a circular or a linear DNA or RNA molecule, which is either double-stranded or single-stranded, and which comprise at least one polynucleotide of interest that is sought to be transferred in a cell host or in a unicellular or multicellular host organism. The present invention encompasses a family of recombinant vectors that comprise a regulatory polynucleotide derived from the CCRP-1 genomic sequence, and/or a coding polynucleotide from either the CCRP-1 genomic sequence or the cDNA sequence. Generally, a recombinant vector of the invention may comprise any of the polynucleotides described herein, including regulatory sequences, coding sequences and polynucleotide constructs, as well as any CCRP-1 primer or probe as defined above.

In a first preferred embodiment, a recombinant vector of the invention is used to amplify the inserted polynucleotide derived from a CCRP-1 genomic sequence or a CCRP-1 cDNA, for example the cDNA of SEQ ID NO:1 in a suitable cell host, this polynucleotide being amplified at every time that the recombinant vector replicates.

A second preferred embodiment of the recombinant vectors according to the invention comprises expression vectors comprising either a regulatory polynucleotide or a coding nucleic acid of the invention, or both. Within certain embodiments, expression vectors are employed to express a CCRP-1 polypeptide which can be then purified and, for example be used in ligand screening assays or as an immunogen in order to raise specific antibodies directed against the CCRP-1 protein. In other embodiments, the expression vectors are used for constructing transgenic animals and also for gene therapy. Expression requires that appropriate signals are provided in the vectors, said signals including various regulatory elements, such as enhancers/promoters from both viral and mammalian sources that drive expression of the genes of interest in host cells. Dominant drug selection markers for establishing permanent, stable cell clones expressing the products are generally included in the expression vectors of the invention, as they are elements that link expression of the drug selection markers to expression of the polypeptide.

More particularly, the present invention relates to expression vectors which include nucleic acids encoding a CCRP-1 protein, preferably the CCRP-1 protein of the amino acid sequence of SEQ ID NO:2 or variants or fragments thereof.

Some of the elements which can be found in the vectors of the present invention are described in further detail in the following sections.

General Features of the Expression Vectors of the Invention

A recombinant vector according to the invention comprises, but is not limited to, a YAC (Yeast Artificial Chromosome), a BAC (Bacterial Artificial Chromosome), a phage, a phagemid, a cosmid, a plasmid or even a linear DNA molecule which may comprise a chromosomal, non-chromosomal, semi-synthetic and synthetic DNA. Such a recombinant vector can comprise a transcriptional unit comprising an assembly of:

(1) a genetic element or elements having a regulatory role in gene expression, for example promoters or enhancers. Enhancers are cis-acting elements of DNA, usually from about 10 to 300 bp in length that act on the promoter to increase the transcription.

(2) a structural or coding sequence which is transcribed into mRNA and eventually translated into a polypeptide, said structural or coding sequence being operably linked to the regulatory elements described in (1); and (3) appropriate transcription initiation and termination sequences. Structural units intended for use in yeast or eukaryotic expression systems preferably include a leader sequence enabling extracellular secretion of translated protein by a host cell. Alternatively, when a recombinant protein is expressed without a leader or transport sequence, it may include a N-terminal residue. This residue may or may not be subsequently cleaved from the expressed recombinant protein to provide a final product.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation signal, splice donor and acceptor sites, transcriptional termination sequences, and 5'-flanking non-transcribed sequences. DNA sequences derived from the SV40 viral genome, for example SV40 origin, early promoter, enhancer, splice and polyadenylation signals may be used to provide the required non-transcribed genetic elements.

The in vivo expression of a CCRP-1 polypeptide of the present invention may be useful in order to correct a genetic defect related to the expression of the native gene in a host organism or to the production of a biologically inactive CCRP-1 protein.

Consequently, the present invention also comprises recombinant expression vectors mainly designed for the in vivo production of a CCRP-1 polypeptide the present invention by the introduction of the appropriate genetic material in the organism or the patient to be treated. This genetic material may be introduced in vitro in a cell that has been previously extracted from the organism, the modified cell being subsequently reintroduced in the said organism, directly in vivo into the appropriate tissue.

Regulatory Elements

The suitable promoter regions used in the expression vectors according to the present invention are chosen taking into account the cell host in which the heterologous gene has to be expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors.

Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen), (Smith et al., 1983; O'Reilly et al., 1992), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art. The choice of a promoter is well within the ability of a person skilled in the field of genetic engineering. For example, one may refer to the book of Sambrook et al., (1989) or also to the procedures described by Fuller et al., (1996).

Other regulatory elements: Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

Selectable Markers

Selectable markers confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. coli*, or levan saccharase for mycobacteria, this latter marker being a negative selection marker.

Preferred Vectors

Bacterial vectors: As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), and GEM 1 (Promega Biotec, Madison, Wis., USA).

Large numbers of other suitable vectors are known to those of skill in the art, and commercially available, such as the following bacterial vectors: pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXTI, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb. The construction of P1 bacteriophage vectors such as p158 or p158/neo8 are notably described by Sternberg (1992, 1994). Recombinant P1 clones comprising CCRP-1 nucleotide sequences may be designed for inserting large polynucleotides of more than 40 kb (See Linton et al., 1993). To generate P1 DNA for transgenic experiments; a preferred protocol is the protocol described by McCormick et al. (1994). Briefly, *E. coli* (preferably strain NS3529) harboring the P1 plasmid are grown overnight in a suitable broth medium containing 25 μg/ml of kanamycin. The P1 DNA is prepared from the *E. coli* by alkaline lysis using the Qiagen Plasmid Maxi kit (Qiagen, Chatsworth, Calif., USA), according to the manufacturer's instructions. The P1 DNA is purified from the bacterial lysate on two Qiagen-tip 500 columns, using the washing and elution buffers contained in the kit. A phenol/chloroform extraction is then performed before precipitating the DNA with 70% ethanol. After solubilizing the DNA in TE (10 mM Tris-HCl, pH 7.4, 1 mM EDTA), the concentration of the DNA is assessed by spectrophotometry.

When the goal is to express a P1 clone comprising CCRP-1 nucleotide sequences in a transgenic animal, typically in transgenic mice, it is desirable to remove vector sequences from the P1 DNA fragment, for example by cleaving the P1 DNA at rare-cutting sites within the P1 polylinker (SfiI, NotI or SalI). The P1 insert is then purified from vector sequences on a pulsed-field agarose gel, using methods similar to those originally reported for the isolation of DNA from YACs (See e.g., Schedl et al., 1993a; Peterson et al., 1993). At this stage, the resulting purified insert DNA can be concentrated, if necessary, on a Millipore Ultrafree-MC Filter Unit (Millipore, Bedford, Mass., USA—30,000 molecular weight limit) and then dialyzed against microinjection buffer (10 mM Tris-HCl, pH 7.4; 250 μM EDTA) containing 100 mM NaCl, 30 μM spermine, 70 μM spermidine on a microdyalisis membrane (type VS, 0.025 μM from Millipore). The intactness of the purified P1 DNA insert is assessed by electrophoresis on 1% agarose (Sea Kem GTG; FMC Bio-products) pulse-field gel and staining with ethidium bromide.

Viral Vectors

In one specific embodiment, the vector is derived from an adenovirus. Preferred adenovirus vectors according to the invention are those described by Feldman and Steg (1996), or Ohno et al., (1994). Another preferred recombinant adenovirus according to this specific embodiment of the present invention is the human adenovirus type 2 or 5 (Ad 2 or Ad 5) or an adenovirus of animal origin (French patent application No. FR-93.05954).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host. Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al. (1996), PCT Application No WO 93/25234, PCT Application No WO 94/06920, Roux et al., (1989), Julan et al., (1992), and Neda et al., (1991).

Yet another viral vector system that is contemplated by the invention comprises the adeno-associated virus (AAV). The adeno-associated virus is a naturally occurring defective virus that requires another virus, such as an adenovirus or a herpes virus, as a helper virus for efficient replication and a productive life cycle (Muzyczka et al., 1992). It is also one of the few viruses that may integrate its DNA into non-dividing cells, and exhibits a high frequency of stable integration (Flotte et al. 1992; Samulski et al., 1989; McLaughlin et al., 1989). One advantageous feature of AAV derives from its reduced efficacy for transducing primary cells relative to transformed cells.

BAC Vectors

The bacterial artificial chromosome (BAC) cloning system (Shizuya et al., 1992) has been developed to stably maintain large fragments of genomic DNA (100–300 kb) in *E. coli*. A preferred BAC vector comprises a pBeloBAC11 vector that has been described by Kim et al. (1996). BAC libraries are prepared with this vector using size-selected genomic DNA that has been partially digested using enzymes that permit ligation into either the Bam HI or HindIII sites in the vector. Flanking these cloning sites are T7 and SP6 RNA polymerase transcription initiation sites that can be used to generate end probes by either RNA transcription or PCR methods. After the construction of a BAC library in *E. coli*, BAC DNA is purified from the host cell as a supercoiled circle. Converting these circular molecules into a linear form precedes both size determination and introduction of the BACs into recipient cells. The cloning site is flanked by two Not I sites, permitting cloned segments to be excised from the vector by Not I digestion. Alternatively, the DNA insert contained in the pBeloBAC11 vector may be linearized by treatment of the BAC vector with the commercially available enzyme lambda terminase that leads to the cleavage at the unique cosN site, but this cleavage method results in a full length BAC clone containing both the insert DNA and the BAC sequences.

Baculovirus

Another specific suitable host vector system is the pVL1392/1393 baculovirus transfer vector (Pharmingen) that is used to transfect the SF9 cell line (ATCC NO. CRL 1711) which is derived from *Spodoptera frugiperda*. Other suitable vectors for the expression of the CCRP-1 polypeptide of the present invention in a baculovirus expression system include those described by Chai et al., (1993), Vlasak et al., (1983), and Lenhard et al., (1996).

Delivery Of The Recombinant Vectors

To effect expression of the polynucleotides and polynucleotide constructs of the invention, these constructs must be delivered into a cell. This delivery may be accomplished in vitro, as in laboratory procedures for transforming cell lines, or in vivo or ex vivo, as in the treatment of certain diseases states. One mechanism is viral infection where the expression construct is encapsulated in an infectious viral particle.

Several non-viral methods for the transfer of polynucleotides into cultured mammalian cells are also contemplated by the present invention, and include, without being limited to, calcium phosphate precipitation (Graham et al., 1973; Chen et al., 1987); DEAE-dextran (Gopal, 1985); electroporation (Tur-Kaspa et al., 1986; Potter et al., 1984); direct microinjection (Harland et al., 1985); DNA-loaded liposomes (Nicolau et al., 1982; Fraley et al., 1979); and receptor-mediated transfection. (Wu and Wu, 1987, 1988). Some of these techniques may be successfully adapted for in vivo or ex vivo use.

Once the expression polynucleotide has been delivered into the cell, it may be stably integrated into the genome of the recipient cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle.

One specific embodiment for a method for delivering a protein or peptide to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

Compositions for use in vitro and in vivo comprising a "naked" polynucleotide are described in PCT application No. WO 90/11092 (Vical Inc.) and also in PCT application No. WO 95/11307 (Institut Pasteur, INSERM, Université d'Ottawa) as well as in the articles of Tacson et al. (1996) and of Huygen et al., (1996).

In still another embodiment of the invention, the transfer of a naked polynucleotide of the invention, including a polynucleotide construct of the invention, into cells may be proceeded with a particle bombardment (biolistic), said particles being DNA-coated microprojectiles accelerated to a high velocity allowing them to pierce cell membranes and enter cells without killing them, such as described by Klein et al., (1987).

In a further embodiment, the polynucleotide of the invention may be entrapped in a liposome (Ghosh and Bacchawat, 1991; Wong et al., 1980; Nicolau et al., 1987).

In a specific embodiment, the invention provides a composition for the in vivo production of the CCRP-1 protein or polypeptide described herein. It comprises a naked polynucleotide operatively coding for this polypeptide, in solution in a physiologically acceptable carrier, and suitable for introduction into a tissue to cause cells of the tissue to express the said protein or polypeptide.

The amount of vector to be injected to the desired host organism varies according to the site of injection. As an indicative dose, it will be injected between 0,1 and 100 µg of the vector in an animal body, preferably a mammal body, for example a mouse body.

In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired CCRP-1 polypeptide or the desired fragment thereof is reintroduced into the animal body in order to deliver the recombinant protein within the body either locally or systemically.

Host Cells

Another object of the invention comprises a host cell that has been transformed or transfected with one of the polynucleotides described herein, and in particular a polynucleotide either comprising a CCRP-1 regulatory polynucleotide or the polynucleotide coding for a sequence CCRP-1 polypeptide. Also included are host cells that are transformed (prokaryotic cells) or that are transfected (eukaryotic cells) with a recombinant vector such as one of those described above. However, the cell hosts of the present invention can comprise any of the polynucleotides of the present invention. Preferred host cells used as recipients for the expression vectors of the invention are the following:

a) Prokaryotic host cells: *Escherichia coli* strains (I.E.DH5-α strain), *Bacillus subtilis, Salmonella typhimurium*, and strains from species like Pseudomonas, Streptomyces and Staphylococcus.

b) Eukaryotic host cells: HeLa cells (ATCC No.CCL2; No.CCL2.1; No.CCL2.2), Cv 1 cells (ATCC No.CCL70), COS cells (ATCC No.CRL1650; No.CRL1651), Sf-9 cells (ATCC No.CRL1711), C127 cells (ATCC No. CRL-1804), 3T3 (ATCC No. CRL-6361), CHO (ATCC No. CCL-61), human kidney 293. (ATCC No.45504; No. CRL-1573) and BHK (ECACC No. 84100501; No. 84111301).

c) Other mammalian host cells.

The present invention also encompasses primary, secondary, and immortalized homologously recombinant host cells of vertebrate origin, preferably mammalian origin and particularly human origin, that have been engineered to: a) insert exogenous (heterologous) polynucleotides into the endogenous chromosomal DNA of a targeted gene, b) delete endogenous chromosomal DNA, and/or c) replace endogenous chromosomal DNA with exogenous polynucleotides. Insertions, deletions, and/or replacements of polynucleotide sequences may be to the coding sequences of the targeted gene and/or to regulatory regions, such as promoter and enhancer sequences, operably associated with the targeted gene.

The present invention further relates to a method of making a homologously recombinant host cell in vitro or in vivo, wherein the expression of a targeted gene not normally expressed in the cell is altered. Preferably the alteration causes expression of the targeted gene under normal growth conditions or under conditions suitable for producing the polypeptide encoded by the targeted gene. The method comprises the steps of: (a) transfecting the cell in vitro or in vivo with a polynucleotide construct, the a polynucleotide construct comprising; (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination.

The present invention further relates to a method of altering the expression of a targeted gene in a cell in vitro or in vivo wherein the gene is not normally expressed in the cell, comprising the steps of: (a) transfecting the cell in vitro or in vivo with a a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; and (b) maintaining the transfected cell in vitro or in vivo under conditions appropriate for homologous recombination, thereby producing a homologously recombinant cell; and (c) maintaining the homologously recombinant cell in vitro or in vivo under conditions appropriate for expression of the gene.

The present invention further relates to a method of making a polypeptide of the present invention by altering the expression of a targeted endogenous gene in a cell in vitro or in vivo wherein the gene is not normally expressed in the cell, comprising the steps of: a) transfecting the cell in vitro with a a polynucleotide construct, the a polynucleotide construct comprising: (i) a targeting sequence; (ii) a regulatory sequence and/or a coding sequence; and (iii) an unpaired splice donor site, if necessary, thereby producing a transfected cell; (b) maintaining the transfected cell in vitro or in vivo under conditions appropriate for homologous recombination, thereby producing a homologously recombinant cell; and c) maintaining the homologously recombinant cell in vitro or in vivo under conditions appropriate for expression of the gene thereby making the polypeptide.

The present invention further relates to a a polynucleotide construct which alters the expression of a targeted gene in a cell type in which the gene is not normally expressed. This occurs when the a polynucleotide construct is inserted into the chromosomal DNA of the target cell, wherein the a polynucleotide construct comprises: a) a targeting sequence; b) a regulatory sequence and/or coding sequence; and c) an unpaired splice-donor site, if necessary. Further included are a polynucleotide constructs, as described above, wherein the construct further comprises A a polynucleotide which encodes a polypeptide and is in-frame with the targeted endogenous gene after homologous recombination with chromosomal DNA.

The compositions may be produced, and methods performed, by techniques known in the art, such as those described in U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; International Publication Nos:WO96/2941 1, WO 94/12650; and scientific articles described by Koller et al., (1994), the disclosures of each of which are incorporated herein by reference in their entireties.

The CCRP-1 gene expression in mammalian, and typically human, cells may be rendered defective, or alternatively it may be proceeded with the insertion of a CCRP-1 genomic or cDNA sequence with the replacement of the CCRP-1 gene counterpart in the genome of an animal cell by a CCRP-1 polynucleotide according to the invention. These genetic alterations may be generated by homologous recombination events using specific DNA constructs that have been previously described.

One kind of cell hosts that may be used are mammal zygotes, such as murine zygotes. For example, murine zygotes may undergo microinjection with a purified DNA molecule of interest, for example a purified DNA molecule that has previously been adjusted to a concentration range from 1 ng/ml—for BAC inserts—3 ng/$\mu$l—for P1 bacteriophage inserts—in 10 mM Tris-HCl, pH 7.4, 250 $\mu$M EDTA containing 100 mM NaCl, 30 $\mu$M spermine, and 70 $\mu$M spermidine. When the DNA to be microinjected has a large size, polyamines and high salt concentrations can be used in order to avoid mechanical breakage of this DNA, as described by Schedl et al (1993b).

Any one of the polynucleotides of the invention, including the DNA constructs described herein, may be introduced in an embryonic stem (ES) cell line, preferably a mouse ES cell line. ES cell lines are derived from pluripotent, uncommitted cells of the inner cell mass of pre-implantation blastocysts. Preferred ES cell lines are the following: ES-E14TG2a (ATCC No.CRL-1821), ES-D3 (ATCC No.CRL1934 and No. CRL-11632), YS001 (ATCC No. CRL-11776), 36.5 (ATCC No. CRL-11116). To maintain ES cells in an uncommitted state, they are cultured in the presence of growth inhibited feeder cells which provide the appropriate signals to preserve this embryonic phenotype and serve as a matrix for ES cell adherence. Preferred feeder cells are primary embryonic fibroblasts that are established from tissue of day 13-day 14 embryos of virtually any mouse strain, that are maintained in culture, such as described by Abbondanzo et al. (1993) and are inhibited in growth by irradiation, such as described by Robertson (1987), or by the presence of an inhibitory concentration of LIF, such as described by Pease and Williams (1990).

The constructs in the host cells can be used in a conventional manner to produce the gene product encoded by the recombinant sequence.

Following transformation of a suitable host and growth of the host to an appropriate cell density, the selected promoter is induced by appropriate means, such as temperature shift or chemical induction, and cells are cultivated for an additional period. Cells are typically harvested by centrifugation, disrupted by physical or chemical means, and the resulting crude extract retained for further purification. Microbial cells employed in the expression of proteins can be disrupted by any convenient method, including freeze-thaw cycling, sonication, mechanical disruption, or use of cell lysing agents. Such methods are well known by the skill artisan.

Transzenic Animals

The terms "transgenic animals" or "host animals" are used herein designate animals that have their genome genetically and artificially manipulated so as to include one of the nucleic acids according to the invention. Preferred animals are non-human mammals and include those belonging to a genus selected from Mus (e.g. mice), Rattus (e.g. rats) and Oryctogalus (e.g. rabbits) which have their genome artificially and genetically altered by the insertion of a nucleic acid according to the invention. In one embodiment, the invention encompasses non-human host mammals and animals comprising a recombinant vector of the invention or a CCRP-1 gene disrupted by homologous recombination with a knock out vector.

The transgenic animals of the invention all include within a plurality of their cells a cloned recombinant or synthetic DNA sequence, more specifically one of the purified or isolated nucleic acids comprising a CCRP-1 coding sequence, a CCRP-1 regulatory polynucleotide, a polynucleotide construct, or a DNA sequence encoding an antisense polynucleotide such as described in the present specification.

Generally, a transgenic animal according the present invention comprises any one of the polynucleotides, the recombinant vectors and the cell hosts described in the present invention. However, the transgenic animals of the present invention can comprise any of the polynucleotides of the present invention. In a first preferred embodiment, these transgenic animals may be good experimental models in order to study the diverse pathologies related to fatty acid metabolism, in particular concerning the transgenic animals within the genome of which has been inserted one or several copies of a polynucleotide encoding a native CCRP-1 protein, or alternatively a mutant CCRP-1 protein.

In a second preferred embodiment, these transgenic animals may express a desired polypeptide of interest under the control of the regulatory polynucleotides of the CCRP-1 gene, leading to good yields in the synthesis of this protein of interest, and eventually a tissue specific expression of this protein of interest.

In a third preferred embodiment, these transgenic animals may express a desired polypeptide of interest fused to a CCRP-1 mitochondrial signal peptide sequence, leading to the translocation of the fusion (chimeric) polypeptide to mitochondria.

The design of the transgenic animals of the invention may be made according to the conventional techniques well known from the one skilled in the art. For more details regarding the production of transgenic animals, and specifically transgenic mice, it may be referred to U.S. Pat. No. 4,873,191, issued Oct. 10, 1989; U.S. Pat. No. 5,464,764 issued Nov. 7, 1995; and U.S. Pat. No. 5,789,215, issued Aug. 4, 1998; these documents being incorporated herein by reference in their entireties to disclose methods producing transgenic mice.

Transgenic animals of the present invention are produced by the application of procedures which result in an animal with a genome that has incorporated exogenous genetic material. The procedure involves obtaining the genetic material, or a portion thereof, which encodes either a CCRP-1 coding sequence, a CCRP-1 regulatory polynucleotide or a DNA sequence encoding a CCRP-1 antisense polynucleotide such as described in the present specification. A recombinant polynucleotide of the invention is inserted into an embryonic or ES stem cell line. The insertion is preferably made using electroporation, such as described by Thomas et al. (1987). The cells subjected to electroporation are screened (e.g. by selection via selectable markers, by PCR or by Southern blot analysis) to find positive cells which have integrated the exogenous recombinant polynucleotide into their genome, preferably via an homologous recombination event. An illustrative positive-negative selection procedure that may be used according to the invention is described by Mansour et al. (1988).

The positive cells are then isolated, cloned and injected into 3.5 days old blastocysts from mice, such as described by Bradley (1987). The blastocysts are then inserted into a female host animal and allowed to grow to term. Alternatively, the positive ES cells are brought into contact with embryos at the 2.5 days old 8–16 cell stage (morulae) such as described by Wood et al. (1993), or by Nagy et al. (1993), the ES cells being internalized to colonize extensively the blastocyst including the cells which will give rise to the germ line.

The offspring of the female host are tested to determine which animals are transgenic e.g. include the inserted exogenous DNA sequence and which are wild type.

Thus, the present invention also concerns a transgenic animal containing a nucleic acid, a recombinant expression vector or a recombinant host cell according to the invention.

Recombinant Cell Lines Derived From The Transgenic Animals Of The Invention

A further object of the invention comprises recombinant host cells obtained from a transgenic animal described herein. In one embodiment the invention encompasses cells derived from non-human host mammals and animals comprising a recombinant vector of the invention or a CCRP-1 gene disrupted by homologous recombination with a knock out vector.

Recombinant cell lines may be established in vitro from cells obtained from any tissue of a transgenic animal according to the invention, for example by transfection of primary cell cultures with vectors expressing onc-genes such as SV40 large T antigen, as described by Chou (1989), and Shay et al. (1991).

Polynucleotides Constructs: DNA Construct that Enables Directing Temporal and Spatial CCRP-1 Gene Expression in Recombinant Cell Hosts and in Transgenic Animals In order to study the physiological and phenotypic consequences of a lack of synthesis of the CCRP-1 protein, both at the cell level and at the multi cellular organism level, the invention also encompasses DNA constructs and recombinant vectors enabling a conditional expression of a specific allele of the CCRP-1 genomic sequence or cDNA and also of a copy of this genomic sequence or cDNA harboring substitutions, deletions, or additions of one or more bases as regards to the CCRP-1 nucleotide sequence of the genomic and cDNA, or a fragment thereof, these base substitutions, deletions or additions being located either in an exon, an intron or a regulatory sequence, but preferably in the 5'-regulatory sequence or in an exon of the CCRP-1 genomic sequence or within the CCRP-1 cDNA. In a preferred embodiment, the CCRP-1 sequence comprises a biallelic marker of the present invention.

The present invention embodies recombinant vectors comprising any one of the polynucleotides described in the present invention. A first preferred DNA construct is based on the tetracycline resistance operon tet from E. coli transposon Tn10 for controlling the CCRP-1 gene expression, such as described by Gossen et al. (1992, 1995) and Furth et al. (1994). Such a DNA construct contains seven tet operator sequences from Tn10 (tetop) that are fused to either a minimal promoter or a 5'-regulatory sequence of the CCRP-1 gene, said minimal promoter or said CCRP-1 regulatory sequence being operably linked to a polynucleotide of interest that codes either for a sense or an antisense oligonucleotide or for a polypeptide, including a CCRP-1 polypeptide or a peptide fragment thereof. This DNA construct is functional as a conditional expression system for the nucleotide sequence of interest when the same cell also comprises a nucleotide sequence coding for either the wild type (tTA) or the mutant (rTA) repressor fused to the activating domain of viral protein VP16 of herpes simplex virus, placed under the control of a promoter, such as the HCMVIE1 enhancer/promoter or the MMTV-LTR. Indeed, a preferred DNA construct of the invention comprises both the polynucleotide containing the tet operator sequences and the polynucleotide containing a sequence coding for the tTA or the rTA repressor.

In a specific embodiment, the conditional expression DNA construct contains the sequence encoding the mutant tetracycline repressor rTA, the expression of the polynucleotide of interest is silent in the absence of tetracycline and induced in its presence.

DNA Constructs Allowing Homologous Recombination: Replacement Vectors

A second preferred DNA construct will comprise, from 5'-end to 3'-end: (a) a first nucleotide sequence that is comprised in the CCRP-1 genomic sequence; (b) a nucleotide sequence comprising a positive selection marker, such as the marker for neomycine resistance (neo); and (c) a second nucleotide sequence that is comprised in the CCRP-1 genomic sequence, and is located on the genome downstream the first CCRP-1 nucleotide sequence (a).

In a preferred embodiment, this DNA construct also comprises a negative selection marker located upstream the nucleotide sequence (a) or downstream the nucleotide sequence (c). Preferably, the negative selection marker comprises the thymidine kinase (tk) gene (Thomas et al., 1986), the hygromycine beta gene (Te Riele et al. 1990), the hprt gene (Van der Lugt et al., 1991; Reid et al., 1990), or the Diphteria toxin A fragment (Dt-A) gene (Nada et al., 1993; Yagi et al., 1990). Preferably, the positive selection marker is located within a CCRP-1 exon sequence so as to interrupt the sequence encoding a CCRP-1 protein. These replacement vectors are described, for example, by Thomas et al. (1986, 1987), Mansour et al. (1988) and Koller et al. (1992).

The first and second nucleotide sequences (a) and (c) may be indifferently located within a CCRP-1 regulatory sequence, an intronic sequence, an exon sequence or a sequence containing both regulatory and/or intronic and/or exon sequences. The size of the nucleotide sequences (a) and (c) ranges from 1 to 50 kb, preferably from 1 to 10 kb, more preferably from 2 to 6 kb and most preferably from 2 to 4 kb.

DNA Constructs Allowing Homologous Recombination: Cre-LoxP System

These new DNA constructs make use of the site-specific recombination system of the P1 phage. The P1 phage possesses a recombinase called Cre which interacts specifically with a 34 base pairs loxP site. The loxP site is composed of two palindromic sequences of 13 bp separated by a 8 bp conserved sequence. (Hoess et al., 1986). The recombination by the Cre enzyme between two loxP sites having an identical orientation leads to the deletion of the DNA fragment.

The Cre-loxP system used in combination with a homologous recombination technique has been first described by Gu et al. (1993, 1994). Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host. The recombinase enzyme may be brought at the desired time either by (a) incubating the recombinant cell hosts in a culture medium containing this enzyme, by injecting the Cre enzyme directly into the desired cell, such as described by Araki et al. (1995), or by lipofection of the enzyme into the cells, such as described by Baubonis et al. (1993); (b) transfecting the cell host with a vector comprising the Cre coding sequence operably linked to a promoter functional in the recombinant cell host, which promoter being optionally inducible, said vector being introduced in the recombinant cell host, such as described by Gu et al. (1993) and Sauer et al. (1988); (c) introducing in the genome of the cell host a polynucleotide comprising the Cre coding sequence operably linked to a promoter functional in the recombinant cell host, which promoter is optionally inducible, and said polynucleotide being inserted in the genome of the cell host either by a random insertion event or an homologous recombination event, such as described by Gu et al. (1994).

In a specific embodiment, the vector containing the sequence to be inserted in the CCRP-1 gene by homologous recombination is constructed in such a way that selectable markers are flanked by loxP sites of the same orientation, it is possible, by treatment by the Cre enzyme, to eliminate the selectable markers while leaving the CCRP-1 sequences of interest that have been inserted by an homologous recombination event. Again, two selectable markers are needed: a positive selection marker to select for the recombination event and a negative selection marker to select for the homologous recombination event. Vectors and methods using the Cre-loxP system are described by Zou et al. (1994).

Thus, a third preferred DNA construct of the invention comprises, from 5'-end to 3'-end: (a) a first nucleotide sequence that is comprised in the CCRP-1 genomic sequence; (b) a nucleotide sequence comprising a polynucleotide encoding a positive selection marker, said nucleotide sequence comprising additionally two sequences defining a site recognized by a recombinase, such as a loxP site, the two sites being placed in the same orientation; and (c) a second nucleotide sequence that is comprised in the CCRP-1 genomic sequence, and is located on the genome downstream of the first CCRP-1 nucleotide sequence (a).

The sequences defining a site recognized by a recombinase, such as a loxP site, are preferably located within the nucleotide sequence (b) at suitable locations bordering the nucleotide sequence for which the conditional excision is sought. In one specific embodiment, two loxP sites are located at each side of the positive selection marker sequence, in order to allow its excision at a desired time after the occurrence of the homologous recombination event.

In a preferred embodiment of a method using the third DNA construct described above, the excision of the polynucleotide fragment bordered by the two sites recognized by a recombinase, preferably two loxP sites, is performed at a desired time, due to the presence within the genome of the recombinant host cell of a sequence encoding the Cre enzyme operably linked to a promoter sequence, preferably an inducible promoter, more preferably a tissue-specific promoter sequence and most preferably a promoter sequence which is both inducible and tissue-specific, such as described by Gu et al. (1994).

The presence of the Cre enzyme within the genome of the recombinant cell host may result from the breeding of two transgenic animals, the first transgenic animal bearing the CCRP-1-derived sequence of interest containing the loxP sites as described above and the second transgenic animal bearing the Cre coding sequence operably linked to a suitable promoter sequence, such as described by Gu et al. (1994).

Spatio-temporal control of the Cre enzyme expression may also be achieved with an adenovirus based vector that contains the Cre gene thus allowing infection of cells, or in vivo infection of organs, for delivery of the Cre enzyme, such as described by Anton and Graham (1995) and Kanegae et al. (1995).

The DNA constructs described above may be used to introduce a desired nucleotide sequence of the invention, preferably a CCRP-1 genomic sequence or a CCRP-1 cDNA sequence, and most preferably an altered copy of a CCRP-1 genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination).

Nuclear Antisense DNA Constructs

Other compositions containing a vector of the invention comprising an oligonucleotide fragment of the nucleic sequence SEQ ID NO:1, preferably a fragment including the start codon of the CCRP-1 gene, as an antisense tool that inhibits the expression of the corresponding CCRP-1 gene. Preferred methods using antisense polynucleotide according to the present invention are the procedures described by Sczakiel et al. (1995) or those described in PCT Application No WO 95/24223, the disclosures of which are incorporated by reference herein in their entirety.

Preferably, the antisense tools are chosen among the polynucleotides (15–200 bp long) that are complementary to the 5' end of the CCRP-1 mRNA. In one embodiment, a combination of different antisense polynucleotides complementary to different parts of the desired targeted gene are used.

Preferred antisense polynucleotides according to the present invention are complementary to a sequence of the mRNAs of CCRP-1 that contains either the translation initiation codon ATG or a splicing site. Further preferred antisense polynucleotides according to the invention are complementary of the splicing site of the CCRP-1 mRNA.

Preferably, the antisense polynucleotides of the invention have a 3' polyadenylation signal that has been replaced with a self-cleaving ribozyme sequence, such that RNA polymerase II transcripts are produced without poly (A) at their 3' ends, these antisense polynucleotides being incapable of export from the nucleus, such as described by Liu et al. (1994). In a preferred embodiment, these CCRP-1 antisense polynucleotides also comprise, within the ribozyme cassette, a histone stem-loop structure to stabilize cleaved transcripts against 3'-5' exonucleolytic degradation, such as the structure described by Eckner et al. (1991).

Oligonucleotide Probes And Primers

Polynucleotides derived from the CCRP-1 gene are useful in order to detect the presence of at least a copy of a CCRP-1 polynucleotide sequence or a fragment, complement, or variant thereof in a test sample.

Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of the genomic or cDNA sequence or the complements thereof. Another object of the invention is a purified, isolated, or recombinant nucleic acid comprising the nucleotide sequence of SEQ ID NO:1 or complementary sequences thereto, as well as allelic variants, and fragments thereof. Moreover, preferred probes and primers of the invention include purified, isolated, or recombinant CCRP-1 cDNAs consisting of, consisting essentially of, or comprising the sequence of SEQ ID NO:2. Particularly preferred probes and primers of the invention include isolated, purified, or recombinant polynucleotides comprising a contiguous span of at least 12, 15, 18, 20, 25, 30, 35, 40, 50, 60, 70, 80, 90, 100, 150, 200, 500, or 1000 nucleotides of SEQ ID NO:2 or the complements thereof.

Detection probes are generally nucleic acid sequences or uncharged nucleic acid analogs such as, for example peptide nucleic acids which are disclosed in International Patent Application WO 92/20702, morpholino analogs which are described in U.S. Pat. Nos. 5,185,444; 5,034,506 and 5,142,047, the disclosures of which are in incorporated herein by reference in their entireties. The probe may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified, U.S. patent application Ser. No. 07/049,061 filed Apr. 19, 1993 describes modifications, which can be used to render a probe non-extendable.

Any of the polynucleotides of the present invention can be labeled, if desired, by incorporating any label known in the art to be detectable by spectroscopic, photochemical, biochemical, immunochemical, or chemical means. For example, useful labels include radioactive substances (including, $^{32}$P, $^{35}$S, $^{3}$H, $^{125}$I), fluorescent dyes (including, 5-bromodesoxyuridin, fluorescein, acetylaminofluorene, digoxigenin) or biotin. Preferably, polynucleotides are labeled at their 3' and 5' ends. Examples of non-radioactive labeling of nucleic acid fragments are described in the French patent No. FR-7810975 or by Urdea et al (1988) or Sanchez-Pescador et al (1988). In addition, the probes according to the present invention may have structural characteristics such that they allow the signal amplification, such structural characteristics being, for example, branched DNA probes, as those described by Urdea et al. (1991) or in the European patent No. EP 0 225 807 (Chiron), the disclosures of which are incorporated herein by reference in their entireties.

A label can also be used to capture the primer, so as to facilitate the immobilization of either the primer or a primer extension product, such as amplified DNA, on a solid support. A capture label is attached to the primers or probes and can be a specific binding member, which forms a binding pair with the solid's phase reagent's specific binding member (e.g. biotin and streptavidin). Therefore depending upon the type of label carried by a polynucleotide or a probe, it may be employed to capture or to detect the target DNA. Further, it will be understood that the polynucleotides, primers or probes provided herein, may, themselves, serve as the capture label. For example, in the case where a solid phase reagent's binding member is a nucleic acid sequence, it may be selected such that it binds a complementary portion of a primer or probe to thereby immobilize the primer or probe to the solid phase. In cases where a polynucleotide probe itself serves as the binding member, those skilled in the art will recognize that the probe will contain a sequence or "tail" that is not complementary to the target. In the case where a polynucleotide primer itself serves as the capture label, at least a portion of the primer will be free to hybridize with a nucleic acid on a solid phase. DNA Labeling techniques are well known to the skilled technician.

The probes of the present invention are useful for a number of purposes. They can be notably used in Southern hybridization to genomic DNA. The probes can also be used to detect PCR amplification products. They may also be used to detect mismatches in the CCRP-1 gene or mRNA using other techniques.

Any of the polynucleotides, primers and probes of the present invention can be conveniently immobilized on a solid support. Solid supports are known to those skilled in the art and include the walls of wells of a reaction tray, test tubes, polystyrene beads, magnetic beads, nitrocellulose strips, membranes, microparticles such as latex particles, sheep (or other animal) red blood cells, duracytes and others. The solid support is not critical and can be selected by one skilled in the art. Thus, latex particles, microparticles, magnetic or non-magnetic beads, membranes, plastic tubes, walls of microtiter wells, glass or silicon chips, sheep (or other suitable animal's) red blood cells and duracytes are all suitable examples. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid support and which has the ability to immobilize the capture reagent through a specific binding reaction. The receptor molecule enables the indirect binding of the capture reagent to a solid support material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's) red blood cells, duracytes® and other configurations known to those of ordinary skill in the art. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Consequently, the invention also comprises a method for detecting the presence of a nucleic acid comprising a nucleotide sequence selected from a group consisting of CCRP-1 genomic, cDNA, or a fragment or a variant thereof and a complementary sequence thereto in a sample, said method comprising the following steps of:

a) bringing into contact a nucleic acid probe or a plurality of nucleic acid probes which can hybridize with a polynucleotide of the present invention present in a biological sample; and b) detecting the hybrid complex formed between the probe and a polynucleotide in the sample.

The invention further concerns a kit for detecting the presence of a nucleic acid comprising a polynucleotide of the present invention and a complementary sequence thereto in a sample, said kit comprising:

a) a nucleic acid probe or a plurality of nucleic acid probes which can hybridize with a polynucleotide of the present invention present in a biological sample; and b) optionally, the reagents necessary for performing the hybridization reaction.

In a first preferred embodiment of this detection method and kit, said nucleic acid probe or the plurality of nucleic acid probes are labeled with a detectable molecule. In a second preferred embodiment of said method and kit, said nucleic acid probe or the plurality of nucleic acid probes has been immobilized on a substrate.

Oliponucleotide Arrays

A substrate comprising a plurality of oligonucleotide primers or probes of the invention may be used either for detecting or amplifying targeted sequences in the CCRP-1 gene and may also be used for detecting mutations in the coding or in the non-coding sequences of the CCRP-1 gene.

Any polynucleotide provided herein may be attached in overlapping areas or at random locations on the solid support. Alternatively the polynucleotides of the invention may be attached in an ordered array wherein each polynucleotide is attached to a distinct region of the solid support that does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092, the disclosures of which are incorporated herein by reference in their entireties. These arrays may generally be produced using mechanical synthesis methods or light directed synthesis methods which incorporate a combination of photolithographic methods and solid phase oligonucleotide synthesis (Fodor et al., 1991). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high-density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, the disclosures of which are incorporated herein by reference in their entireties, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

In another embodiment of the oligonucleotide arrays of the invention, an oligonucleotide probe matrix may advantageously be used to detect mutations occurring in the CCRP-1 gene and preferably in its regulatory region. For this particular purpose, probes are specifically designed to have a nucleotide sequence allowing their hybridization to the genes that carry known mutations (either by deletion, insertion or substitution of one or several nucleotides). By known mutations, it is meant, mutations on the CCRP-1 gene that have been identified according, for example to the technique used by Huang et al. (1996) or Samson et al. (1996).

Another technique that is used to detect mutations in the CCRP-1 gene is the use of a high-density DNA array. Each oligonucleotide probe constituting a unit element of the high density DNA array is designed to match a specific subsequence of the CCRP-1 genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the CCRP-1 gene. In one such design, termed 4L tiled array, is implemented a set of four probes (A, C, G, T), preferably 15-nucleotide oligomers. In each set of four probes, the perfect complement will hybridize more strongly than mismatched probes. Consequently, a nucleic acid target of length L is scanned for mutations with a tiled array containing 4L probes, the whole probe set containing all the possible mutations in the known wild reference sequence. The hybridization signals of the 15-mer probe set tiled array are perturbed by a single base change in the target sequence. As a consequence, there is a characteristic loss of signal or a "footprint" for the probes flanking a mutation position. This technique was described by Chee et al. (1996).

Consequently, the invention concerns an array of nucleic acid molecules comprising at least one polynucleotide described above as probes and primers. Preferably, the invention concerns an array of nucleic acid comprising at least two polynucleotides described above as probes and primers.

Polypentides

The present invention provides for the CCRP-1 polypeptide of SEQ ID NO:2 and of the CCRP-1 polypeptides encoded by the human cDNA of clone 117-005-4-0-E5-FLC. The present invention further provides for CCRP-1 polypeptides encoded by allelic and splice variants, orthologs, and/or species homologs. Procedures known in the art can be used to obtain, allelic variants, splice variants, orthologs, and/or species homologs of genes corresponding to SEQ ID NO:2 and that encoded by clone 117-005-4-0-E5-FLC, using information from the sequences disclosed herein or the clones deposited with the ATCC. The polypeptides of the present invention can be prepared in any suitable manner. Such polypeptides include isolated naturally occurring polypeptides, recombinantly produced polypeptides, synthetically produced polypeptides, or polypeptides produced by a combination of these methods. It is often advantageous to include an additional amino acid sequence which contains secretory or leader sequences, prosequences, sequences which aid in purification, such as multiple histidine residues, or an additional sequence for stability during recombinant production. The polypeptides of the present invention are preferably provided in an isolated form, and preferably are substantially purified. A recombinantly produced version of a polypeptide, including the secreted polypeptide, can be substantially purified using techniques described herein or otherwise known in the art, such as, for example, by the one-step method described in Smith and Johnson (1988).

Mature Proteins and Mitochondrial Signal Peptides

The present invention also encompasses mature forms of the polypeptide having the polypeptide sequence +1 to 240 of SEQ ID NO:2 and/or the mature polypeptide sequence encoded by the human CCRP-1 cDNA of clone 117-005-4-0-E5-FLC.

The signal peptide that directs the CCRP-1 to the mitochondria is believed to comprise amino acid residues −68 to −1 of SEQ ID NO:2. As one of ordinary skill would appreciate, however, cleavage sites sometimes vary from organism to organism and cannot be predicted with absolute certainty. Accordingly, the present invention provides secreted polypeptides having a sequence shown in SEQ ID NO:2 which have an N-terminus beginning within 5 residues (i.e.,+ or −1 through 5 residues) of the predicted cleavage point. Similarly, it is also recognized that in some cases, cleavage of the signal sequence from a secreted protein is not entirely uniform, resulting in more than one secreted species. These polypeptides are contemplated by the present invention. Moreover, the signal sequence identified above may possibly not be the naturally occurring signal sequence. For example, the naturally occurring signal sequence may be further upstream or downstream from the predicted signal peptide. However, it is believed that polypeptides of the present invention comprising the predicted signal peptide will be capable of directing the entire CCRP-1 protein, fragments thereof, heterologous polypeptides, linked polynucleotides, and linked small molecules to the mitochondria. Nonetheless, the present invention provides for mitochondrial signaling peptides, and mature protein obtained from the cleavage thereof, produced by expression of the polynucleotide sequence of SEQ ID NO:1 and/or the polynucleotide sequence contained in the cDNA of clone 117-005-4-0-E5-FLC, in a mammalian cell (e.g., COS cells, as described below).

To improve or alter the characteristics of CCRP-1 polypeptides of the present invention, protein engineering may be employed. Recombinant DNA technology known to those skilled in the art can be used to create novel mutant proteins or muteins including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions. Further, the polypeptides of the present invention may be produced as multimers including dimers, trimers and tetramers. Multimerization may be facilitated by linkers or recombinantly though heterologous polypeptides such as Fc regions.

It is known in the art that one or more amino acids may be deleted from the N-terminus or C-terminus without substantial loss of biological function. For instance, Ron et al. (1993), reported modified KGF proteins that had heparin binding activity even if 3, 8, or 27 N-terminal amino acid residues were missing. Accordingly, the present invention provides polypeptides having one or more residues deleted from the amino terminus of the polypeptide of SEQ ID NO:2 or that encoded by the human cDNA of clone 117-005-4-0-E5-FLC. Similarly, many examples of biologically functional C-terminal deletion mutants are known. For instance, Interferon gamma shows up to ten times higher activities by deleting 810 amino acid residues from the C-terminus of the protein (See, e.g., Dobeli, et al. 1988). Accordingly, the present invention provides polypeptides having one or more residues deleted from the carboxy terminus of the polypeptides shown of SEQ ID NO:2 or encoded by the human cDNA of clone 117-005-4-0-E5-FLC. The invention also provides polypeptides having one or more amino acids deleted from both the amino and the carboxyl termini as described below.

The present invention is further directed to fragments of the amino acid sequences described herein such as the polypeptide of SEQ ID NO:2 or encoded by the human cDNA of clone 117-005-4-0-E5-FLC. More specifically, the present invention is a purified or isolated polypeptide comprising at least 6 consecutive amino acids of one of the polypeptide of SEQ ID NO:2, the polypeptides encoded by the human cDNA of the deposited, or other polypeptides of the present invention. In a further embodiment, the purified or isolated polypeptide comprises at least 10, 12, 15, 20, 25, 30, 35, 40, 50, 60, 75, 100, 125, 150, 175, 200, 225, 250, 275, or 300 consecutive amino acids of a polypeptide of the present invention.

In addition to the above polypeptide fragments, further preferred sub-genuses of polypeptides comprise at least 6 amino acids, wherein "at least 6" is defined as any integer between 6 and the integer representing the C-terminal amino acid of the polypeptide of the present invention including the polypeptide sequences of the sequence listing below. Further included are species of polypeptide fragments at least 6 amino acids in length, as described above, which are further specified in terms of their N-terminal and C-terminal positions. Preferred species of polypeptide fragments specified by their N-terminal and C-terminal positions include the signal peptide delineated in the sequence listing below. However, included in the present invention as individual species are all polypeptide fragments, at least 6 amino acids in length, as described above, and may be particularly specified by a N-terminal and C-terminal position. That is, every combination of a N-tenninal and C-terminal position that a fragment at least 6 contiguous amino acid residues in length could occupy, on any given amino acid sequence of the sequence listing or of the present invention is included in the present invention.

The present invention also provides for the exclusion of any fragment species specified by N-terminal and C-terminal positions or of any fragment sub-genus specified by size in amino acid residues as described above. Any number of fragments specified by N-terminal and C-terminal positions or by size in amino acid residues as described above may be excluded as individual species.

The above polypeptide fragments of the present invention can be immediately envisaged using the above description and are therefore not individually listed solely for the purpose of not unnecessarily lengthening the specification. Moreover, the above fragments need not have fatty acid metabolizing, translocase, uncoupling, or mitochondrial signal peptide activity, although polypeptides having these activities are preferred embodiments of the invention, since they would be useful, for example, in immunoassays, in epitope mapping, epitope tagging, as vaccines, and as molecular weight markers. The above fragments may also be used to generate antibodies to a particular portion of the polypeptide. These antibodies can then be used in immunoassays well known in the art to distinguish between human and non-human cells and tissues or to determine whether cells or tissues in a biological sample are or are not of the same type which express the polypeptide of the present invention. Preferred polypeptide fragments of the present invention comprising a mitochondrial signal peptides that may be used to facilitate delivery of CCRP-1 polypeptides, heterologous polypeptides, polynucletoides or small molecules to the mitochondria using methods well known in the art.

Other mutants in addition to N- and C-terminal deletion forms of the protein discussed above are included in the present invention. It also will be recognized by one of ordinary skill in the art that some amino acid sequences of the CCRP-1 polypeptides of the present invention can be varied without significant effect of the structure or function of the protein. If such differences in sequence are contemplated, it should be remembered that there will be critical areas on the protein which determine activity. Thus, the invention further includes variations of the CCRP-1 polypeptides which show substantial CCRP-1 polypeptide activity. Such mutants include deletions, insertions, inversions, repeats, and substitutions selected according to general rules known in the art so as to have little effect on activity. For example, guidance concerning how to make phenotypically silent amino acid substitutions is provided.

There are two main approaches for studying the tolerance of an amino acid sequence to change (See, Bowie, J. U. et al. 1990). The first method relies on the process of evolution, in which mutations are either accepted or rejected by natural selection.

The second approach uses genetic engineering to introduce amino acid changes at specific positions of a cloned gene and selections or screens to identify sequences that maintain functionality. These studies have revealed that proteins are surprisingly tolerant of amino acid substitutions. The studies indicate which amino acid changes are likely to be permissive at a certain position of the protein. For example, most buried amino acid residues require nonpolar side chains, whereas few features of surface side chains are generally conserved. Other such phenotypically silent substitutions are described by Bowie et al. (supra) and the references cited therein.

Typically seen as conservative substitutions are the replacements, one for another, among the aliphatic amino acids Ala, Val, Leu and Phe; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Thus, the fragment, derivative, analog, or homolog of the polypeptide of the present invention may be, for example: (i) one in which one or more of the amino acid residues are substituted with a conserved or non-conserved amino acid residue (preferably a conserved amino acid residue) and such substituted amino acid residue may or may not be one encoded by the genetic code: or (ii) one in which one or more of the amino acid residues includes a substituent group: or (iii) one in which the CCRP-1 polypeptide is fused with another compound, such as a compound to increase the half-life of the polypeptide (for example, polyethylene glycol): or (iv) one inwhich the additional amino acids are fused to the above form of the polypeptide, such as an IgG Fc fusion region peptide or leader or secretory sequence or a sequence which is employed for purification of the above form of the polypeptide or a pro-protein sequence. Such fragments, derivatives and analogs are deemed to be within the scope of those skilled in the art from the teachings herein.

Thus, the CCRP-1 polypeptides of the present invention may include one or more amino acid substitutions, deletions, or additions, either from natural mutations or human manipulation. As indicated, changes are preferably of a minor nature, such as conservative amino acid substitutions that do not significantly affect the folding or activity of the protein. The following groups of amino acids generally represent equivalent changes: (1) Ala, Pro, Gly, Glu, Asp, Gln, Asn, Ser, Thr; (2) Cys, Ser, Tyr, Thr; (3) Val, Ile, Leu, Met, Ala, Phe; (4) Lys, Arg, His; (5) Phe, Tyr, Trp, His. A specific embodiment of a modified CCRP-1 peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO-CH2) cetomethylene bond, a (CHOH-CH2) hydroxyethylene bond), a (N—N) bound, a E-alcene bond or also a —CH=CH— bond. The invention also encompasses a human CCRP-1 polypeptide or a fragment or a variant thereof in which at least one peptide bond has been modified as described above.

Amino acids in the CCRP-1 proteins of the present invention that are essential for function can be identified by methods known in the art, such as site-directed mutagenesis or alanine-scanning mutagenesis (See, e.g., Cunningham et al. 1989). The latter procedure introduces single alanine mutations at every residue in the molecule. The resulting mutant molecules are then tested for biological activity using assays appropriate for measuring the function of the particular protein. Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic, (See, e.g., Pinckard et al., 1967; Robbins, et al., 1987; and Cleland, et al., 1993).

The polypeptides of the present invention are preferably provided in an isolated form, and may be partially or substantially purified. A recombinantly produced version of the CCRP-1 polypeptide can be substantially purified by the one-step method described by Smith et al. (1988). Polypeptides of the invention also can be purified from natural or recombinant sources using antibodies directed against the polypeptides of the invention in methods which are well known in the art of protein purification.

The polypeptides of the present invention also include polypeptides having an amino acid sequence at least 50% identical, more preferably at least 60% identical, and still more preferably 70%, 80%, 90%, 95%, 96%, 97%, 98% or 99% identical to the polypeptide of SEQ ID NO:2 or a polypeptide encoded by the human cDNA in clone 117-005-4-0-E5-FLC. Further polypeptides of the present invention include polypeptides which have at least 90% similarity, more preferably at least 95% similarity, and still more preferably at least 96%, 97%, 98% or 99% similarity to those described above. A further embodiment of the invention relates to a polypeptide which comprises the amino acid sequence of a CCRP-1 polypeptide having an amino acid sequence which contains at least one conservative amino acid substitution, but not more than 50 conservative amino acid substitutions, not more than 40 conservative amino acid substitutions, not more than 30 conservative amino acid substitutions, and not more than 20 conservative amino acid substitutions. Also provided are polypeptides which comprise the amino acid sequence of a CCRP-1 polypeptide, having at least one, but not more than 10, 9, 8, 7, 6, 5, 4, 3, 2 or 1 conservative amino acid substitutions. By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%,97%, 98% or 99% identical to, for instance, the amino acid sequences shown in SEQ ID NO:2 can be determined conventionally using known computer programs. Such algorithms and programs include, but are by no means limited to, TBLASTN, BLASTP, FASTA, TFASTA, and CLUSTALW (Pearson and Lipman, 1988; Altschul et al., 1990; Thompson et al., 1994; Higgins et al., 1996; Altschul et al., 1990; Altschul et al., 1993). In a particularly preferred embodiment, protein and nucleic acid sequence homologies are evaluated using the Basic Local Alignment Search Tool ("BLAST"), which is well known in the art (See, e.g., Karlin and Altschul 1990; Altschul et al., 1990, 1993, 1997). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (See Gonnet et al., 1992; Henikoff and Henikoff, 1993). Less preferably, the PAM or PAM250 matrices may also be used (See, e.g., Schwartz and Dayhoff, eds, 1978). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, 1990). The BLAST programs may be used with the default parameters or with modified parameters provided by the user.

A preferred method for determining the best overall match between a query sequence (a sequence of the present invention) and a subject sequence, also referred to as a global sequence alignment, can be determined using the FASTDB computer program based on the algorithm of Brutlag et al. (1990) Comp. App. Biosci. 6:237–245. In a sequence alignment the query and subject sequences are both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group25Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N-or C-terminal deletions, not because of internal deletions, the results, in percent identity, must be manually corrected. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence. For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90-residue subject sequence is compared with a 100-residue query sequence. This time the deletions are internal so there are no residues at the N- or C-termini of the subject sequence, which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected. No other manual corrections are made for the purposes of the present invention.

The variant polypeptides described herein are included in the present invention regardless of whether they have their normal biological activity. This is because even where a particular polypeptide molecule does not have biological activity, one of skill in the art would still know how to use the polypeptide, for instance, as a vaccine or to generate antibodies. Other uses of the polypeptides of the present invention that do not have CCRP-1 activity include, inter alia, as epitope tags, in epitope mapping, and as molecular weight markers on SDS-PAGE gels or on molecular sieve gel filtration columns using methods known to those of skill in the art. As described below, the polypeptides of the present invention can also be used to raise polyclonal and monoclonal antibodies, which are useful in assays for detecting CCRP-1 protein expression or as agonists and antagonists capable of enhancing or inhibiting CCRP-1 protein function. Further, such polypeptides can be used in the yeast two-hybrid system to "capture" CCRP-1 protein binding proteins, which are also candidate agonists and antagonists according to the present invention (See, e.g., Fields et al. 1989).

CCRP-1 proteins are preferably isolated from human or mammalian tissue samples or expressed from human or mammalian genes. The CCRP-1 polypeptides of the invention can be made using routine expression methods known in the art. The polynucleotide encoding the desired polypeptide is ligated into an expression vector suitable for any convenient host. Both eukaryotic and prokaryotic host systems are used in forming recombinant polypeptides. The polypeptide is then isolated from lysed cells or from the culture medium and purified to the extent needed for its intended use. Purification is by any technique known in the art, for example, differential extraction, salt fractionation, chromatography, centrifugation, and the like. See, for example, Methods in Enzymology for a variety of methods for purifying proteins.

In addition, shorter protein fragments may be produced by chemical synthesis. Alternatively the proteins of the invention are extracted from cells or tissues of humans or non-human animals. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

Any CCRP-1 cDNA, including SEQ ID NO:1, is used to express CCRP-1 polypeptides. The nucleic acid encoding the CCRP-1 polypeptide to be expressed is operably linked to a promoter in an expression vector using conventional cloning technology. The CCRP-1 insert in the expression vector may comprise the full coding sequence for the CCRP-1 protein or a portion thereof. For example, the CCRP-1 derived insert may encode a polypeptide comprising at least 10 consecutive amino acids of the CCRP-1 protein of SEQ ID NO:2.

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence is optimized for the particular expression organism in which the expression vector is introduced, as explained by Hatfield, et al., U.S. Pat. No. 5,082,767, the disclosures of which are incorporated by reference herein in their entirety.

In one embodiment, the entire coding sequence of the CCRP-1 cDNA through the poly A signal of the cDNA are operably linked to a promoter in the expression vector. Alternatively, if the nucleic acid encoding a portion of the CCRP-1 protein lacks a methionine to serve as the initiation site, an initiating methionine can be introduced next to the first codon of the nucleic acid using conventional techniques. Similarly, if the insert from the CCRP-1 cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. The nucleic acid encoding the CCRP-1 protein or a portion thereof is obtained by PCR from a vector containing the CCRP-1 cDNA of SEQ ID NO:1 using oligonucleotide primers complementary to the CCRP-1 cDNA or portion thereof and containing restriction endonuclease sequences for Pst I incorporated into the 5' primer and BglII at the 5' end of the corresponding cDNA 3' primer, taking care to ensure that the sequence encoding the CCRP-1 protein or a portion thereof is positioned properly with respect to the poly A signal. The purified fragment obtained from the resulting PCR reaction is digested with PstI, blunt ended with an exonuclease, digested with Bgl II, purified and ligated to pXT1, now containing a poly A signal and digested with BglII.

Transfection of a CCRP-1 expressing vector into mouse NTH 3T3 cells is but one embodiment of introducting polynucleotides into host cells. Introduction of a polynucleotide encoding a polypeptide into a host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al. (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, see, e.g., U.S. Pat. No. 5,641, 670, issued Jun. 24, 1997; International Publication No. WO 96/29411, published Sep. 26, 1996; International Publication No. WO 94/12650, published Aug. 4, 1994; Koller et al., (1989); and Zijlstra et al. (1989) (The disclosures of each of which are incorporated by reference in their entireties).

In addition, polypeptides of the invention can be chemically synthesized using techniques known in the art (See, e.g., Creighton, 1983; and Hunkapiller et al., 1984). For example, a polypeptide corresponding to a fragment of a polypeptide sequence of the invention can be synthesized by use of a peptide synthesizer. Furthermore, if desired, non-classical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity. See U.S. Pat. No. 4,179,337, the disclosure of which is incororated by reference herein in its entirety. The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al. (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation, which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NON or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomenc multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences, which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925, the disclosure of which is incorporated herein by reference in its entirety). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are incorporated herein by reference in its entirety). In another embodiment, two or more polypeptides of the invention are joined through peptide linkers. Examples include those peptide linkers described in U.S. Pat. No. 5,073,627 (the disclosure of which is incorporated herein by reference in its entirety). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins, and have since been found in a variety of different proteins (Landschulz et al., 1988). Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. FEBS Letters (1994) and in U.S. patent application Ser. No. 08/446,922, hereby incorporated by reference herein in its entirety. Other peptides derived from naturally occurring trimeric proteins may be employed in preparing trimeric polypeptides of the invention. In another example, proteins of the invention are associated by interactions between Flag & polypeptide sequence contained in fusion proteins of the invention containing Flag@ polypeptide seuqence. In a further embodiment, associations proteins of the invention are associated by interactions between heterologous polypeptide sequence contained in Flag@ fusion proteins of the invention and anti Flag@ antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is incorporated herein by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is incorporated herein by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is incorporated herein by reference in its entirety). Additionally, 30 techniques known in the art may be applied to generate liposomes containing the polypeptide components desired to be contained in the multimer of the invention (see, e.g., U.S. Pat. No. 5,478,925, which is incorporated herein by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is incorporated herein by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is incorporated herein by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is incorporated herein by reference in its entirety).

Epitomes and Antibody Fusions

A preferred embodiment of the present inventionis directed to eiptope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes (See, e.g., Geysen, et al., 1983). It is particularly noted that although a particular epitope may not be immunogenic, it is nonetheless useful since antibodies can be made to both immunogenic and antigenic epitopes.

An epitope can comprise as few as 3 amino acids in a spatial conformation, which is unique to the epitope. Generally an epitope consists of at least 6 such amino acids, and more often at least 8–10 such amino acids. In preferred embodiment, antigenic epitopes comprise a number of amino acids that is any integer between 3 and 50. Fragments which function as epitopes may be produced by any conventional means (See, e.g., Houghten, R. A., 1985),also, further described in U.S. Pat. No. 4,631,211, the disclosure of which is incorporated herein by reference in its entirety. Methods for determining the amino acids which make up an epitope include x-ray crystallography, 2-dimensional nuclear magnetic resonance, and epitope mapping, e.g., the Pepscan method described by Mario H. Geysen et al. (1984); PCT Publication No. WO 84/03564; and PCT Publication No. WO 84/03506, the disclosures of which are incorporated herein by reference in their entireties. Another example is the algorithm of Jameson and Wolf, (1988) (said references incorporated by reference in their entireties). The Jameson-Wolf antigenic analysis, for example, may be performed using the computer program PROTEAN, using default parameters (Version 4.0 Windows, DNASTAR, Inc., 1228 South Park Street Madison, Wis.

Predicted antigenic epitopes are shown below. It is pointed out that the immunogenic epitope list describe only amino acid residues comprising epitopes predicted to have the highest degree of immunogenicity by a particular algorithm. Polypeptides of the present invention that are not specifically described as immunogenic are not considered non-antigenic. This is because they may still be antigenic in vivo but merely not recognized as such by the particular algorithm used. Alternatively, the polypeptides are probably antigenic in vitro using methods such a phage display. Thus, listed below are the amino acid residues comprising only preferred epitopes, not a complete list. In fact, all fragments of the polypeptides of the present invention, at least 6 amino acids residues in length, are included in the present invention as being useful as antigenic epitope. Moreover, listed below are only the critical residues of the epitopes determined by the Jameson-Wolf analysis. Thus, additional flanking residues on either the N-terminal, C-terminal, or both N- and C-terminal ends may be added to the sequences listed to generate an epitope-bearing portion at least 6 residues in length. Amino acid residues comprising other immunogenic epitopes may be determined by algorithms similar to the Jameson-Wolf analysis or by in vivo testing for an antigenic response using the methods described herein or those known in the art.

The epitope-bearing fragments of the present invention preferably comprises 6 to 50 amino acids (i.e. any integer between 6 and 50, inclusive) of a polypeptide of the present invention. Also, included in the present invention are antigenic fragments between the integers of 6 and the full length CCRP-1 sequence of the sequence listing. All combinations of sequences between the integers of 6 and the full-length sequence of a CCRP-1 polypeptide are included. The epitope-bearing fragments may be specified by either the number of contiguous amino acid residues (as a sub-genus) or by specific N-terminal and C-terminal positions (as species) as described above for the polypeptide fragments of the present invention. Any number of epitope-bearing fragments of the present invention may also be excluded in the same manner.

Antigenic epitopes are useful, for example, to raise antibodies, including monoclonal antibodies that specifically bind the epitope (See,Wilson et al., 1984; and Sutcliffe, J. G. et al., 1983). The antibodies are then used in various techniques such as diagnostic and tissue/cell identification techniques, as described herein, and in purification methods.

Similarly, immunogenic epitopes can be used to induce antibodies according to methods well known in the art (See, Sutcliffe et al., supra; Wilson et al., supra; Chow, M. et al.;(1985) and Bittle, F. J. et al., (1985). A preferred immunogenic epitope includes the natural CCRP-1 protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.).

Epitope-bearing polypeptides of the present invention are used to induce antibodies according to methods well known in the art including, but not limited to, in vivo immunization, in vitro immunization, and phage display methods (See, e.g., Sutcliffe, et al., supra; Wilson, et al., supra, and Bittle, et al., 1985). If in vivo immunization is used, animals may be immunized with free peptide; however, anti-peptide antibody titer may be boosted by coupling of the peptide to a macromolecular carrier, such as keyhole limpet hemacyanin. (KLH) or tetanus toxoid. For instance, peptides containing cysteine residues may be coupled to a carrier using a linker such as -maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins (See, e.g., EPA 0,394,827; and Traunecker et al., 1988, the disclosures of which are incorporated herein by reference in their entireties). Fusion proteins that have a disulfide-linked dimeric structure due to the IgG portion can also be more efficient in binding and neutralizing other molecules than monomeric polypeptides or fragments thereof alone (See, e.g., Fountoulakis et al., 1995). Nucleic acids encoding the above epitopes can also be recombined with a gene of interest as an epitope tag to aid in detection and purification of the expressed polypeptide.

Additonal fusion proteins of the invention may be generated through the techniques of gene-shuffling, motif-shuffling, exon-shuffling, or codon-shuffling (collectively referred to as "DNA shuffling"). DNA shuffling may be employed to modulate the activities of polypeptides of the present invention thereby effectively generating agonists and antagonists of the polypeptides. See, for example, U.S. Pat. Nos. 5,605,793; 5,811,238; 5,834,252; 5,837,458; and Patten, P. A., et al., (1997); Harayama, S., (1998); Hansson, L. O., et al (1999); and Lorenzo, M. M. and Blasco, R., (1998). (Each of these documents are hereby incorporated herein by reference in their entireties). In one embodiment, one or more components, motifs, sections, parts, domains, fragments, etc., of coding polynucleotides of the invention, or the polypeptides encoded thereby may be recombined with one or more components, motifs, sections, parts, domains, fragments, etc. of one or more heterologous molecules.

Preferred CCRP-1 immunogenic epitopes:
Ile-42 to Tyr-36
Arg-28 to Arg-23
Tyr18 to Ala28
Ser46 to Lys52
Cys86 to Gly93
Gly143 to Val149
Gln178 to Arg186
Arg199 to Val205

Antibodies

The present invention further relates to antibodies and T-cell antigen receptors (TCR), which specifically bind the polypeptides, and more specifically, the epitopes of the polyepeptides of the present invention. The antibodies of the present invention include IgG (including IgG1, IgG2, IgG3, and IgG4), IgA (including IgA1 and IgA2), IgD, IgE, or IgM, and IgY. As used herein, the term "antibody" (Ab) is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, A. et al. (1991); U.S. Pat. Nos. 5,573,920, 4,474,893, 5,601,819, 4,714,681, 4,925,648; Kostelny, S. A. et al. (1992), the disclosures of which are incorporated herein by reference in their entireties.

Antibodies of the present invention may be described or specified in terms of the epitope(s) or epitope-bearing portion(s) of a polypeptide of the present invention, which are recognized or specifically bound by the antibody. In the case of proteins of the present invention secreted proteins, the antibodies may specifically bind a full-length protein encoded by a nucleic acid of the present invention, a mature protein (i.e., the protein generated by cleavage of the signal peptide) encoded by a nucleic acid of the present invention, a signal peptide encoded by a nucleic acid of the present invention, or any other polypeptide of the present invention. Therefore, the epitope(s) or epitope bearing polypeptide portion(s) may be specified as described herein, e.g., by N-terminal and C-terminal positions, by size in contiguous amino acid residues, or otherwise described herein (including the sequence listing). Antibodies which specifically bind any epitope or polypeptide of the present invention may also be excluded as individual species. Therefore, the present invention includes antibodies that specifically bind specified polypeptides of the present invention, and allows for the exclusion of the same.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, e.g., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples (See, e.g., Harlow et al., 1988). (Incorporated herein by reference in their entireties).

The antibodies of the present invention may be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387, the disclosures of which are incorporated herein by reference in their entireties.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not limited to antibodies produced through hybridoma technology. The term "antibody" refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. The term "monoclonal antibody" refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (See, erg., Harlow et al. 1988); Hammerling, et al, 1981). (Said references incorporated herein by reference in their entireties). Fab and F(ab')2 fragments may be produced, for example, from hybridoma-produced antibodies by proteolytic cleavage, using enzymes such as papain (to produce Fab fragments) or pepsin (to produce F(ab')2 fragments).

Alternatively, antibodies of the present invention can be produced through the application of recombinant DNA technology or through synthetic chemistry using methods known in the art. For example, the antibodies of the present invention can be prepared using various phage display methods known in the art. In phage display methods, functional antibody domains are displayed on the surface of a phage particle, which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman U. et al. (1995); Ames, R. S. et al. (1995); Kettleborough, C. A. et al. (1994); Persic, L. et al. (1997); Burton, D. R. et al. (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated herein by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' F(ab)2 and F(ab')2 fragments can also be employed using methods known in the art such as those disclosed in WO 92/22324; Mullinax, R. L. et al. (1992); and Sawai, H. et al. (1995); and Better, M. et al. (1988) (said references incorporated herein by reference in their entireties).

Examples of techniques which can be used to produce single-chain Fvs and antibodies include those described in U.S. Pat. Nos. 4,946,778 and 5,258,498; Huston et al. (1991); Shu, L. et al. (1993); and Skerra, A. et al. (1988), the disclosures of which are incorporated herein by reference in their entireties. For some uses, including in vivo use of antibodies in humans and in vitro detection assays, it may be preferable to use chimeric, humanized, or human antibodies. Methods for producing chimeric antibodies are known in the art. See e.g., Morrison, (1985); Oi et al., (1986); Gillies, S. D. et al. (1989); and U.S. Pat. No. 5,807,715, the disclosures of which are incorporated herein by reference in their entireties. Antibodies can be humanized using a variety of techniques including CDR-grafting (EP 0 239 400; WO 91/09967; U.S. Pat. Nos. 5,530,101; and 5,585,089, the disclosures of which are incorporated herein by reference in their entireties), veneering or resurfacing, (EP 0 592 106; EP 0 519 596; Padlan E. A., 1991; Studnicka G. M. et al., 1994; Roguska M. A. et al., 1994, the disclosures of which are incorporated herein by reference in their entireties), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; WO 98/46645; WO 98/50433; WO 98/24893; WO 96/34096; WO 96/33735; and WO 91/10741 (said references incorporated herein by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art (See e.g., Harbor et al. supra; WO 93/21232; EP 0 439 095; Naramura, M. et al. 1994; U.S. Pat. No. 5,474,981; Gillies, S. O. et al., 1992; Fell, H. P. et al., 1991) (said references incorporated herein by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, CH1 domain, CH2 domain, and CH3 domain or any combination of whole domains or portions thereof. The polypeptides of the present invention may be fused or conjugated to the above antibody portions to increase the in vivo half-life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi, A. et al. (1991); Zheng, X. X. et al. (1995); and Vil, H. et al. (1992) (said references incorporated herein by reference in their entireties).

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies, which do not prevent ligand binding but prevent receptor activation. Receptor activation (i.e., signaling) may be determined by techniques described herein or otherwise known in the art. Also include are receptor-specific antibodies which both prevent ligand binding and receptor activation. Likewise, included are neutralizing antibodies that bind the ligand and prevent binding of the ligand to the receptor, as well as antibodies that bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng, B. et al. (1998); Chen, Z. et al. (1998); Harrop, J. A. et al. (1998); Zhu, Z. et al. (1998); Yoon, D. Y. et al. (1998); Prat, M. et al. (1998) J.; Pitard, V. et al. (1997); Liautard, J. et al. (1997); Carlson, N. G. et al. (1997) J.; Taryman, R. E. et al. (1995); Muller, Y. A. et al. (1998); Bartunek, P. et al. (1996) (said references incorporated herein by reference in their entireties).

As discussed above, antibodies of the polypeptides of the invention can, in turn, be utilized to generate anti-idiotypic antibodies that "mimic" polypeptides of the invention using techniques well known to those skilled in the art (See, e.g. Greenspan and Bona (1989); and Nissinoff(1991). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and therby block its biological activity, The invention also concerns a purified or isolated antibody capable of specifically binding to a mutated CCRP-1 protein or to a fragment or variant thereof comprising an epitope of the mutated CCRP-1 protein. In another preferred embodiment, the present invention concerns an antibody capable of binding to a polypeptide comprising at least 10 consecutive amino acids of a CCRP-1 protein and including at least one of the amino acids which can be encoded by the trait causing mutations.

Non-human animals or mammals, whether wild-type or transgenic, which express a different species of CCRP-1 than the one to which antibody binding is desired, and animals which do not express CCRP-1 (i.e. a CCRP-1 knock out animal as described herein) are particularly useful for preparing antibodies. CCRP-1 knock out animals will recognize all or most of the exposed regions of a CCRP-1 protein as foreign antigens, and therefore produce antibodies with a wider array of CCRP-1 epitopes. Moreover, smaller polypeptides with only 10 to 30 amino acids may be useful in obtaining specific binding to any one of the CCRP-1 proteins. In addition, the humoral immune system of animals which produce a species of CCRP-1 that resembles the antigenic sequence will preferentially recognize the differences between the animal's native CCRP-1 species and the antigen sequence, and produce antibodies to these unique sites in the antigen sequence. Such a technique will be particularly useful in obtaining antibodies that specifically bind to any one of the CCRP-1 proteins.

Antibody preparations prepared according to either protocol are useful in quantitative immunoassays which determine concentrations of antigen-bearing substances in biological samples; they are also used semi-quantitatively or qualitatively to identify the presence of antigen in a biological sample. The antibodies may also be used in therapeutic compositions for killing cells expressing the protein or reducing the levels of the protein in the body.

The antibodies of the invention may be labeled by any one of the radioactive, fluorescent or enzymatic labels known in the art.

Consequently, the invention is also directed to a method for detecting specifically the presence of a CCRP-1 polypeptide according to the invention in a biological sample, said method comprising the following steps:

a) bringing into contact the biological sample with a polyclonal or monoclonal antibody that specifically binds a CCRP-1 polypeptide of the present invention; and b) detecting the antigen-antibody complex formed.

The invention also concerns a diagnostic kit for detecting in vitro the presence of a CCRP-1 polypeptide according to the present invention in a biological sample, wherein said kit comprises:

a) a polyclonal or monoclonal antibody that specifically binds a CCRP-1 polypeptide of the present invention, optionally labeled;

b) a reagent allowing the detection of the antigen-antibody complexes formed, said reagent carrying optionally a label, or being able to be recognized itself by a labeled reagent, more particularly in the case when the above-mentioned monoclonal or polyclonal antibody is not labeled by itself Methods of Detection, Screening, and Diagnosis In another embodiment, the sequences described herein can be used to detect CCRP-1 or polynucleotides encoding CCRP-1 in a sample. For example, a labeled polynucleotide probe having all or a functional portion of the nucleotide sequence of a CCRP-1 polynucletide can be used in a method to detect a CCRP-1 polynucleotide in a sample. In one embodiment, the sample is treated to render the polynucleotides in the sample available for hybridization to a polynucleotide probe, which can be DNA or RNA. The resulting treated sample is combined with a labeled polynucleotide probe having all or a portion of the nucleotide sequence of the CCRP-1 cDNA or genomic sequence, under conditions appropriate for hybridization of complementary sequences to occur. Detection of hybridization of polynucleotides from the sample with the labeled nucleic probe indicates the presence of CCRP-1 polynucleotides in a sample. The presence of CCRP-1 mRNA is indicative of CCRP-1 expression. Such a method can be used, for example, as a screen for normal or abnormal fatty acid metabolism.

Alternatively, a method of detecting CCRP-1 in a sample can be accomplished using an antibody directed against a CCRP-1 polypeptide of the present invention or a portion of a CCRP-1 polypeptide. Detection of specific binding to the antibody indicates the presence of a CCRP-1 polypeptide in the sample (e.g., ELISA). This could reflect a pathological state associated with CCRP-1 and, thus, can be used diagnostically. The sample for use in the methods of the present invention includes a suitable sample from, for example, a mammal, particularly a human. For example, the sample can be blood, skeletal muscle or brown adipose tissue.

The present invention further relates to methods of identifying individuals or non-human animals at increased risk for developing, or present state of having, certain diseases/disorders, including hyperinsulinemia, glucose intolerance, type II diabetes, obesity, syndrome X, immunological dysfunction and body temperature dysfunction, and heart disease. One such method comprises: (a) obtaining from a mammal (e.g. a preobese human or pre-heart diseased human) a biological sample, (b) detecting the presence in the sample of a CCRP-1 gene product (mRNA or protein) and (c) comparing the amount of the gene product present in the sample with that in a control sample. In preferred embodiments, the biological sample is taken after the consumption of a high fat meal or after a specified period of fasting. In accordance with this method, the presence in the sample of altered (e.g. diminished) levels of CCRP-1 gene product indicates that the subject is predisposed to the above-indicated diseases/disorders. Biological samples suitable for use in this method include biological fluids such as blood. Tissue samples (e.g. biopsies) can also be used in the method of the invention, including samples derived from muscle or fat. Cell cultures or cell extracts derived, for example, from tissue biopsies can also be used. The detection step of the present method can be affected using standard protocols for protein/mRNA detection. Examples of suitable protocols include Northern blot analysis, immunoassays (e.g. RIA, Western blots, immunohistochemical analyses), and PCR.

The present invention also relates to methods of identifying individuals having elevated or reduced levels of CCRP-1, which individuals are likely to benefit from therapies to suppress or enhance CCRP-1 expression, respectively. As indicated above, a biological sample from an obese, preobese, heart diseased, or pre-heart diseased subject can be screened for the presence of diminished levels of CCRP-1 gene product, particularly in response to high fat intake, the presence of depressed levels of the gene product, relative to a normal population (standard), being indicative of predisposition to or as a present indication of obesity, type II diabetes, syndrome X, or heart disease. Such individuals would be candidates for therapics, e.g., anti-obesity therapy (e.g. treatment with appetite suppressants). The identification of elevated levels of CCRP-1 in a wasting patient (e.g. a cancer, AIDS or anorexia patient) would be indicative of an individual that would benefit from treatment with agents that suppress CCRP-1 expression or activity. The identification of low levels of CCRP-1 in a hypothermic patient or obese patient would be indicative of an individual that would benefit from agents that induce CCRP-1 expression or activity.

The present invention also relates to a kit that can be used in the detection of CCRP-1 expression products. The kit can comprise a compound that specifically binds CCRP-1 (e.g. binding proteins) (e.g., antibodies or binding fragments thereof (e.g. F(ab')2 fragments) or CCRP-1 mRNA (e.g. a complementary probe or primer), for example, disposed within a container means. The kit can further comprise ancillary reagents, including buffers and the like. The diagnostic methodologies described herein are applicable to both humans and non-human mammals.

Figure 1B:
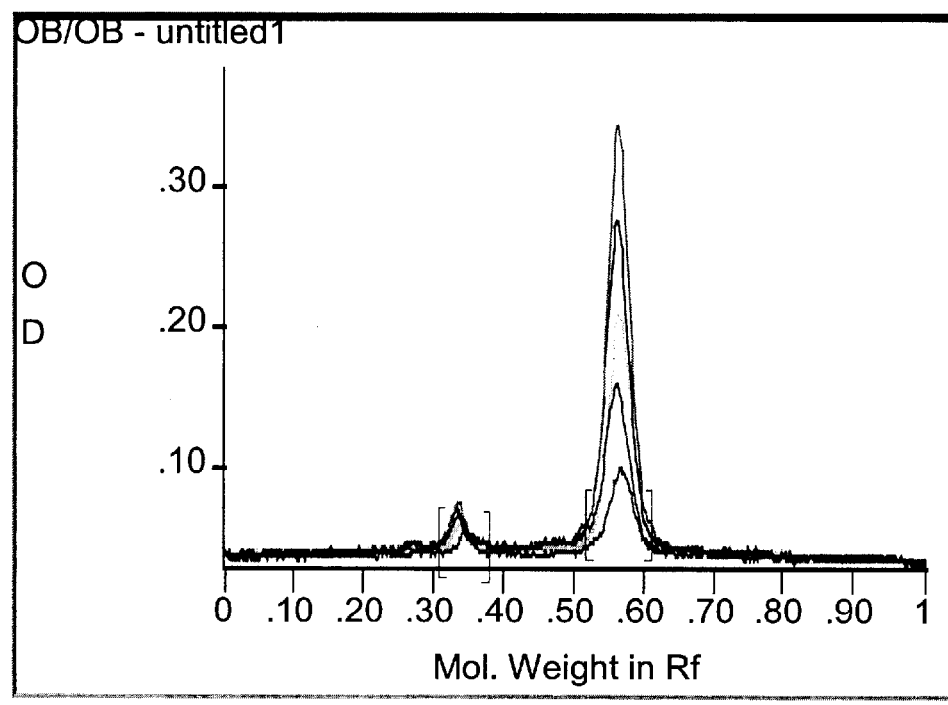

To demonstrate how the detection of CCRP-1 gene products can be used in methods of identifying individuals or non-human animals at increased risk for developing, or present state of having certain diseases/disorders, including hyperinsulinemia, glucose intolerance, type II diabetes, obesity, syndrome X, immunological dysfunction and body temperature dysfunction, and heart disease and which individuals are likely to benefit from therapies to enhance CCRP-1 expression, Northern blot analysis was performed as follows. mRNA was extracted from livers of normal mice (C57N), knockout mice for the OB ligand (OB/OB), knockout mice for the OB receptor (DB/DB), cafeteria fed mice (mice fed a high fat diet), and New Zeland Obese (NZO) mice. Northern blot analysis was then performed using labeled antisense CCRP-1 RNA using methods well known in the art. The results, FIG. 1, demonstrate a significant increase in CCRP-1 gene expression in OB/OB (lane 2), DB/DB (lane 3), and cafeteria fed (lane 4) mice compared to normal mice (C57N) (lane 1). These results suggest that OB/OB, DB/DB, and mice fed a high fat diet are at risk for developing or are in the present state of having one of the above diseases/disorders and would benefit from therapies aimed at increasing CCRP-1 levels.

Compounds that Modulate CCRP-1 Expression or Activity

The present invention also relates to methods of screening compounds for their ability to modulate (e.g. increase or inhibit) the activity or expression of CCRP-1. More specifically, the present invention relates to methods of testing compounds for ability either to increase or to decrease expression or activity of CCRP-1. The assays are performed in vitro or in vivo. In vitro, cells expressing CCRP-1 are incubated in the presence and absence of the test compound. By determining the level of CCRP-1 expression in the presence of the test compound (using, for example, Northern blots, immunoassays (e.g. RIA, western blots or immunohistochemistry or PCR), or the level of CCRP-1 activity in the presence of the test compound, compounds can be identified that suppress or enhance CCRP-1 expression or activity. Alternatively, constructs comprising the CCRP-1 promoter operably linked to a reporter gene (e.g. luciferase, chloramphenicol acetyl transferase, LacZ, green fluorescent protein, etc.) can be introduced into host cells and the effect of the test compounds on expression of the reporter gene detected. Cells suitable for use in the foregoing assays include, but are not limited to, lymphoblasts, myocytes, adipocytes and hepatic cells, more specifically, C2C12 cells, 3T3 cells of adipocyte lineage, HIB-1B cells, rodent hepatoma cells, HepG2cells, and B7 cells.

Compounds that suppress or enhance CCRP-1 expression can also be identified using in vivo screens. In these assays, the test compound is administered (e.g. IV, IP, IM, orally, or otherwise), to the animal, for example, at a variety of dose levels. The effect of the compound on CCRP-1 expression is determined by comparing CCRP-1 levels, for example, in blood, muscle or fat tissue, using Northern blots, immunoassays, PCR, etc., as described above. Suitable test animals include rodents (e.g., mice and rats), primates, dogs and swine. Humanized mice can also be used as test animals, that is mice in which the endogenous mouse protein is ablated (knocked out) and the homologous human protein added back by standard transgenic approaches. Such mice express only the human form of a protein. Humanized mice expressing only the human CCRP-1 can be used to study in vivo responses of weight loss, fever, cachexia in response to potential agents regulating CCRP-1 protein or mRNA levels. As an example, transgenic mice have been produced carrying the human apoE4 gene. They are then bred with a mouse line that lacks endogenous apoE, to produce an animal model carrying human proteins believed to be instrumental in development of Alzheimers pathology. Such transgenic animals are useful for dissecting the biochemical and physiological steps of disease, and for development of therapies for disease intervention (Loring, et al, 1996) (incorporated herein by reference in its entirety).

Compounds that suppress or enhance CCRP-1 activity can be identified by contacting CCRP-1 with the test compound under conditions such that the compound can interact with (e.g. bind to) the protein. A system such as the yeast expression system described in PCT publication WO 98/31396, the disclosure of which is incorporated herein by reference in its entirety, can be used. In such a system, the effect of the test compound on CCRP-1 activity can be determined, for example, by analyzing the alteration in membrane potential (e.g. using flow cytometry). (Comparable studies can be carried out in vivo by administering the test compound and measuring its effect on respiration and/or body temperature). In addition, using cellular systems such as the two-hybrid system, proteins can be identified that interact with CCRP-1 (Fields et al, 1989; Chien et al, 1991) (each incorporated herein by reference in its entirity), Using in vivo (or in vitro) systems, it may be possible to identify compounds that exert a tissue specific effect, for example, that increase CCRP-1 expression or activity only in fat or muscle or cells. Screening procedures such as those described above are useful for identifying agents for their potential use in pharmacological intervention strategies. Agents that enhance CCRP-1 expression or activity can be used to treat disorders such as, hyperinsulinemia, glucose intolerance, diabetes, obesity, syndrome X and heart disease. Compounds that suppress CCRP-1 expression or inhibit its activity can be used to treat wasting associated, for example, with cancer, AIDS, cachexia and anorexia. Agents that suppress CCRP-1 expression or inhibit its activity may also be used to induce hypothermia, for example, when advantageous in surgical settings, including transplantation. Such agents can also be used to block hyperthermia, for example, during thyroid storm. Compounds that enhance CCRP-1 expression or stimulate its activity may also be used to treat hypothermia or high level of fatty acid blood levels.

Another method of screening for compounds that modulate CCRP-1 activity is by measuring the effects of test compounds on mitochondrial membrane potential in a host cell. In addition, evaluation of mitochondrial respiration can also be performed in the host cell. In one embodiment, the present invention relates to a method of identifying an agent which alters CCRP-1 activity, wherein a nucleic acid construct comprising nucleic acid which encodes a mammalian CCRP-1 polypeptide is introduced into a host cell. The host cells produced are maintained under conditions appropriate for expression of the encoded mammalian CCRP-1 polypeptides, whereby the nucleic acid is expressed. The host cells are then contacted with a compound to be assessed (an agent) and the mitochondrial electrical potential (mitochondrial membrane potential) of the cells is detected in the presence of the compound to be assessed. Detection of a change in mitochondrial electrical potential in the presence of the agent indicates that the agent alters CCRP-1 activity. In a particular embodiment, the invention relates to a method of identifying an agent which is an activator of CCRP-1 activity wherein a nucleic acid construct comprising nucleic acid which encodes a mammalian CCRP-1 polypeptide is introduced into a host cell. The host cells produced are maintained under conditions appropriate for expression of the encoded mammalian CCRP-1 polypeptide, whereby the nucleic acid is expressed. The host cells are then contacted with a compound to be assessed (an agent) and the mitochondrial electrical potential of the cells is detected in the presence of the compound to be assessed. Detection of a decrease or reduction of mitochondrial electrical potential in the presence of the agent indicates that the agent activates CCRP-1 activity.

In another embodiment, the invention relates to a method of identifying an agent which is an inhibitor of CCRP-1 activity, wherein a nucleic acid construct comprising nucleic acid which encodes a mammalian CCRP-1 polypeptide is introduced into a host cell. The host cells produced are maintained under conditions appropriate for expression of the encoded mammalian CCRP-1 polypeptide, whereby the nucleic acid is expressed. The host cells are then contacted with a compound to be assessed (an agent) and the mitochondrial electrical potential of the cells is detected in the presence of the compound to be assessed. Detection of an increase of mitochondrial electrical potential in the presence of the agent indicates that the agent inhibits CCRP-1 activity. Detection of a change in mitochondrial electrical potential can be performed using a variety of techniques. For example, a change in mitochondrial electrical potential can be detected by measuring fluorescence of recombinant cells expressing a CCRP-1 polypeptide. Decrease of fluorescence in the presence of the test compound, indicates a decrease of mitochondrial membrane potential, and vice versa for cases where fluorescence is increased. That is, increase of fluorescence in the presence of the test compound indicates an increase of mitochondrial electrical potential. If decrease in fluorescence is observed in CCRP-1 expressing cells, but not in control cells, then the test compound is an activator of CCRP-1. If an increase in fluorescence is observed in CCRP-1 expressing cells, but not in control cells, then the test compound is an inhibitor of CCRP-1.

In a particular embodiment a high throughput screen can be used to identify agents that activate (enhance) or inhibit CCRP-1 activity (See e.g., PCT publication WO 98/45438, incorporated herein by reference in its entirety). For example, the method of identifying an agent which alters CCRP-1 activity can be performed as follows. A nucleic acid construct comprising polynucleotide which encodes a mammalian CCRP-1 polypeptide is introduced into a host cell to produce recombinant host cells. The recombinant host cells produced are maintained under conditions appropriate for expression of the encoded mammalian CCRP-1 polypeptide, whereby the nucleic acid is expressed. A fluorescent dye and the compound to be assessed are added to the recombinant host cells; the resulting combination is referred to as a test sample. Fluorescence is detected. A decrease of fluorescence in the presence of the test compound occurs with a decrease in the mitochondrial electrical potential of the cells, which indicates that the agent is an activator of CCRP-1. Conversely, an increase of fluorescence in the presence of the test compound occurs with an increase in the mitochondrial electrical potential of the cells, which indicates that the agent is an inhibitor of CCRP-1. Suitable dyes for use in this embodiment of the invention include, for example, JC-1, rhodamine 123, or tetramethylhydrosamine. A control can be used in the methods of detecting agents which alter CCRP-1 activity. For example, the control sample includes the same reagents but lacks the compound or agent being assessed; it is treated in the same manner as the test sample.

Also encompassed by the present invention is an agent which interacts with CCRP-1 directly or indirectly, and inhibits or enhances CCRP-1 expression and/or function. In one embodiment, the agent is an inhibitor which interferes with CCRP-1 directly (e.g., by binding CCRP-1) or indirectly (e.g., by blocking the ability of CCRP-1 to function in fatty acid metabolism). In a particular embodiment, an inhibitor of CCRP-1 protein is an antibody specific for CCRP-1 protein or a functional portion of CCRP-1; that is, the antibody binds a CCRP-1 polypeptide. For example, the antibody can be specific for the protein encoded by the amino acid sequence of human CCRP-1 (SEQ ID NO: 2), mouse CCRP-1 or portions thereof. Alternatively, the inhibitor can be an agent other than an antibody (e.g., small organic molecule, protein or peptide) which binds CCRP-1 and blocks its activity. For example, the inhibitor can be an agent which mimics CCRP-1 structurally, but lacks its function. Alternatively, it can be an agent which binds to or interacts with a molecule which CCRP-1 normally binds with or interacts with, thus blocking CCRP-1 from doing so and preventing it from exerting the effects it would normally exert.

In another embodiment, the agent is an enhancer (activator) of CCRP-1 which increases the activity of CCRP-1 (increases the effect of a given amount or level of CCRP-1), increases the length of time it is effective (by preventing its degradation or otherwise prolonging the time during which it is active) or both either directly or indirectly. For example, CCRP-1 polynucleotides and polypeptides can be used to identify anti-obesity drugs which enhance CCRP-1 to induce fatty acid metabolism with the result that fatty acid blood levels are reduced.

The CCRP-1 sequences of the present invention can also be used to generate nonhuman gene knockout animals, such as mice, which lack a CCRP-1 gene or transgenically overexpress CCRP-1. For example, such CCRP-1 gene knockout mice can be generated and used to obtain further insight into the function of CCRP-1 as well as assess the specificity of CCRP-1 activators and inhibitors. Also, over expression of CCRP-1 (e.g., human CCRP-1) in transgenic mice can be used as a means of creating a test system for CCRP-1 activators and inhibitors (e.g., against human CCRP-1). In addition, the CCRP-1 gene can be used to clone the CCRP-1 promoter/enhancer in order to identify regulators of CCRP-1 transcription. CCRP-1 gene knockout animals include animals which completely or partially lack the CCRP-1 gene and/or CCRP-1 activity or function. As described herein, it is likely that CCRP-1 plays a role in controlling protein wasting and production of gluconeogenic precursors by skeletal muscle via transport of one or more metabolites, which indicates that inhibitors of CCRP-1 can be used as a means of curtailing muscle wasting due to, for example, infection, (e.g., human immunodeficiency virus) cancer, tumor cachexia, muscle diseases (e.g., muscular dystrophy) or as a possible treatment for non-insulin dependent diabetes mellitus (NIDDM). Thus the present invention relates to a method of inhibiting (partially or completely) protein catabolism in a mammal (e.g., human) comprising administering to the mammal an effective amount-of an inhibitor of CCRP-1. The invention also relates to a method of enhancing protein catabolism in a mammal comprising administering to the mammal an effective amount of an enhancer CCRP-1. Also encompassed by the present invention is a method of inhibiting muscle wasting in a mammal comprising administering an effective amount of an enhancer of CCRP-1 to the mammal.

Pharmaceutical and Physiologically Acceptable Compositions

The present invention also relates to pharmaceutical or physiologically acceptable compositions comprising, as active agent, the polypeptides, nucleic acids or antibodies of the invention. The invention also relates to compositions comprising, as active agent, compounds selected using the above-described screening protocols. Such compositions include the active agent in combination with a pharmaceutical or physiologically acceptablely acceptable carrier. In the case of naked DNA, the "carrier" may be gold particles. The amount of active agent in the composition can vary with the agent, the patient and the effect sought. Likewise, the dosing regimen can vary depending on the composition and the disease/disorder to be treated.

A number of studies have demonstrated that brown adipose tissue plays an important role in regulating energy balance in rodents (Himms-Hagen, J., 1989). The tissue is highly specialized for stimulated energy expenditure with a rich vascular supply, dense sympathetic innervation, and numerous mitochondria. Importantly, brown adipocytes are further distinguished from other cell types by their expression of multiple uncoupling polypeptides. These features make brown fat ideally suited to regulated fatty acid metabolism. In contrast to rodents, brown adipose tissue in large mammals is relatively limited and therefore brown fat may not be a significant regulator of human energy expenditure. A number of studies in humans have implicated skeletal muscle as an important mediator of adaptive fatty acid metabolism in humans (Astrup, A., et al., 1985,1989; Zurlo, F., et al., 1990; Simonsen, L., et al. 1992; and Spraul, M., et al., 1993). Approximately 80% of the variance in resting energy expenditure between individuals can be accounted for by differences in fat-free mass (Ravussin E., et al., 1992), much of which is skeletal muscle. Similarly, a perfused fore arm study has demonstrated that differences in skeletal muscle energy expenditure account for much of the variation in metabolic rate observed between individuals (Zurjo, F., et al., 1990). Regulated energy expenditure in skeletal muscle is controlled, in large part, by sympathetic stimulation (Astrup, A., et-35-al., 1985; Astrup, A., et-29-al., 1989; Simonsen, L., et al., 1992; Spraul, M., et al., 1993). It is interesting to note that brown fat and skeletal muscle have many features in common: a rich blood supply, a dense sympathetic innervation, and abundant mitochondria. The heart continuously expends large amounts of energy in order to maintain blood circulation. In view of this, it is probably significant whether CCRP-1 is expressed in cardiac tissue as to its function as either a translocase or uncoupler. This is especially true given the general tendency for non-contractile muscle-specific genes to be expressed in both striated muscle types (skeletal and cardiac). Abundant expression of CCRP-1 in two thermogenic tissues, skeletal muscle and brown fat, and relative lack of expression in other sites such as the heart, would suggest that CCRP-1 is an important molecular mediator of thermogenesis, and hence uncoupling acitivty. Thus, the present invention provides for anti-obesity drug development wherein the CCRP-1 polynucleotides and protein can be used to identify, for example, enhancers (activators) of CCRP-1 which can be used to induce uncoupling.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co. Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through a combination of active compounds with solid excipient, suiting mixture is optionally grinding, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titaniumdioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquidpolyethylene glycol with or without stabilizers.

Pharmaceutical formulations suitable for parenteral administration may be formulated in aqueous solutions, preferably in physiologically compatible buffers such as Hanks solution, Ringer's solution, or physiologically buffered saline. Aqueous injection suspensions may contain substances which increase the viscosity of the suspension, such as sodium carboxymethylcellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of CCRP-1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example CCRP-1 or fragments thereof, antibodies of CCRP-1, agonists, antagonists or inhibitors of CCRP-1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions maybe administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Methods of Treating CCRP-1 Related Disorders

The present invention further relates to methods of treating diseases/disorders such as hyperinsulinemia, glucose intolerance, diabetes, obesity, syndrome X, heart disease, cancer and hypothermia by increasing CCRP-1 activity and/or expression. The invention also relates to methods of treating inflammation, anorexia and wasting (cachexia)(e.g. associated with cancer or AIDS), of reducing fever and blocking hyperthermia (e.g. thyroid storm) and to methods of inducing hypothermia (e.g. when advantageous for surgery and transplant), by decreasing CCRP-1 activity and or expression. These methodologies can be effected using compounds selected using screening protocols such as those described above and/or by using the gene therapy and antisense approaches described in the art and herein. Gene therapy can be used to effect targeted expression of CCRP-1, for example, in fat tissue and muscle to reduce fat depots or in cancer cells to cause thermo destruction or metabolic collapse/death of the cells. The CCRP-1 coding sequence can be cloned into an appropriate expression vector and targeted to a particular cell type(s) to achieve efficient, high level expression. Introduction of the CCRP-1 coding sequence into target cells can be achieved, for example, using particle mediated DNA delivery, (William et al, 1991; and Haynes, 1996), direct injection of naked DNA, (Levy et al., 1996; and Feigner, 1996), or viral vector mediated transport (Smith et al., 1996). Tissue specific effects can be achieved, for example, in the case of virus mediated transport by using viral vectors that are tissue specific, or by the use of promoters that are tissue specific (e.g. leptin and aP2 promoters can be used to achieve expression in white adipose tissue and the myosin light chain kinase promoter can be used to achieve expression in skeletal muscle. (See Warden et al, In Regulation of Body Weight: biological and behavioral mechanisms, C. Bouchard and G. A. Bray, eds. West Sussex; John Wiley & Sons Ltd., pp. 285–305). The above references are incorporated herein in their entirety.

Combinatorial approaches can also be used to ensure that the CCRP-1 coding sequence is activated in the target tissue (Butt et al, 1995; and Hart, 1996). Antisense oligonucleotides complementary to CCRP-1 mRNA can be used to selectively diminish or ablate the expression of the protein, for example, at sites of inflammation. More specifically, antisense constructs or antisense oligonucleotides can be used to inhibit the production of CCRP-1 in high expressing cells (spleen, thymus, leuckocytes, bone marrow and stomach). Antisense mRNA can be produced by transfecting into target cells an expression vector with the CCRP-1 gene sequence, or portion thereof, oriented in an antisense direction relative to the direction of transcription. Appropriate vectors include viral vectors, including retroviral, adenoviral, and adeno-associated viral vectors, as well as nonviral vectors. Tissue specific promoters can be used (e.g. leptin gene promoter oraP2 gene promoter specific for adipose cells, muscle creatine kinase promoter specific for skeletal muscle and lymphoid cell promoters). Alternatively, antisense oligonucleotides can be introduced directly into target cells to achieve the same goal. (See also other delivery methodologies described above in connection with gene therapy.). Oligonucleotides can be selected/designed to achieve a high level of specificity (Matteucci et al., 1996). It has been recently demonstrated that increased $O_2$ consumption associated with cachexia of malignancy can be attenuated by indomethacin, a cyclooxygenase inhibitor. This is thought to be due to inhibition of prostaglandin production (Roe et al, 1997). Thus, agents that block CCRP-1 expression and/or activity can be expected to be useful in the treatment of cachexia. The therapeutic methodologies described herein are applicable to both human and non-human mammals (including cats and dogs). The above references are incorporated herein in their entirety.

Physiological Acceptable Compositions and Methods for Increasing the Amount of Fatty Acids Metabolized in vitro or in vivo The present invention further relates to a device, physiological acceptable composition and method for metabolizing fatty acids in an animal or individual (host) thereby reducing an individual's blood levels of fatty acids and alternatively, in addition, reducing the level of, or reducing the increase in, white adipose tissue. More particularly, the inventive device is an extracorporeal device for metabolizing fatty acids comprising a semipermeable membrane having a first and a second side and having a molecular weight cutoff of at least 10,000 daltons, an oxidizing component located adjacent to the first side of the semipermeable membrane comprising an enzyme system with necessary cofactors, brown fat mitochondria or whole cell cultures of brown adipose cells of any species or cells transfected with a construct comprising a CCRP-1 polynucleotide sequence alone or combined with a heterologous uncoupling protein (UCP) polynucleotide sequence, referred to here after as CCRP-1/UCP, each regulated by an appropriate promoter sequence (e.g., MMTV, SV40, CMV intermediate early, etc.), either combined on a single vector or on separate vectors, wherein the oxidizing component is capable of oxidizing fatty acids, and a means for circulating blood from the host to the second side of the semipermeable membrane for triglyceride hydrolysis and diffusion of free fatty acids to the first side of the semipermeable membrane for oxidation of fatty acids and returning treated blood to the host. Preferably, the oxidizing component comprises a culture of brown fat cells or other eukaryotic cells transfected with a gene encoding a CCRP-1 polypeptide or CCRP-1/UCP polypeptide(s) in an expression vector. Preferably the semipermeable membrane has a lipoprotein lipase embedded therein.

The present invention further provides a physiologically acceptable composition for metabolizing fatty acids comprising a culture of brown fat cells or CCRP-1 or CCRP-1/UCP transfected cells encapsulated in a porous growth matrix and having a semipermeable membrane encapsulating the porous growth matrix. The semipermeable membrane has a molecular weight cutoff of at least 10,000 daltons and, preferably, a lipoprotein lipase embedded therein. Preferably, the semipermeable membrane comprises a tubular membrane having two ends, filled with brown fat cells in the porous growth matrix and sealed at both ends prior to subcutaneous, intramuscularor, or intraperitoneal implantation. Preferably the porous growth matrix comprises alginate beads or another complex polysaccharide porous matrix suitable for cellular growth and metabolism.

The present invention further provides a physiologically acceptable composition for metabolizing fatty acids comprising a mammalian cell stably transfected with a DNA sequence(s) coding for a CCRP-1 or CCRP-1/UCP polypeptides, wherein the transfected mammalian cell transcribes and translates the CCRP-1 or CCRP-1/UCP polypeptides. Preferably, the transfected mammalian cell further comprises a cDNA sequence that confers antibiotic sensitivity to the mammalian cell as a "suicide gene" mechanism to remove the transformed mammalian cell from an individual if treated with said composition. Most preferably, the antibiotic is gancyclovir. The aspect of the transfected cells is that the transfected CCRP-1 gene enhance a cells ability to grow or be maintained under conditions where the fatty acids are present or at levels higher than normal. The present invention therefore includes not only cells with an enhanced ability to metabolize fatty acids and to grow or be maintained under conditions where fatty acid levels are higher than normal, but to methods of using the same.

The present invention further provides a physiologically acceptable composition for metabolizing fatty acids comprising a cDNA sequence encoding a CCRP-1 or CCRP-1/UCP polypeptide(s) in combination with appropriate regulatory and promoter sequences, wherein said cDNA sequence(s) is taken up into hosts cells, in vivo or in vitro, and is translated into CCRP-1 or CCRP-1/UCP polypeptide (s).

The present invention further provides a physiologically acceptable composition for metabolizing fatty acids comprising a culture of allogeneic brown fat cells, wherein the brown fat cells are maintained or proliferated ex vivo.

Further still, the present invention provides a method for maintaining a lower percentage of white adipose tissue than normal or effecting weight loss in a host, wherein the lean state or weight loss is due to prevention of accumulation, or loss, of white adipose tissue, with minimal loss of muscle mass, wherein the method for maintaining a lean state or effecting weight loss comprises administration of an effective amount of a physiologically acceptable composition described herein in sufficient amounts to metabolize at least 25 calories, preferably at least 55 calories or 25 g, per-day, preferably at least 65 g per day and in some embodiments more than 65 g per day of fatty acids. The compositions, methods, devices, etc. of the pervious sections may be practiced using the methods described in U.S. Pat. No. 5,453,270 (incorporated herein by reference in its entirety) and methods known in the art.

Methods for Screening Substances Interacting with a CCRP-1 Polypeptide

For the purpose of the present invention, a ligand means a molecule, such as a protein, a peptide, an antibody or any synthetic chemical compound capable of binding to the CCRP-1 protein or one of its fragments or variants or to modulate the expression of the polynucleotide coding for CCRP-1 or a fragment or variant thereof.

In the ligand screening method according to the present invention, a biological sample or a defined molecule to be tested as a putative ligand of the CCRP-1 protein is brought into contact with the corresponding purified CCRP-1 protein, for example the corresponding purified recombinant CCRP-1 protein produced by a recombinant cell host as described herein before, in order to form a complex between this protein and the putative ligand molecule to be tested.

As an illustrative example, to study the interaction of the CCRP-1 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO:2 with drugs or small molecules, such as molecules generated through combinatorial chemistry approaches, the microdialysis coupled to HPLC method described by Wang et al. (1997) or the affinity capillary electrophoresis method described by Bush et al. (1997), the disclosures of which are incorporated by reference, can be used.

In further methods, peptides, drugs, fatty acids, lipoproteins, or small molecules which interact with the CCRP-1 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO:2, may be identified using assays such as the following. The molecule to be tested for binding is labeled with a detectable label, such as a fluorescent, radioactive, or enzymatic tag and placed in contact with immobilized CCRP-1 protein, or a fragment thereof under conditions which permit specific binding to occur. After removal of non-specifically bound molecules, bound molecules are detected using appropriate means. Another object of the present invention comprises methods and kits for the screening of candidate substances that interact with CCRP-1 polypeptide.

The present invention pertains to methods for screening substances of interest that interact with a CCRP-1 protein or one fragment or variant thereof. By their capacity to bind covalently or non-covalently to a CCRP-1 protein or to a fragment or variant thereof, these substances or molecules may be advantageously used both in vitro and in vivo. In vitro, said interacting molecules may be used as detection means in order to identify the presence of a CCRP-1 protein in a sample, preferably a biological sample.

A method for the screening of a candidate substance comprises the following steps a) providing a polypeptide comprising, consisting essentially of, or consisting of a CCRP-1 polypeptide of the present invention comprising a contiguous span of at least 6 amino acids, preferably at least 8 to 10 amino acids, more preferably at least 12, 15, 20, 25, 30 30, 40, 50, or 100 amino acids of SEQ ID NO:2;

b) obtaining a candidate substance;

c) bringing into contact said polypeptide with said candidate substance;

d) detecting the complexes formed between said polypeptide and said candidate substance.

The invention further concerns a kit for the screening of a candidate substance interacting with the CCRP-1 polypeptide, wherein said kit comprises:

a) a CCRP-1 protein having an amino acid sequence selected from the group consisting of the amino acid sequences of SEQ ID NO:2 or a peptide fragment comprising a contiguous span of at least 6 amino acids, preferably at least 8 to 10 amino acids, more preferably at least 12, 15, 20, 25, 30, 40, 50, or 100 amino acids of SEQ ID NO:2, b) optionally means useful to detect the complex formed between the CCRP-1 polypeptide of the present invention and the candidate substance.

In a preferred embodiment of the kit described above, the detection means comprises a monoclonal or polyclonal antibodies directed against the CCRP-1 protein or a peptide fragment or a variant thereof.

Various candidate substances or molecules can be assayed for interaction with a CCRP-1 polypeptide. These substances or molecules include, without being limited to, natural or synthetic organic compounds or molecules of biological origin such as polypeptides. When the candidate substance or molecule comprises a polypeptide, this polypeptide may be the resulting expression product of a phage clone belonging to a phage-based random peptide library, or alternatively the polypeptide may be the resulting expression product of a cDNA library cloned in a vector suitable for performing a two-hybrid screening assay.

The invention also pertains to kits useful for performing the herein before described screening method. Preferably, such kits comprise a CCRP-1 polypeptide or a fragment or a variant thereof, and optionally means useful to detect the complex formed between the CCRP-1 polypeptide or its fragment or variant and the candidate substance. In a preferred embodiment the detection means comprise a monoclonal or polyclonal antibodies directed against the corresponding CCRP-1 polypeptide or a fragment or a variant thereof.

Candidate Lipands Obtained from Random Peptide Libraries

In a particular embodiment of the screening method, the putative ligand is the expression product of a DNA insert contained in a phage vector (Parmley and Smith, 1988). Specifically, random peptide phages libraries are used. The random DNA inserts encode for peptides of 8 to amino acids in length. See Oldenburg K. R. et al., (1992); Valadon P., et al., (1996); Lucas A. H., (1994); Westerink M. A. J., (1995); and Felici F. et al., (1991). According to this particular embodiment, the recombinant phages expressing a protein that binds to the immobilized CCRP-1 protein is retained and the complex formed between the CCRP-1 protein and the recombinant phage may be subsequently immunoprecipitated by a polyclonal or a monoclonal antibody directed against the CCRP-1 protein.

Once the ligand library in recombinant phages has been constructed, the phage population is brought into contact with the immobilized CCRP-1 protein. Then the preparation of complexes is washed in order to remove the non-specifically bound recombinant phages. The phages that bind specifically to the CCRP-1 protein are then eluted by a buffer (acid pH) or immunoprecipitated by the monoclonal antibody produced by the hybridoma anti-CCRP-1, and this phage population is subsequently amplified by an over-infection of bacteria (for example $E. coli$). The selection step may be repeated several times, preferably 2–4 times, in order to select the more specific recombinant phage clones. The last step comprises characterizing the peptide produced by the selected recombinant phage clones either by expression in infected bacteria and isolation, expressing the phage insert in another host-vector system, or sequencing the insert contained in the selected recombinant phages.

Candidate Ligands Obtained by Competition Experiments

Alternatively, peptides, drugs or small molecules which bind to the CCRP-1 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO:2 may be identified in competition experiments. In such assays, the CCRP-1 protein, or a fragment thereof, is immobilized to a surface, such as a plastic plate. Increasing amounts of the peptides, drugs or small molecules are placed in contact with the immobilized CCRP-1 protein, or a fragment thereof, in the presence of a detectable-labeled known CCRP-1 protein ligand. For example, the CCRP-1 ligand may be detectably labeled with a fluorescent, radioactive, or enzymatic tag. The ability of the test molecule to bind the CCRP-1 protein, or a fragment thereof, is determined by measuring the amount of detectably labeled known ligand bound in the presence of the test molecule. A decrease in the amount of known ligand bound to the CCRP-1 protein, or a fragment thereof, when the test molecule is present indicated that the test molecule is able to bind to the CCRP-1 protein, or a fragment thereof.

Candidate Ligands Obtained by Affinity Chromatography

Proteins or other molecules interacting with the CCRP-1 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO:2 can also be found using affinity columns which contain the CCRP-1 protein, or a fragment thereof. The CCRP-1 protein, or a fragment thereof, may be attached to the column using conventional techniques including chemical coupling to a suitable column matrix such as agarose, Affi Gelg®, or other matrices familiar to those of skill in art. In some embodiments of this method, the affinity column contains chimeric proteins in which the CCRP-1 protein, or a fragment thereof, is fused to glutathion S transferase (GST). A mixture of cellular proteins or pool of expressed proteins as described above is applied to the affinity column. Proteins or other molecules interacting with the CCRP-1 protein, or a fragment thereof, attached to the column can then be isolated and analyzed on 2-D electrophoresis gel as described in Ramunsen et al. (1997), the disclosure of which is incorporated by reference. Alternatively, the proteins retained on the affinity column can be purified by electrophoresis-based methods and sequenced. The same method can be used to isolate antibodies, to screen phage display products, or to screen phage display human antibodies.

Candidate Ligands Obtained by Optical Biosensor Methods

Proteins interacting with the CCRP-1 protein, or a fragment comprising a contiguous span of at least 6 amino acids, preferably at least 8 to 10 amino acids, more preferably at least 12, 15, 20, 25, 30, 40, 50, or 100 amino acids of SEQ ID NO:2, wherein said contiguous span includes diverging amino acids compared with known protein sequence or at least 1, 2, 3, 5 or 10 of the amino acid positions position range of new amino acid sequences, can also be screened by using an Optical Biosensor as described in Edwards and Leatherbarrow (1997) and also in Szabo et al. (1995), the disclosure of which is incorporated by reference. This technique permits the detection of interactions between molecules in real time, without the need of labeled molecules. This technique is based on the surface. plasmon resonance (SPR) phenomenon. Briefly, the candidate ligand molecule to be tested is attached to a surface (such as a carboxymethyl dextran matrix). A light beam is directed towards the side of the surface that does not contain the sample to be tested and is reflected by said surface. The SPR phenomenon causes a decrease in the intensity of the reflected light with a specific association of angle and wavelength. The binding of candidate ligand molecules cause a change in the refraction index on the surface, which change is detected as a change in the SPR signal. For screening of candidate ligand molecules or substances that are able to interact with the CCRP-1 protein, or a fragment thereof, the CCRP-1 protein, or a fragment thereof, is immobilized onto a surface. This surface comprises one side of a cell through which flows the candidate molecule to be assayed. The binding of the candidate molecule on the CCRP-1 protein, or a fragment thereof, is detected as a change of the SPR signal. The candidate molecules tested may be proteins, peptides, carbohydrates, lipids, or small molecules generated by combinatorial chemistry. This technique may also be performed by immobilizing eukaryotic or prokaryotic cells or lipid vesicles exhibiting an endogenous or a recombinantly expressed CCRP-1 protein at their surface.

The main advantage of the method is that it allows the determination of the association rate between the CCRP-1 protein and molecules interacting with the CCRP-1 protein. It is thus possible to select specifically ligand molecules interacting with the CCRP-1 protein, or a fragment thereof, through strong or conversely weak association constants.

Candidate Ligands Obtained through a Two-hybrid Screening Assay

The yeast two-hybrid system is designed to study protein-protein interactions in vivo. (Fields and Song, 1989), and relies upon the fusion of a bait protein to the DNA binding domain of the yeast Gal4 protein. This technique is also described in the U.S. Pat. No. 5,667,973 and the U.S. Pat. No. 5,283,173 (Fields et al.) the disclosures of both patents being incorporated herein by reference in their entireties. The general procedure of library screening by the two-hybrid assay may be performed as described by Harper et al. (1993) or as described by Cho et al. (1998) or also Fromont-Racine et al. (1997).

The bait protein or polypeptide comprises, consists essentially of, or consists of a CCRP-1 polypeptide or a fragment comprising a contiguous span of at least 6 amino acids, preferably at least 8 to 10 amino acids, more preferably at least 12, 15, 20, 25, 30, 40, 50, or 100 amino acids of SEQ ID NO:2.

More precisely, the nucleotide sequence encoding the CCRP-1 polypeptide or a fragment or variant thereof is fused to a polynucleotide encoding the DNA binding domain of the GAL4 protein, the fused nucleotide sequence being inserted in a suitable expression vector, for example pAS2 or pM3.

Then, a human cDNA library is constructed in a specially designed vector, such that the human cDNA insert is fused to a nucleotide sequence in the vector that encodes the transcriptional domain of the GAL4 protein. Preferably, the vector used is the pACT vector. The polypeptides encoded by the nucleotide inserts of the human cDNA library are termed "pray" polypeptides.

A third vector contains a detectable marker gene, such as beta galactosidase gene or CAT gene that is placed under the control of a regulation sequence that is responsive to the binding of a complete Gal4 protein containing both the transcriptional activation domain and the DNA binding domain. For example, the vector pG5EC may be used.

Two different yeast strains are also used. As an illustrative but non-limiting example the two different yeast strains may be the followings:

Y190, the phenotype of which is (MATa, Leu2-3, 112 ura3-12, trp1-901, his3-D200, ade2-101, gal4Dgal180D URA3 GAL-LacZ, LYS GAL-HIS3, cyh$^r$);

Y187, the phenotype of which is (MATa gal4 gal80 his3 trp1-901 ade2-101 ura3-52 leu2-3, -112 URA3 GAL-lacZmet$^-$), which is the opposite mating type of Y190.

Briefly, 20 μg of pAS2/CCRP-1 and 20 μg of pACT-cDNA library are co-transformed into yeast strain Y190. The transformants are selected for growth on minimal media lacking histidine, leucine and tryptophan, but containing the histidine synthesis inhibitor 3-AT (50 mM). Positive colonies are screened for beta galactosidase by filter lift assay. The double positive colonies (His$^+$, beta-gal$^+$) are then grown on plates lacking histidine, leucine, but containing tryptophan and cycloheximide (10 mg/ml) to select for loss of pAS2/CCRP-1 plasmids but retention of pACT-cDNA library plasmids. The resulting Y190 strains are mated with Y187 strains expressing CCRP-1 or non-related control proteins; such as cyclophilin B, lamin, or SNF1, as Gal4 fusions as described by Harper et al. (1993) and by Bram et al. (1993), and screened for beta galactosidase by filter lift assay. Yeast clones that are beta gal- after mating with the control Gal4 fusions are considered false positives.

In another embodiment of the two-hybrid method according to the invention, interaction between the CCRP-1 or a fragment or variant thereof with cellular proteins may be assessed using the Matchmaker Two Hybrid System 2 (Catalog No. K1604-1, Clontech). As described in the manual accompanying the Matchmaker Two Hybrid System 2 (Catalog No. K1604-1, Clontech), the disclosure of which is incorporated herein by reference, nucleic acids encoding the CCRP-1 protein or a portion thereof, are inserted into an expression vector such that they are in frame with DNA encoding the DNA binding domain of the yeast transcriptional activator GAL4. A desired cDNA, preferably human cDNA, is inserted into a second expression vector such that they are in frame with DNA encoding the activation domain of GAL4. The two expression plasmids are transformed into yeast and the yeast are plated on selection medium which selects for expression of selectable markers on each of the expression vectors as well as GAL4 dependent expression of the HIS3 gene. Transformnants capable of growing on medium lacking histidine are screened for GAL4 dependent lacZ expression. Those cells which are positive in both the histidine selection and the lacZ assay contain interaction between CCRP-1 and the protein or peptide encoded by the initially selected cDNA insert.

Method for Screening Substances Interacting with the Regulatory Sequences of the CCRP-1 Gene The present invention also concerns a method for screening substances or molecules that are able to interact with the regulatory sequences of the CCRP-1 gene, such as for example promoter or enhancer sequences.

Nucleic acids encoding proteins which are able to interact with the regulatory sequences of the CCRP-1 gene, more particularly a nucleotide sequence selected from the group consisting of the polynucleotides of the 5' and 3' regulatory region or a fragment or variant thereof, and preferably a variant comprising one of the biallelic markers of the invention, may be identified by using a one-hybrid system, such as that described in the booklet enclosed in the Matchmaker One-Hybrid System kit from Clontech (Catalog Ref. n° K1603-1), the technical teachings of which are herein incorporated by reference. Briefly, the target nucleotide sequence is cloned upstream of a selectable reporter sequence and the resulting DNA construct is integrated in the yeast genome (*Saccharomyces cerevisiae*). The yeast cells containing the reporter sequence in their genome are then transformed with a library comprising fusion molecules between cDNAs encoding candidate proteins for binding onto the regulatory sequences of the CCRP-1 gene and sequences encoding the activator domain of a yeast transcription factor such as GAL4. The recombinant yeast cells are plated in a culture broth for selecting cells expressing the reporter sequence. The recombinant yeast cells thus selected contain a fusion protein that is able to bind onto the target regulatory sequence of the CCRP-1 gene. Then, the cDNAs encoding the fusion proteins are sequenced and may be cloned into expression or transcription vectors in vitro. The binding of the encoded polypeptides to the target regulatory sequences of the CCRP-1 gene may be confirmed by techniques familiar to the one skilled in the art, such as gel retardation assays or DNAse protection assays.

Gel retardation assays may also be performed independently in order to screen candidate molecules that are able to interact with the regulatory sequences of the CCRP-1 gene, such as described by Fried and Crothers (1981), Garner and Revzin (1981) and Dent and Latchman (1993), the teachings of these publications being herein incorporated by reference. These techniques are based on the principle according to which a DNA fragment which is bound to a protein migrates slower than the same unbound DNA fragment. Briefly, the target nucleotide sequence is labeled. Then the labeled target nucleotide sequence is brought into contact with either a total nuclear extract from cells containing transcription factors, or with different candidate molecules to be tested. The interaction between the target regulatory sequence of the CCRP-1 gene and the candidate molecule or the transcription factor is detected after gel or capillary electrophoresis through a retardation in the migration.

Method for Screening Lipands that Modulate the Expression of the CCRP-1 Gene

Another subject of the present invention is a method for screening molecules that modulate the expression of the CCRP-1 protein. Such a screening method comprises the steps of:

a) cultivating a prokaryotic or a eukaryotic cell that has been transfected with a nucleotide sequence encoding the CCRP-1 protein or a variant or a fragment thereof, placed under the control of its own promoter;

b) bringing into contact the cultivated cell with a molecule to be tested;

c) quantifying the expression of the CCRP-1 protein or a variant or a fragment thereof.

Using DNA recombination techniques well known by the one skill in the art, the CCRP-1 protein encoding DNA sequence is inserted into an expression vector, downstream from its promoter sequence. As an illustrative example, the promoter sequence of the CCRP-1 gene is contained in the nucleic acid of the 5' regulatory region.

The quantification of the expression of the CCRP-1 protein may be realized either at the mRNA level or at the protein level. In the latter case, polyclonal or monoclonal antibodies may be used to quantify the amounts of the CCRP-1 protein that have been produced, for example in an ELISA or a RIA assay.

In a preferred embodiment, the quantification of the CCRP-1 mRNA is realized by a quantitative PCR amplification of the cDNA obtained by a reverse transcription of the total mRNA of the cultivated CCRP-1-transfected host cell, using a pair of primers specific for CCRP-1.

The present invention also concerns a method for screening substances or molecules that are able to increase, or in contrast to decrease, the level of expression of the CCRP-1 gene. Such a method may allow the one skilled in the art to select substances exerting a regulating effect on the expression level of the CCRP-1 gene and which may be useful as active ingredients included in pharmaceutical compositions for treating patients suffering from metabolic diseases.

Thus, also part of the present invention is a method for screening of a candidate substance or molecule that modulated the expression of the CCRP-1 gene, this method comprises the following steps:

providing a recombinant cell host containing a nucleic acid, wherein said nucleic acid comprises a nucleotide sequence of the 5' regulatory region or a biologically active fragment or variant thereof located upstream a polynucleotide encoding a detectable protein;

obtaining a candidate substance; and determining the ability of the candidate substance to modulate the expression levels of the polynucleotide encoding the detectable protein.

In a further embodiment, the nucleic acid comprising the nucleotide sequence of the 5' regulatory region or a biologically active fragment or variant thereof also includes a 5' UTR region of the CCRP-1 cDNA of SEQ ID NO:1, or one of its biologically active fragments or variants thereof.

Among the preferred polynucleotides encoding a detectable protein, there may be cited polynucleotides encoding beta galactosidase, green fluorescent protein (GFP) and chloramphenicol acetyl transferase (CAT).

The invention also pertains to kits useful for performing the herein described screening method. Preferably, such kits comprise a recombinant vector that allows the expression of a nucleotide sequence of the 5' regulatory region or a biologically active fragment or variant thereof located upstream and operably linked to a polynucleotide encoding a detectable protein or the CCRP-1 protein or a fragment or a variant thereof.

In another embodiment of a method for the screening of a candidate substance or molecule that modulates the expression of the CCRP-1 gene, wherein said method comprises the following steps:

a) providing a recombinant host cell containing a nucleic acid, wherein said nucleic acid comprises a 5'UTR sequence of the CCRP-1 cDNA of SEQ ID NO:1, or one of its biologically active fragments or variants, the 5'UTR sequence or its biologically active fragment or variant being operably linked to a polynucleotide encoding a detectable protein;

b) obtaining a candidate substance; and c) determining the ability of the candidate substance to modulate the expression levels of the polynucleotide encoding the detectable protein.

In a specific embodiment of the above screening method, the nucleic acid that comprises a nucleotide sequence selected from the group consisting of the 5'UTR sequence of the CCRP-1 cDNA of SEQ ID NO:1 or one of its biologically active fragments or variants, includes a promoter sequence which is endogenous with respect to the CCRP-1 5'UTR sequence.

In another specific embodiment of the above screening method, the nucleic acid that comprises a nucleotide sequence selected from the group consisting of the 5'UTR sequence of the CCRP-1 cDNA of SEQ ID NO:1 or one of its biologically active fragments or variants, includes a promoter sequence which is exogenous with respect to the CCRP-1 5'UTR sequence defined therein.

The invention further comprises with a kit for the screening of a candidate substance modulating the expression of the CCRP-1 gene, wherein said kit comprises a recombinant vector that comprises a nucleic acid including a 5'UTR sequence of the CCRP-1 cDNA of SEQ ID NO:1, or one of their biologically active fragments or variants, the 5'UTR sequence or its biologically active fragment or variant being operably linked to a polynucleotide encoding a detectable protein.

For the design of suitable recombinant vectors useful for performing the screening methods described above, it will be referred to the section of the present specification wherein the preferred recombinant vectors of the invention are detailed.

Expression levels and patterns of CCRP-1 may be analyzed by solution hybridization with long probes as described in International Patent Application No. WO 97/05277, the entire contents of which are incorporated herein by reference. Briefly, the CCRP-1 cDNA or the CCRP-1 genomic DNA described above, or a fragment thereof, is inserted at a cloning site immediately downstream of a bacteriophage (T3, T7 or SP6) RNA polymerase promoter to produce antisense RNA.

Preferably, the CCRP-1 insert comprises at least 100 or more consecutive nucleotides of the genomic DNA sequence or the cDNA sequences. The plasmid is linearized and transcribed in the presence of ribonucleotides comprising modified ribonucleotides (i.e. biotin-UTP and DIG-UTP). An excess of this doubly labeled RNA is hybridized in solution with mRNA isolated from cells or tissues of interest. The hybridization is performed under standard stringent conditions (40–50° C. for 16 hours in an 80% formamide, 0.4 M NaCl buffer, pH 7–8). The unhybridized probe is removed by digestion with ribonucleases specific for single-stranded RNA (i.e. RNases CL3, T1, Phy M, U2 or A). The presence of the biotin-UTP modification enables capture of the hybrid on a microtitration plate coated with streptavidin. The presence of the DIG modification enables the hybrid to be detected and quantified by ELISA using an anti-DIG antibody coupled to alkaline phosphatase.

Quantitative analysis of CCRP-1 gene expression may also be performed using arrays. As used herein, the term array means a one dimensional, two dimensional, or multi-dimensional arrangement of a plurality of nucleic acids of sufficient length to permit specific detection of expression of mRNAs capable of hybridizing thereto. For example, the arrays may contain a plurality of nucleic acids derived from genes whose expression levels are to be assessed. The arrays may include the CCRP-1 genomic DNA, the CCRP-1 cDNA sequences or the sequences complementary thereto or fragments thereof. Preferably, the fragments are at least 15 nucleotides in length. In other embodiments, the fragments are at least 25 nucleotides in length. In some embodiments, the fragments are at least 50 nucleotides in length. More preferably, the fragments are at least 100 nucleotides in length. In another preferred embodiment, the fragments are more than 100 nucleotides in length. In some embodiments the fragments may be more than 500 nucleotides in length.

For example, quantitative analysis of CCRP-1 gene expression may be performed with a complementary DNA microarray as described by Schena et al. (1995,1996). Full-length CCRP-1 cDNAs or fragments thereof are amplified by PCR and arrayed from a 96-well microtiter plate onto silylated microscope slides using high-speed robotics. Printed arrays are incubated in a humid chamber to allow rehydration of the array elements and rinsed, once in 0. 2% SDS for 1 min, twice in water for 1 min and once for 5 min in sodium borohydride solution. The arrays are submerged in water for 2 min at 95° C., transferred into 0. 2% SDS for 1 min, rinsed twice with water, air-dried and stored in the dark at 25° C.

Cell or tissue mRNA is isolated or commercially obtained and probes are prepared by a single round of reverse transcription. Probes are hybridized to 1 $cm^2$ microarrays under a 14×14 mm glass coverslip for 6–12 hours at 60° C. Arrays are washed for 5 min at 25° C. low stringency wash buffer (1×SSC/0. 2% SDS), then for 10 min at room temperature in high stringency wash buffer (0. 1×SSC/0. 2% SDS). Arrays are scanned in 0. 1×SSC using a fluorescence laser-scanning device fitted with a custom filter set. Accurate differential expression measurements are obtained by taking the average of the ratios of two independent hybridizations.

Quantitative analysis of CCRP-1 gene expression may also be performed with full length CCRP-1 cDNAs or fragments thereof in complementary DNA arrays as described by Pietu et al.(1996). The full-length CCRP-1 cDNA or fragments thereof is PCR amplified and spotted on membranes. Then, mRNAs originating from various tissues or cells are labeled with radioactive nucleotides. After hybridization and washing in controlled conditions, the hybridized mRNAs are detected by phospho-imaging or autoradiography. Duplicate experiments are performed and a quantitative analysis of differentially expressed mRNAs is then performed.

Alternatively, expression analysis using the CCRP-1 genomic DNA, the CCRP-1 cDNA, or fragments thereof can be done through high-density nucleotide arrays as described by Lockhart et al. (1996) and Sosnowsky et al. (1997). Oligonucleotides of 15–50 nucleotides from the sequences of the CCRP-1 genomic DNA, the CCRP-1 cDNA sequences particularly those comprising at least one of biallelic markers according the present invention, preferably at least one biallelic marker selected from the group consisting of A1 to A17, or the sequences complementary thereto, are synthesized directly on the chip (Lockhart et al., supra) or synthesized and then addressed to the chip (Sosnowski et al., supra). Preferably, the oligonucleotides are about 20 nucleotides in length.

CCRP-1 cDNA probes labeled with an appropriate compound, such as biotin, digoxigenin or fluorescent dye, are synthesized from the appropriate mRNA population and then randomly fragmented to an average size of 50 to 100 nucleotides. The said probes are then hybridized to the chip. After washing as described in Lockhart et al., supra and application of different electric fields. (Sosnowsky et al., 1997), the dyes or labeling compounds are detected and quantified. Duplicate hybridizations are performed. Comparative analysis of the intensity of the signal originating from cDNA probes on the same target oligonucleotide in different cDNA samples indicates a differential expression of CCRP-1 mRNA.

Methods for Inhibiting the Expression of a CCRP-1 Gene

Other therapeutic compositions according to the present invention comprise advantageously an oligonucleotide fragment of the nucleic.sequence of CCRP-1 as an antisense tool or a triple helix tool that inhibits the expression of the corresponding CCRP-1 gene.

Antisense Approach

Preferred methods using antisense polynucleotide according to the present invention are the procedures described by Sczakiel et al. (1995).

Preferably, the antisense tools are chosen among the polynucleotides (15–200 bp long) that are complementary to the 5' end of the CCRP-1 mRNA. In another embodiment, a combination of different antisense polynucleotides complementary to different parts of the desired targeted gene are used.

Preferred antisense polynucleotides according to the present invention are complementary to a sequence of the mRNAs of CCRP-1 that contains either the translation initiation codon ATG or a splicing donor or acceptor site.

The antisense nucleic acids should have a length and melting temperature sufficient to permit formation of an intracellular duplex having sufficient stability to inhibit the expression of the CCRP-1 mRNA in the duplex. Strategies for designing antisense nucleic acids suitable for use in gene therapy are disclosed in Green et al. (1986), and Izant and Weintraub (1984), the disclosures of which are incorporated herein by reference.

In some strategies, antisense molecules are obtained by reversing the orientation of the CCRP-1 coding region with respect to a promoter so as to transcribe the opposite strand from that which is normally transcribed in the cell. The antisense molecules may be transcribed using in vitro transcription systems such as those which employ T7 or SP6 polymerase to generate the transcript. Another approach involves transcription of CCRP-1 antisense nucleic acids in vivo by operably linking DNA containing the antisense sequence to a promoter in a suitable expression vector.

Alternatively, suitable antisense strategies are those described by Rossi et al. (1991), in the International Applications Nos. WO 94/23026, WO 95/04141, WO 92/18522 and in the European Patent Application No. EP 0 572 287 A2, the disclosures of which are incorporated herein by reference in their entireties.

An alternative to the antisense technology that is used according to the present invention comprises using ribozymes that will bind to a target sequence via their complementary polynucleotide tail and that will cleave the corresponding RNA by hydrolyzing its target site (namely "hammerhead ribozymes"). Briefly, the simplified cycle of a hammerhead ribozyme comprises (1) sequence specific binding to the target RNA via complementary antisense sequences; (2) site-specific hydrolysis of the cleavable motif of the target strand; and (3) release of cleavage products, which gives rise to another catalytic cycle. Indeed, the use of long-chain antisense polynucleotide (at least 30 bases long) or ribozymes with long antisense arms are advantageous. A preferred delivery system for antisense ribozyme is achieved by covalently linking these antisense ribozymes to lipophilic groups or to use liposomes as a convenient vector. Preferred antisense ribozymes according to the present invention are prepared as described by Sczakiel et al. (1995), the specific preparation procedures being referred to in said article being herein incorporated by reference.

Triple Helix Approach

The CCRP-1 genomic DNA may also be used to inhibit the expression of the CCRP-1 gene based on intracellular triple helix formation.

Triple helix oligonucleotides are used to inhibit transcription from a genome. They are particularly useful for studying alterations in cell activity when it is associated with a particular gene.

Similarly, a portion of the CCRP-1 genomic DNA can be used to study the effect of inhibiting CCRP-1 transcription within a cell. Traditionally, homopurine sequences were considered the most useful for triple helix strategies. However, homopyrimidine sequences can also inhibit gene expression. Such homopyrimidine oligonucleotides bind to the major groove at homopurine:homopyrimidine sequences. Thus, both types of sequences from the CCRP-1 genomic DNA are contemplated within the scope of this invention.

To carry out gene therapy strategies using the triple helix approach, the sequences of the CCRP-1 genomic DNA are first scanned to identify 10-mer to 20-mer homopyrimidine or homopurine stretches which could be used in triple-helix based strategies for inhibiting CCRP-1 expression. Following identification of candidate homopyrimidine or homopurine stretches, their efficiency in inhibiting CCRP-1 expression is assessed by introducing varying amounts of oligonucleotides containing the candidate sequences into tissue culture cells which express the CCRP-1 gene.

The oligonucleotides can be introduced into the cells using a variety of methods known to those skilled in the art, including but not limited to calcium phosphate precipitation, DEAE-Dextran, electroporation, liposome-mediated transfection or native uptake.

Treated cells are monitored for altered cell function or reduced CCRP-1 expression using techniques such as Northern blotting, RNase protection assays, or PCR based strategies to monitor the transcription levels of the CCRP-1 gene in cells which have been treated with the oligonucleotide.

The oligonucleotides which are effective in inhibiting gene expression in tissue culture cells may then be introduced in vivo using the techniques described above in the antisense approach at a dosage calculated based on the in vitro results, as described in antisense approach.

In some embodiments, the natural (beta) anomers of the oligonucleotide units can be replaced with alpha anomers to render the oligonucleotide more resistant to nucleases. Further, an intercalating agent such as ethidium bromide, or the like, can be attached to the 3' end of the alpha oligonucleotide to stabilize the triple helix. For information on the generation of oligonucleotides suitable for triple helix formation. See Griffin et al. (1989), which is hereby incorporated by this reference.

REFERENCES

Abbondanzo S J et al. (1993), *Methods in Enzymology*, Academic Press, New York, pp 803–823.
Ajioka R. S. et al. (1997),*Am. J. Hum. Gene.* 60:1439–1447.
Altschul et al. (1990), *J. Mol. Biol.* 215(3):403–410.
Altschul et al. (1993), *Nature Genetics.* 3:266–272.
Altschul et al. (1997), *Nuc. Acids Res.* 25:3389–3402.
Ames, R. S., et al. (1995), *J. Immunol. Methods* 184:177–186.
Anton M. et al. (1995), *J. Virol.* 69 4600–4606.
Araki K et al. (1995), *Proc. Natl. Acad. Sci. U S A.* 92(1):160–4.
Ashkenazi, A et al. (1991), *PNAS* 88:10535–10539.
Aszódi et al. (1997), *Proteins: Structure, Function, and Genetics, Supplement.* 1:38–42.
Ausubel et al. (1989), *Current Protocols in Molecular Biology.* Green Publishing Associates and Wiley Interscience, N.Y.
Bartunek, et al. (1996), *Cytokine.* 8(1):14–20.
Baubonis W. (1993), *Nucleic Acids Res.* 21(9):2025–9.
Beaucage et al. (1981), *Tetrahedron Lett.* 22: 1859–1862.
Better, M. et al. (1988), *Science.* 240:1041–1043.
Bittle, F. J. et al. (1985), *Virol.* 66:2347–2354.
Boomer, U. et al. (1996), *J. Mol, Biol.* 262:389–395.
Boss, Om, et al. (1997), *FEBS Lett.* 408:39–42.
Bowie, J. U) et al. (1994), *Science.* 247:1306–1310.
Bradley A., (1987), *Production and analysis of chimaeric mice. In:* E. J. Robertson (Ed.), *Teratocarcinomas and embryonic stem cells: A practical approach.* IRL Press, Oxford, pp.113.
Bram R J et al. (1993), *Mol. Cell Biol.* 13: 4760–4769.
Brinkman U. et al. (1995) *J. Immunol Methods.* 182:41–50.
Brown E L, Belagaje R, Ryan M J, Khorana H G (1979), *Methods Enzymol.* 68:109–151.
Brutlag et al., (1990), *Comp. App. Biosci.* 6:237–245.
Burton, D. R. et al. (1994), *Advances in Immunology.* 57:191–280
Bush et al. (1997), *J. Chromatogr.* 777:311–328.
Carlson, N. G. et al. (1997), *J. Biol. Chem.* 272(17):11295–11301.
Chai H. et al. (1993), *Biotechnol. Appl. Biochem.*18:259–273.
Chee et al. (1996) *Science.* 274: 610–614.
Chen and Kwok (1997), *Nucleic Acids Research.* 25:347–353.
Chen et al. (1987), *Mol. Cell. Biol.* 7:2745–2752.
Chen et al. (1997), *Proc. Natl. Acad Sci. USA.* 94(20):10756–10761.
Chen, Z. et al. (1998), *Cancer Res.* 58(16):3668–3678.
Chien et al. (1991), *Proc. Natl. Acad. Sci. USA.* 88:94–578.
Cho R J et al. (1998), *Proc. Natl. Acad. Sci. USA.* 95(7): 3752–3757.
Chou J. Y. (1989), *Mol. Endocrinol.* 3: 1511–1514.
Chow, M., et al. (1985), *Proc. Nat. Acad Sci. USA.* 82:910–914.
Clark A. G. (1990), *Mol. Biol. Evol.* 7: 111–122.
Cleland et al. (1993), *Crit. Rev. Therapeutic Drug Carrier Systems.* 10:307–377.
Coles R, Caswell R, Rubinsztein D C (1998), *Hum Mol Genet.* 7:791–800.
Compton J. (1991), *Nature.* 350(6313): 91–92.
Creighton W. H. Freeman and Company, New York (1993), *Posttranslational Covalent Modification of Proteinins,* B. C. Johnson, Ed., Academic Press, New York 1-Creighton (1983), *Proteins: Structures and Molecular Principles,* W. H. Freeman & Co. N.Y.
Cummingham et al. (1989), *Science* 244:1081–1085.
Davis L. G., M. D. Dibner, and J. F. Battey (1986), *Basic Methods in Molecular Biology,* ed., Elsevier Press, NY.
Dempster et al. (1977), *J. R. Stat. So.* 39B:1–38.
Deng, B. et al. (1998) *Blood.* 92(6):1981–1988.
Dent D S & Latchman D S (1993), *The DNA Mobility Shift Assay. In. Transcription Factors: A Practical Approach* (Latchman DS, ed.) pp1–26. Oxford: IRL Press. Eckner R. et al. (1991), *EMBO J.* 10:3513–3522.
Edwards et al. (1997), *Analytical Biochemistry,* Leatherbarrow. 246, 1–6.
Engvall, E., (1980), *Meth. Enzymol.* 70:419.
Excoffier L. and Slatkin M. (1995), *Mol. Biol. Evol.* 12(5): 921–927.
Feldman and Steg (1996), Medecine/Sciences, synthese 12:47–55

Felici F. (1991), *J. Mol. Biol.* 222:301–310.
Fell, H. P. et al. (1991), *J. Immunol.* 146:2446–2452.
Fields and Song, (1989), *Nature,* 340: 245–246.
Fisher, D. (1980), Chap. 42 in: *Manual of Clinical Immunology,* 2d Ed. (Rose and Friedman, Eds.) Amer. Soc. For Microbiol, Washington, D.C.
Fleury, C., et al. (1997), *Nature Genetics.* 15:269–272.
Flotte et al. (1992),*Am. J. Respir. Cell Mol. Biol.* 7:349–356.
Fodor et al. (1991), *Science.* 251:767–777.
Fountoulakis et al. (1995), *Biochem.* 270:3958–3964.
Fraley et al. (1979), *Proc. Natl. Acad. Sci. USA.* 76:3348–3352.
Fried M, Crothers D M (1981), *Nucleic Acids Res.* 9:6505–6525
Fromont-Racine M. et al. (1997), *Nature Genetics,* 16(3): 277–282.
Fuller S. A. et al. (1996) *Immunology in Current Protocols in Molecular Biology,* Ausubel et al., Eds, John Wiley & Sons, Inc., USA.
Furth P. A. et al. (1994), *Proc. Natl. Acad. Sci USA.* 91:9302–9306.
Garner M M, Revzin A. (1981), *Nucleic Acids Res.* 9:3047–3060.
Geysen M. H. et al., (1984), *Proc. Natl. Acad. Sci. U.S.A.* 81:3998–4002.
Ghosh and Bacchawat (1991), *Targeting of liposomes to hepatocytes,* IN: *Liver Diseases, Targeted diagnosis and therapy using specific rceptors and ligand* Wu et al., Eds, Marcel Dekeker, New York, pp. 87–104.
Gillies, S. D. et al. (1989), *J. Immunol Methods.* 125:191–202.
Gillies, S. O., et al. (1992), *PNAS.* 89:1428–1432.
Gonnet et al. (1992), *Science.* 256:1443–1445.
Gopal (1985), *Mol. Cell. Biol.* 5:1188–1190.
Gossen M. et al. (1992), *Proc. Natl Acad. Sc.i USA.* 89:5547–5551.
Gossen M. et al. (1995), *Science.* 268:1766–1769.
Graham et al. (1973), *Virology.* 52:456–457.
Green et al. (1986), *Ann. Rev. Biochem.* 55:569–597.
Greenspan and Bona (1989), *FASEB J.* 7(5):437–444.
Griffin et al. (1989), *Science.* 245:967–971.
Grompe, M. (1993), *Nature Genetics.* 5:111–117.
Grompe, M. et al. (1989), *Proc. Natl. Acad. Sci. U.S.A.* 86:5855–5892.
Gu H. et al. (1993) *Cell* 73:1155–1164.
Gu H. et al. (1994), *Science* 265:103–106.
Guatelli J C et al. *Proc. Natl. Acad. Sci. USA.* 35:273–286.
Hansson, L. O. et al. (1999), *J. Mol. Boil.* 287:265–276.
Haravama S. (1998), *Trends Biotechnol.* 16(2): 76–82.
Harrop, J. A. et al., (1998), *J. Immunol.* 161(4):1786–1794.
Hacia J G, Brody L C, Chee M S, Fodor S P, Collins F S (1996); *Nat Genet.* 14(4):441–447.
Hall L. A. and Smirnov I. P. (1997), *Genome Research.* 7:378–388.
Hames B. D. and Higgins S. J. (1985), *Nucleic Acid Hybridization: A Practical Approach.* Hames and Higgins Ed., IRL Press, Oxford.
Hammerling (1981), *Monoclonal Antibodies and T-Cell Hybridomas,* Elsevier, N.Y. 563–681.
Harju L, Weber T, Alexandrova L, Lukin M, Ranki M, Jalanko A, (1993), *Clin Chem;*39(11Pt 1):2282–2287.
Harland et al. (1985), *J. Cell. Biol.* 101:1094–1095.
Harlow, E., and D. Lane. (1988). *Antibodies:A Laboratory Manual.* Cold Spring Harbor Laboratory. pp. 53–242.
Harper J W et al. (1993), *Cell,* 75: 805–816.
Hawley M. E. et al. (1994), *Am. J. Phys. Anthropol.* 18:104.
Henikoff and Henikoff, (1993), *Proteins.* 17:49–61.

Higgins et al. (1996), *Methods Enzymol.* 266:383–402.
Hillier L. and Green P (1991), *Methods Appl,* 1: 124–8.
Himm-Hagen, J. (1989), *J. Prog. Lipid Res.* 28:67–115.
Hoess et al., (1986), *Nucleic Acids Res.* 14:2287–2300.
Hoppe et al. (1994), *FEBS Letters.* 344:191.
Houghten, R. A. (1985), *Proc. Natl. Acad. Sci. USA* 82:5131–5135.
Huang L. et al. (1996), *Cancer Res* 56(5):1137–1141.
Huston et al. (1991), *Methods in Enymology* 203:46–88.
Humkpiller et al. (1984), *Nature.* 310:105–111.
Huygen et al. (1996), *Nature Medicine.* 2(8):893–898.
Izant J G, Weintraub H, *Cell* (1984), Apr; 36(4):1007–15.
Jameson and Wolf, (1988), *Comp. Appl. Biosci.* 4:181–186.
Julan et al., (1992), *J. Gen. Virol.* 73:3251–3255.
Kanegae Y. et al. (1995), *Nucl. Acids Res.* 23:3816–3821.
Karlin and Altschul, (1990), *Proc. Natl. Acad. Sci. USA* 87:2267–2268.
Kettleborough, C. A. et al. (1994), *Eur. L Immunol.* 24:952–958.
Khoury J. et al., (1993), *Fundamentals of Genetic Epidemiology,* Oxford University Press, N.Y.
Kim U-J. et al. (1996), *Genomics.* 34:213–218.
Klein et al., (1987), *Nature.* 327:70–73.
Kohler, G. and Milstein, C. (1975), *Nature* 256:495.
Koller et al. (1989), *Proc. Natl. Acad. Sci. USA* 86:8932–8935.
Koller et al. (1992) *Annu. Rev. Immunol.* 10:705–730.
Kopecky J., et al. (1995), *J. Clin. Invest.* 96:2914–23.
Kostelny, S. A. et al. (1992), *J. Immunol.* 148:1547–1553.
Kozal M. J, et al. (1996) *Nat Med.* 2(7):753–759.
Lander and Schork, (1994), *Science,* 265, 2037–2048.
Landegren U. et al. (1998), *Genome Research,* 8:769–776.
Lange K. (1997), *Mathematical and Statistical Methodsfor Genetic Analysis.* Springer, New York.
Landschulz et al. (1988), *Science.* 240:1759.
Larkins S. et al, (1997)*Biochem Bioph vs. Rse Comm.* 240:222p227.
Leibel et al. (1995), *New Behland Journal Of Medicine.* 322:621–28.
Lenhard T. et al. (1996), *Gene.* 169:187–190.
Lewin, B., (1989), *Proc. Natl. Acad. Sco. USA* 86:9832–8935.
Liautard, J. et al. (1997), *Cytokinde.* 9(4):233–241.
Linton M. F. et al. (1993), *J. Clin. Invest.* 92:3029–3037.
Liu Z. et al.(1994), *Proc. Natl. Acad. Sci. USA.* 91:4528–4262.
Livak et al., (1995), *Nature Genetics.* 9:341–342.
Livak K J, Hainer J W, (1994), *Hum Mutat.* 3(4):379–385.
Lockhart et al., (1996), *Nature Biotechnology.* 14: 1675–1680.
Lorenzo, M. M. and Blasco, R. (1998), *Biotechniques.* 24(2):308–313.
Loring et al. (1996), *Neurobiol. Aging.* 17:173.
Lowell, B. B. et al. (1993), 366:740.
Lucas A. H., (1994), *In Development and Clinical Uses of Haempophilus b Conjugate.*
Maarse, A. et al. (1994), *FEBS Lett.* 349:215–221.
Malik et al. (1992), *Exp. Hematol.* 20:1028–1035.
Mansour S. L. et al. (1988), *Nature.* 336:348–352.
Marshall R. L. et al. (1994), *PCR Methods and Applications.* 4:80–84.
McCormick et al. (1994), *Genet. Anal. Tech. Appl.* 11:158–164.
McLaughlin B. A. et al. (1996), *Am. J. Hum. Genet.* 59:561–569.
Morton N. E., (1955), *Am. J. Hum. Genet.* 7:277–318.
Muller, Y. A. et al. (1998), *Structure.* 6(9):1153–1167.

Mullinax, R. L. et al. (1992), *BioTechniques*. 12(6):864–869.
Muzyczka et al. (1992), *Curr. Topics in Micro. and Immunol.* 158:97–129.
Nada S. et al. (1993), *Cell* 73:1125–1135.
Nagy A. et al., (1993), *Proc. Natl. Acad. Sci. USA*, 90: 8424–8428.
Naramura, M. et al. (1994), *Immunol. Lett.* 39:91–99.
Narang S A, Hsiung H M, Brousseau R (1979), *Methods Enzymol;* 68:90–98.
Neda et al., (1991), *J. Biol. Chem.* 266:14143–14146.
Newton et al., (1989), *Nucleic Acids Res.* 17:2503–2516.
Nickerson D. A. et al. (1990) *Proc. Natl. Acad. Sci. U.S.A.* 87:8923–8927.
Nicolau C. et al. (1987), *Methods Enzymol.* 149:157–76.
Nicolau et al. (1982), *Biochim. Biophys. Acta.* 721:185–190.
Nicolls, D. G., and Locke, R. M., (1994), *Physiol Rev.* 64:2–40.
Nissinoff, (1991), *J. Immunol.* 147(8): 2429–2438.
Nyren P, Pettersson B, Uhlen M (1993), *Anal Biochem.* 208(1):171–175.
O'Reilly et al. (1992), *Baculovirus Expression Vectors: A Laboratory Manual.* W. H. Freeman and Co., New York.
Ohno et al., (1994), *Science.* 265:781–784.
Oi et al. (1986), *BioTechniques* 4:214.
Oldenburg K. R. et al. (1992), *Proc. Natl. Acad. Sci.,* 89:5393–5397.
Orita et al., (1989), *Proc. Natl. Acad. Sci. U.S.A.* 86: 2776–2770.
Ott J., (1991), *Analysis of Human Genetic Linkage, John Hopkins University Press, Baltimore.*
Ouchterlony, O. et al. (1973), Chap. 19 in: *Handbook of Experimental Immunology D. Wie (red) Blackwell.*
Padlan E. A. (1991), *Moloecular Immunology* 28(4/5):489–498.
Parmley and Smith (1988), *Gene.* 73:305–318.
Pastinen et al. (1997), *Genome Research.* 7:606–614.
Patten, P. A., et al. (1997), *Curr Opinion Biotechnol.* 8:724–733.
Pearson and Lipman, (1988), *Proc. Natl. Acad. Sci. USA* 85(8):2444–2448.
Pease S. and William R. S. (1990), *Exp. Cell. Res.,* 190: 209–211.
Perlin et al. (1994), *Am. J. Hum. Genet.* 55:777–787.
Persic, L. et al. (1997), *Gene.* 1879–81
Peterson et al. (1993), *Proc. Natl. Acad. Sci. USA,* 90:7593–7597.
Pfanner, N et al.(1996), *Trends Biochem. Sco.* 21:51–52.
Pietu et al. (1996), *Genome Research.* 6:492–503.
Pitard, V. et al. (1997), *J. Immunol. Methods.* 205(2):177–190.
Pinckard et al. (1967), *Clin. Exp. Immunol* 2:331–340.
Potter et al. (1984), *Proc. Natl. Acad. Sci. USA.* 81(22):7161–7165.
Prat, M. et al. (1998), *J. Cell. Sci.* 111(Pt2):237–247.
Ramunsen et al. (1997), *Electrophoresis.* 18:588–598.
Reid L. H. et al. (1990), *Proc. Natl. Acad. Sci. U.S.A.* 87:4299–4303.
Risch, N. and Merikangas, K (1996), *Science.* 273:1516–1517.
Robertson E., (1987), Embryo-derived stem cell lines. In: E. J. Robertson Ed. *Teratocarcinomas and embrionic stem cells: a practical approach.* IRL Press, Oxford, pp. 71.
Robbins et al. (1987), *Diabetes.* 36:838–845.
Roguska M. A. et al. (1994), *PNAS* 91:969–973.
Rossi et al. (1991), *Pharmacol. Ther.* 50:245–254.
Roth J. A. et al. (1996), *Nature Medicine.* 2(9):985–991.
Rothwell, N. L. and Stock M. J. (1979), *Natrue.* 281:31–35.
Ron et al. (1993), *Biol Chem.,* 268 2984–2988.
Roux et al. (1989), *Proc. Natl. Acad. Sci. U.S.A.* 86:9079–9083.
Ruano et al., (1990) *Proc. Natl. Acad. Sci. U.S.A.* 87:6296–6300.
Ryan, K. R. et al. (1994), *Mol. Biol. Cells,* 529–538.
Sambrook, J., Fritsch, E. F., and T. Maniatis. (1989), *Molecular Cloning: A Laboratory Manual.* 2ed. Cold Spring Harbor Laboratory, Cold Spring Harbor, N.Y.
Samson M, et al. (1996), *Nature.* 382(6593):722–725.
Samulski et al. (1989), *J. Virol.* 63:3822–3828.
Sanchez-Pescador R. (1988), *J. Clin. Microbiol.* 26(10):1934–1938.
Sarkar, G. and Sommer S. S. (1991), *Biotechniques.*
Sauer B. et al. (1988), *Proc. Natl. Acad. Sci. U.S.A.* 85:5166–5170.
Sawai, H., et al. (1995), *AJRI* 34:26–34.
Schaid D. J. et al. (1996), *Genet. Epidemiol.* 13:423–450.
Schedl A. et al. (1993a), *Nature.* 362: 258–261.
Schedl et al. (1993b), *Nucleic Acids Res.* 21: 4783–4787.
Schena et al. (1995), *Science.* 270:467–470.
Schena et al. (1996), *Proc Natl Acad Sci U S A.* . 93(20):10614–10619.
Schneider et al. (1997), *Arlequin: A Software For Population Genetics Data Analysis.* University of Geneva.
Schwartz and Dayhoff, eds. (1978), *Matrices for Detecting Distance Relationships Atlas of Protein Sequence and Structure,* Washington: National Biomedical Research Foundation.
Sczakiel G. et al. (1995), *Trends Microbiol.* 3(6):213–217.
Segui-Real, B er al. (1994), *EMBOJ.* 12:2211–2218.
Shay J. W. et al. (1991), *Biochem. Biophys. Acta.* 1072: 1–7.
Sheffield, V. C. et al. (1991), *Proc. Natl. Acad. Sci. U.S.A.* 49:699–706.
Shizuya et al. (1992), *Proc. Natl. Acad. Sci. U.S.A.* 89:8794–8797.
Shoemaker D D, et al. (1996), *Nat Genet.* 14(4):450–456.
Shu, L. et al., (1993), *PNAS* 90:7995–7999.
Skerra, A et al. (1988), *Science* 240:1038–1040.
Smith (1957) *Ann. Hum. Genet.* 21:254–276.
Smith et al. (1983) *Mol. Cell. Biol.* 3:2156–2165.
Smith and Johnson (1988), *Gene.* 67:31–40.
Sosnowski R G, et al (1997), *Proc Natl Acad Sci U S A.* 94:1119–1123.
Sowdhamini et al. (1997) *Protein Engineering.* 10:207, 215.
Spielmann S. and Ewens W. J. (1998), *Am. J. Hum. Genet.* 62:450–458.
Spielmann S. et al. (1993), *Am. J. Hum. Genet.* 52:506–516.
Sternberg N. L. (1992), *Trends Genet.* 8:1–16.
Sternberg N. L., (1994), *Mamm. Genome.* 5:397–404.
Stryer, L., (1995), *Biochemistry.* 4th edition.
Studnicka G. M. et al. (1994), *Protein Engineering.* 7(6):805–814.
Sutcliffe, J. G. et al. (1983), *Science.* 219:660–666.
Syvanen A. C, (1994), *Clin Chim Acta.* 226(2):225–236.
Szabo A. et al. (1995), *Curr Opin Struct Biol.* 5, 699–705.
Tacson et al. (1996), *Nature Medicine.* 2(8):888–892.
Taryman, R. E. et al. (1995), *Neuron.* 14(4):755–762.
Te Riele et al. (1990) *Nature.* 348:649–651.
Terwilliger J. D. and Ott J. (1994), *Handbook of Human Genetic Linkage, John Hopkins University Press, London.*
Thomas K. R. et al. (1986) *Cell.* 44:419–428.
Thomas K. R. et al (1987), *Cell.* 51:503–512.
Thompson et al. (1994), *Nucleic Acids Res.* 22(2):4673–4680.
Tur-Kaspa et al. (1986), *Mol. Cell. Biol.* 6:716–718.
Tutt, A. et al. (1991), *J. Immunol.* 147:60–69.

Traunecker et al. (1988), *Nature.* 331:84–86.
Tyagi et al. (1998), *Nature Biotechnology.* 16:49–53.
Urdea M. S. (1988), *Nucleic Acids Research.* 11:4937–4957.
Urdea M. S. et al. (1991), *Nucleic Acids Symp. Ser.* 24:197–200.
Vaitukaitis, J. et al. (1971), *J. Clin. Endocrinol. Metab.* 33:988–991.
Valadon P., et al. (1996), *J. Mol. Biol.* 261:11–22.
Van der Lugt et al. (1991), *Gene.* 105:263–267.
Vil, H. et al. (1992) *PNAS.* 89:11337–11341.
Vlasak R. et al. (1983), *Eur. J. Biochem.* 135:123–126.
Wabiko et al. (1986), *DNA.* 5(4):305–314.
Walker et al. (1996), *Clin. Chem.* 42:9–13.
Wang et al. (1997), *Chromatographia,* 44:205–208.
Warden et al, *In Regulation of Body Weight: biological and behavioral mechanisms,* C. Bouchard and G. A. Bray, eds. West Sussex; John Wiley & Sons Ltd., pp. 285–305)
Weir, B. S. (1996), *Genetic data Analysis II: Methods for Discrete population genetic Data, Sinauer Assoc., Inc., Sunderland, Mass., U.S.A.*
Westerink M. A. J., (1995), *Proc. Natl. Acad. Sci.* 92:4021–4025.
White, M. B. et al. (1992), *Genomics.* 12:301–306.
White, M. B. et al. (1997), *Genomics.* 12:301–306.
Wiley J., and Sons Inc. (1997), *Current Protocols in Molecular Biology.*
Wilson et al. (1983), *Cell* 37:767–778.
Wong et al. (1980), *Gene.* 10:87–94.
Wood S. A. et al. (1993), *Proc. Natl. Acad. Sci. USA,* 90: 4582–4585.
Wu and Wu (1987), *J. Biol. Chem.* 262:4429–4432.
Wu and Wu (1988), *Biochemistry.* 27:887–892.
Wu et al. (1989), *Proc. Natl. Acad. Sci. U.S.A.* 86:2757.
Yagi T. et al. (1990), *Proc. Natl. Acad. Sci. U.S.A.* 87:9918–9922.
Yoon, D. Y. et al. (1998), *J. Immunol.* 160(7):3170–3179.
Zhao et al. (1998), *Am. J. Hum. Genet.* 63:225–240.
Zheng, X. X. et al. (1995), *J. Immunol.* 154:5590–5600.
Zhu, Z. et al., (1998), *Cancer Res.* 58(15):3209–3214.
Zijlstra et al. (1989), *Nature.* 342–345.
Zou Y. R. et al. (1994), *Curr. Biol.* 4:1099–1103.

Each of the above references are incorporated herein by reference in their entirities.

What is claimed:

1. A composition comprising an isolated, purified, and recombinant polynucleotide, or complement thereof, wherein said polynucleotide comprises a nucleotide sequence selected from the group consisting of:
   (a) a nucleotide sequence encoding amino acids −68 to −1 of SEQ ID NO:2;
   (b) a nucleotide sequence encoding amino acids +1 to 240 of SEQ ID NO:2;
   (c) a nucleotide sequence encoding amino acids −68 to 240 of SEQ ID NO:2;
   (d) a nucleotide sequence encoding a polypeptide fragment of SEQ ID NO:2 having fatty acid metabolizing activity; and
   (e) a nucleotide sequence comprising SEQ ID NO:1.

2. The composition of claim 1, wherein said nucleotide sequence encodes amino acids −68 to −1 of SEQ ID NO:2.

3. The composition of claim 1, wherein said nucleotide sequence encodes amino acids +1 to 240 of SEQ ID NO:2.

4. The composition of claim 1, wherein said nucleotide sequence encodes amino acids −68 to 240 of SEQ ID NO:2.

5. The composition of claim 1, wherein said nucleotide sequence encodes a polypeptide fragment of SEQ ID NO:2 having fatty acid metabolizing activity.

6. A composition comprising an isolated, purified, and recombinant vector, wherein said vector comprises the polynucleotide of claim 1.

7. A prokaryotic or eukaryotic cell recombinant for the vector of claim 6.

8. A prokaryotic or eukaryotic cell recombinant for the polynucleotide of claim 1.

9. A composition comprising an isolated, purified, and recombinant polynucleotide, or complement thereof, wherein said polynucleotide comprises a fragment of SEQ ID NO:1 selected from the group consisting of:
   (a) a polynucleotide comprising a contiguous span of at least 300 nucleotides of SEQ ID NO:1;
   (b) a polynucleotide comprising nucleotides 280–999 of SEQ ID NO:1;
   (c) a polynucleotide comprising nucleotides 76–999 of SEQ ID NO:1; and
   (d) a polynucleotide comprising nucleotides 76–279 of SEQ ID NO:1.

10. The composition of claim 9, wherein said polynucleotide comprises a contiguous span of at least 150 nucleotides of SEQ ID NO:1.

11. The composition of claim 9, wherein said polynucleotide comprises a contiguous span of at least 300 nucleotides of SEQ ID NO:1.

12. The composition of claim 9, wherein said polynucleotide comprises nucleotides 280 to 999 of SEQ ID NO:1.

13. The composition of claim 9, wherein said polynucleotide comprises nucleotides 76 to 999 of SEQ ID NO:1.

14. The composition of claim 9, wherein said polynucleotide comprises nucleotides 76 to 279 of SEQ ID NO:1.

* * * * *

UNITED STATES PATENT AND TRADEMARK OFFICE
CERTIFICATE OF CORRECTION

PATENT NO. : 6,787,647 B1
DATED : September 7, 2004
INVENTOR(S) : Jean-Baptiste et al.

It is certified that error appears in the above-identified patent and that said Letters Patent is hereby corrected as shown below:

Column 8,
Line 50, "90%, 95," should read -- 90%, 95%, --.

Column 18,
Line 20, "acylcamitine" should read -- acylcarnitine --.

Column 20,
Line 15, "CCIP-1" should read -- CCRP-1 --.

Column 25,
Line 57, "experiments;" should read -- experiments, --.

Column 31,
Line 6, "Transzenic" should read -- Transgenic --.

Column 57,
Line 10, "(See, erg., Harlow" should read -- (See, *e.g.*, Harlow --.

Column 61,
Line 58, "state of having certain" should read -- state of having, certain --.

Column 69,
Line 14, "Feigner" should read -- Felgner --.

Column 72,
Line 12, "20, 25, 30 30, 40" should read -- 20, 25, 30, 40 --.

Column 73,
Line 55, "Affi Gelg®" should read -- Affi Gel® --.

UNITED STATES PATENT AND TRADEMARK OFFICE
CERTIFICATE OF CORRECTION

PATENT NO. : 6,787,647 B1
DATED : September 7, 2004
INVENTOR(S) : Jean-Baptiste et al.

It is certified that error appears in the above-identified patent and that said Letters Patent is hereby corrected as shown below:

Column 82,
Line 49, "New York 1-Creighton" should read -- New York 1-12. Creighton (1983) --.

Signed and Sealed this

Twenty-sixth Day of April, 2005

JON W. DUDAS
*Director of the United States Patent and Trademark Office*